(12) United States Patent
Ellwanger et al.

(10) Patent No.: US 10,273,309 B2
(45) Date of Patent: Apr. 30, 2019

(54) ANTIBODY BINDING SITES SPECIFIC FOR EGFRVIII

(71) Applicant: Affimed GmbH, Heidelberg (DE)

(72) Inventors: Kristina Ellwanger, Heidelberg (DE); Uwe Reusch, Maikammer (DE); Ivica Fucek, Frankfurt am Main (DE); Stefan Knackmuss, Plankstadt (DE); Vera Molkenthin, Tannesberg (DE); Melvyn Little, St. Peter-Ording (DE); Eugene Zhukovsky, Mannheim (DE)

(73) Assignee: AFFEMED GMBH, Heidelberg (DE)

( * ) Notice: Subject to any disclaimer, the term of this patent is extended or adjusted under 35 U.S.C. 154(b) by 60 days.

(21) Appl. No.: 15/015,261

(22) Filed: Feb. 4, 2016

(65) Prior Publication Data

US 2016/0152728 A1 Jun. 2, 2016

Related U.S. Application Data

(63) Continuation of application No. PCT/EP2014/002177, filed on Aug. 7, 2014.

(30) Foreign Application Priority Data

Aug. 7, 2013 (EP) .................................... 13179630
Oct. 21, 2013 (EP) .................................... 13189599

(51) Int. Cl.
C07K 16/28 (2006.01)
C07K 16/32 (2006.01)
C07K 16/30 (2006.01)
A61K 39/00 (2006.01)

(52) U.S. Cl.
CPC .............. *C07K 16/32* (2013.01); *C07K 16/28* (2013.01); *C07K 16/2809* (2013.01); *C07K 16/2863* (2013.01); *C07K 16/30* (2013.01); *A61K 2039/505* (2013.01); *C07K 2317/21* (2013.01); *C07K 2317/31* (2013.01); *C07K 2317/33* (2013.01); *C07K 2317/35* (2013.01); *C07K 2317/565* (2013.01); *C07K 2317/622* (2013.01); *C07K 2317/626* (2013.01); *C07K 2317/73* (2013.01); *C07K 2317/92* (2013.01)

(58) Field of Classification Search
None
See application file for complete search history.

(56) References Cited

FOREIGN PATENT DOCUMENTS

EP 2457586 A1 5/2012

OTHER PUBLICATIONS

Reusch et al., Characterization of CD33/cd3 tetravalent bispecific tandem diabodies (TandAbs) for the treatment of acute myeloid leukemia, Clin. Canc. Res., 22(23):5829-5838, 2016.*

(Continued)

*Primary Examiner* — Claire Kaufman
(74) *Attorney, Agent, or Firm* — Perkins Coie LLP; Viola T. Kung

(57) ABSTRACT

This application describes binding proteins that specifically bind to EGFRvIII and multispecific binding proteins that specifically bind to EGFRvIII and CD3. Further described is a multispecific tandem diabody that binds to EGFRvIII and CD3. Further described are highly cytotoxic EGFRvIII/CD3 bispecific tandem diabody for recruiting T cells to specifically and potently kill several types of solid tumor cancer.

21 Claims, 29 Drawing Sheets

Specification includes a Sequence Listing.

(56) References Cited

OTHER PUBLICATIONS

Kipriyanov S.M., Generation and Characterization of Bispecific Tandem Diabodies for Tumor Therapy. In: Welschof M., Krauss J. eds) Recombinant Antibodies for Cancer Therapy. Methods in Molecular Biology™, vol. 207, pp. 323-333. Humana Press. 2003.*
Kranz et al., Restricted reassociation of heavy and light chains from hapten-specific monoclonal antibodies, Proc. Natl. Acad. Sci. USA, 78(9):5807-11, Sep. 1981.*
Kang et al., Antibody redsign by chain shuffling from random combinatorial immunoglobulin libraries, Proc. Natl. Acad. Sci., USA, 88:11120-11123, Dec. 1991.*
Le Gall et al., Effect of linker sequences between the antibody variable domains on the formation,stability and biological activity of a bispecific tandem diabody, Protein Engineering 17:357-366 , 2004.*
Todorovska et al., Design and application of diabodies, triabodies and tetrabodies for cancer targetingJ. Immunol. Meth. 248:47-66, 2001.*
Choi, D. B. et al., "Systemic administration of a bispecific antibody targeting EGFRvIII successfully treats intracerebral glioma", Proceedings of the National Academy of Sciences, vol. 110, No. 1,, Dec. 17, 2012, pp. 270-275.

* cited by examiner

Figure 1A

| Clone | \|— VH CDR1 —\| | | | | | | | | | SEQ. ID. No | \|— VH CDR2 —\| | | | | | | | | | | | | | SEQ. ID. No |
|---|---|---|---|---|---|---|---|---|---|---|---|---|---|---|---|---|---|---|---|---|---|---|---|---|
| | X1 | X2 | X3 | X4 | X5 | X6 | X7 | X8 | X9 | | X10 | X11 | X12 | X13 | X14 | X15 | X16 | X17 | X18 | X19 | X20 | X21 | X22 | |
| 469 | Y | S | F | N | S | Y | W | I | G | 33 | G | I | I | Y | P | G | D | S | D | T | R | Y | S | 28 |
| 470 | Y | S | F | N | S | Y | W | I | G | 33 | G | I | I | Y | P | G | D | S | D | T | R | Y | S | 28 |
| 471 | Y | S | F | N | S | Y | W | I | G | 33 | G | I | I | Y | P | G | D | S | *A* | *N* | R | Y | S | 28 |
| 472 | Y | S | F | S | *Y* | Y | W | I | G | 42 | G | I | I | Y | P | G | D | S | *H* | T | R | Y | S | 43 |
| 473 | Y | S | F | S | *H* | Y | W | I | G | 46 | G | I | I | Y | P | G | D | S | D | T | R | Y | S | 28 |
| 474 | Y | S | F | S | S | Y | W | I | G | 49 | G | I | *T* | Y | P | *D* | D | *V* | D | T | R | Y | *D* | 50 |
| 475 | Y | S | F | T | S | Y | W | I | G | 53 | G | I | I | Y | P | G | D | S | D | T | R | Y | S | 54 |
| 476 | Y | S | F | T | S | Y | W | I | G | 53 | G | I | I | Y | P | G | D | S | D | T | R | Y | S | 28 |
| 477 | Y | S | F | S | S | Y | W | I | G | 46 | G | I | I | Y | P | G | D | *E* | D | T | R | Y | S | 61 |
| 478 | Y | S | F | N | S | Y | W | I | G | 33 | G | I | I | Y | P | G | D | S | D | T | *I* | Y | S | 63 |
| 479 | Y | *D* | F | S | * | Y | W | I | G | 69 | * | * | * | Y | P | * | D | * | D | T | * | Y | * | |
| Li3G30 | Y | S | F | * | S | Y | W | I | G | 27 | G | I | H | Y | P | G | D | S | D | T | R | Y | S | 28 |
| germline | Y | S | F | T | S | Y | W | I | G | 27 | G | I | H | Y | P | G | D | S | D | T | R | Y | S | 28 |

Figure 1B

| Clone | VL CDR1 | | | | | | | | | | | SEQ. ID. NO. | VL CDR2 | | | | | | | SEQ. ID. NO. | VL CDR3 | | | | | | | | | | | | SEQ. ID. NO. |
|---|---|---|---|---|---|---|---|---|---|---|---|---|---|---|---|---|---|---|---|---|---|---|---|---|---|---|---|---|---|---|---|---|---|
| | X23 | X24 | X25 | X26 | X27 | X28 | X29 | X30 | X31 | X32 | X33 | | X34 | X35 | X36 | X37 | X38 | X39 | X40 | | X41 | X42 | X43 | X44 | X45 | X46 | X47 | X48 | X49 | X50 | X51 | X52 | |
| 469 | S | G | D | A | L | P | K | Q | Y | A | Y | 34 | K | D | S | E | R | P | S | 31 | Q | S | V | D | V | S | G | T | Y | - | V | V | 35 |
| 470 | S | G | D | A | L | P | K | Q | Y | A | Y | 36 | K | D | S | E | R | P | S | 31 | Q | S | V | D | S | S | E | T | Y | - | V | V | 37 |
| 471 | S | G | D | A | L | P | K | Q | Y | A | Y | 39 | K | D | S | E | R | P | S | 40 | Q | S | V | D | S | S | H | P | S | - | V | V | 41 |
| 472 | S | G | D | Y | L | P | K | Q | Y | A | Y | 44 | K | D | S | E | R | P | S | 40 | Q | S | V | D | S | S | G | T | Q | - | V | V | 45 |
| 473 | S | G | H | A | L | P | S | Q | Y | A | Y | 47 | K | D | T | E | R | P | S | 40 | Q | S | V | D | S | S | G | T | S | - | V | I | 48 |
| 474 | S | G | D | A | L | P | K | T | Y | A | Y | 51 | K | D | T | E | R | P | S | 40 | Q | S | A | D | S | S | G | T | S | - | L | V | 52 |
| 475 | S | G | D | A | L | P | K | Q | Y | A | Y | 44 | K | D | T | E | R | P | S | 40 | Q | S | V | D | P | S | G | T | Y | - | V | V | 55 |
| 476 | S | G | D | A | N | I | K | Q | Y | A | Y | 56 | K | D | T | E | R | P | A | 57 | Q | S | A | D | A | T | G | A | Y | - | L | V | 58 |
| 477 | S | G | D | A | Y | P | H | Q | Y | A | Y | 59 | K | D | T | E | R | P | S | 40 | Q | S | A | D | P | S | G | T | Y | - | V | V | 60 |
| 478 | S | G | D | A | L | P | K | Q | Y | A | Y | 44 | K | D | T | E | R | P | S | 40 | Q | S | V | D | S | S | G | T | Y | - | Y | V | 62 |
| 479 | S | G | D | A | A | P | E | Q | Y | A | Y | 64 | K | D | S | E | R | P | S | 31 | Q | S | V | D | S | S | G | T | F | - | Y | V | 65 |
| Li3G30 | S | G | * | * | * | * | * | * | * | * | * | | | | * | | | | | | * | | * | | * | | * | * | * | del | * | * | |
| germline | S | G | D | A | L | P | K | Q | Y | A | Y | 30 | K | D | S | E | R | P | S | 31 | Q | S | A | D | S | S | G | T | P | L | H | V | 32 |
| | | | | | | | | | | | | | | | | | | | | | | | | | | | | | | | | | 70 |

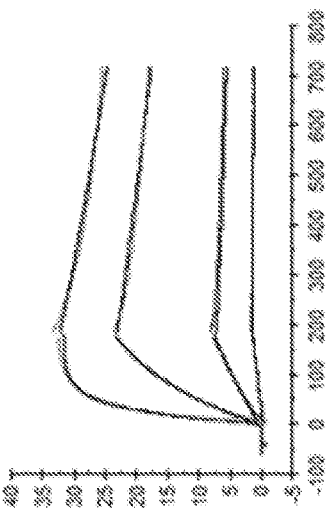
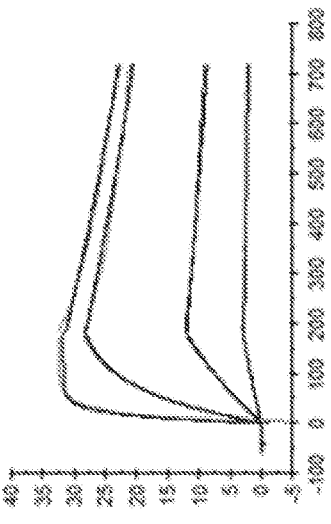
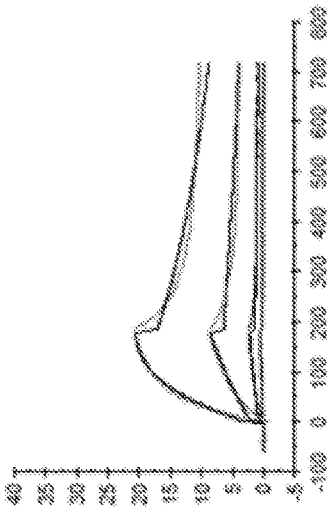
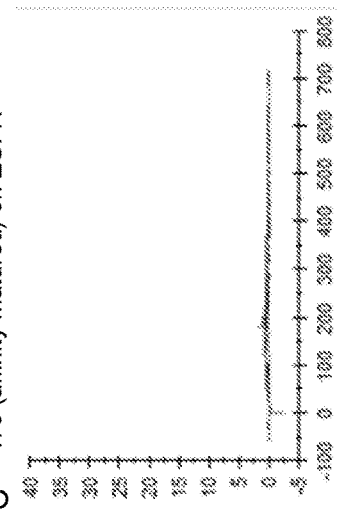
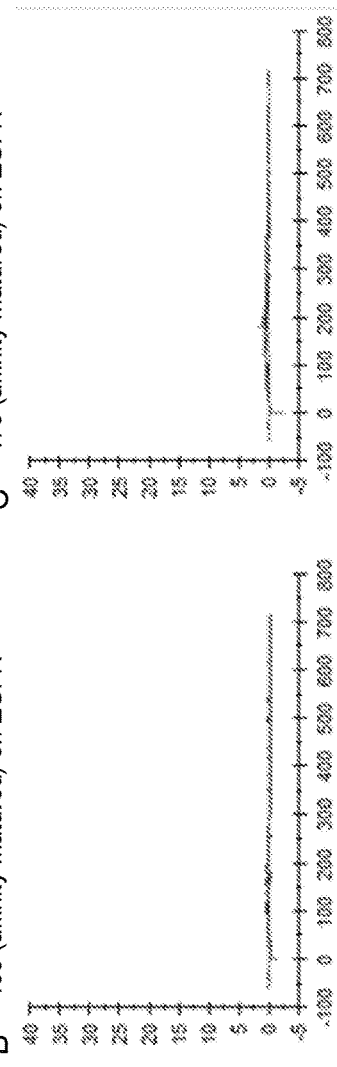
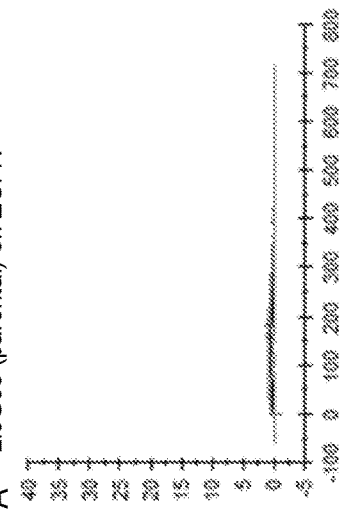
Figure 2A, Figure 2B, Figure 2C

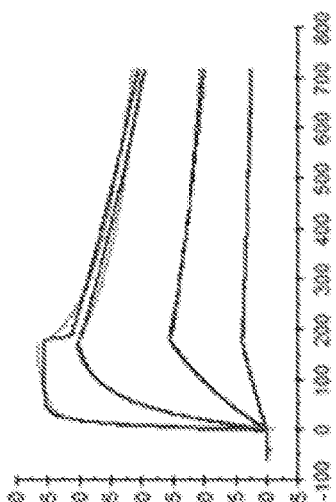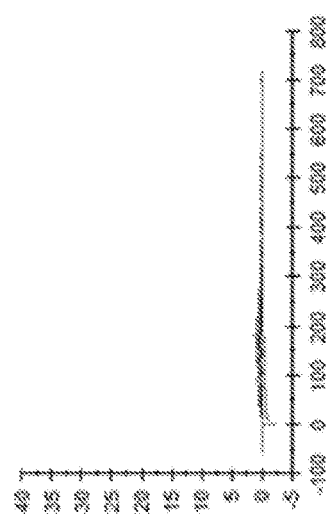
Figure 2D    Figure 2E    Figure 2F

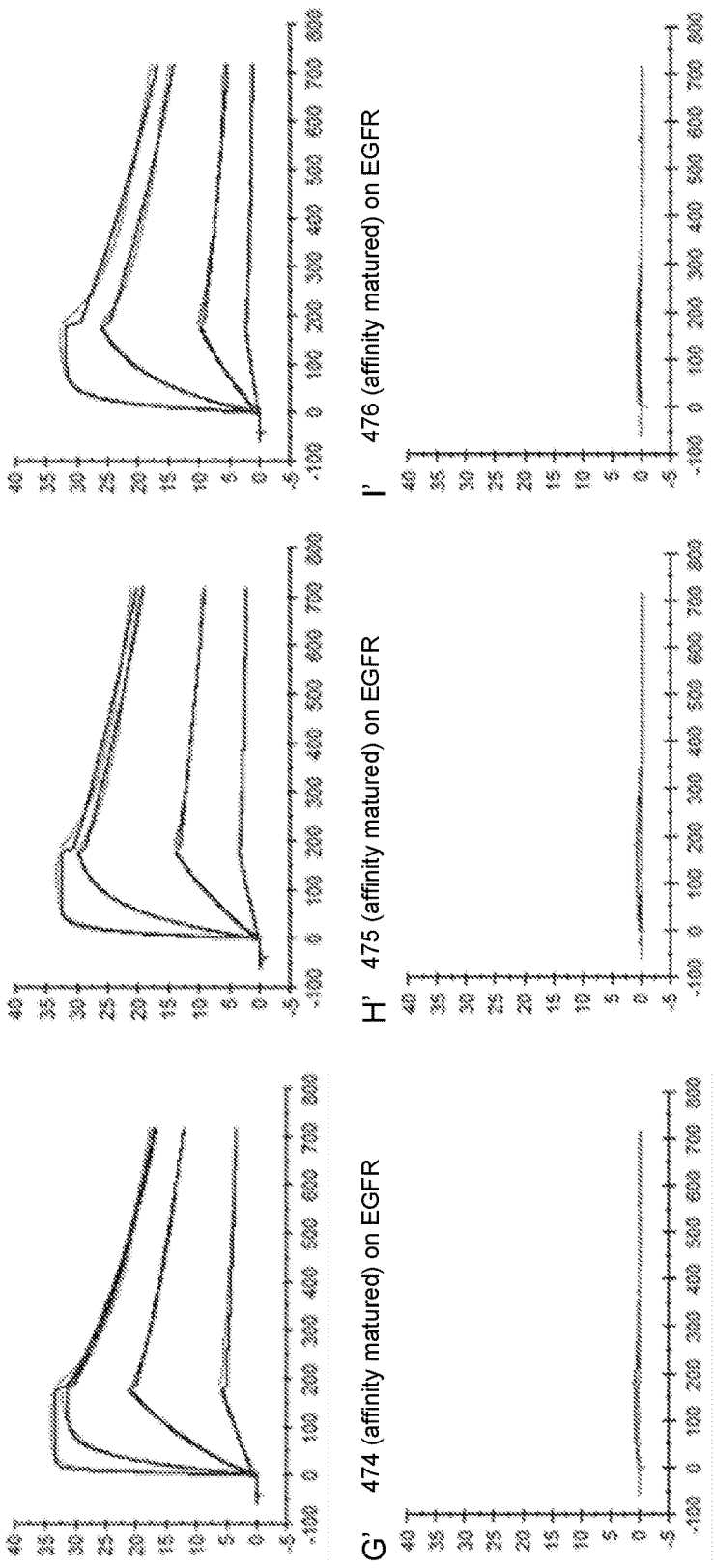

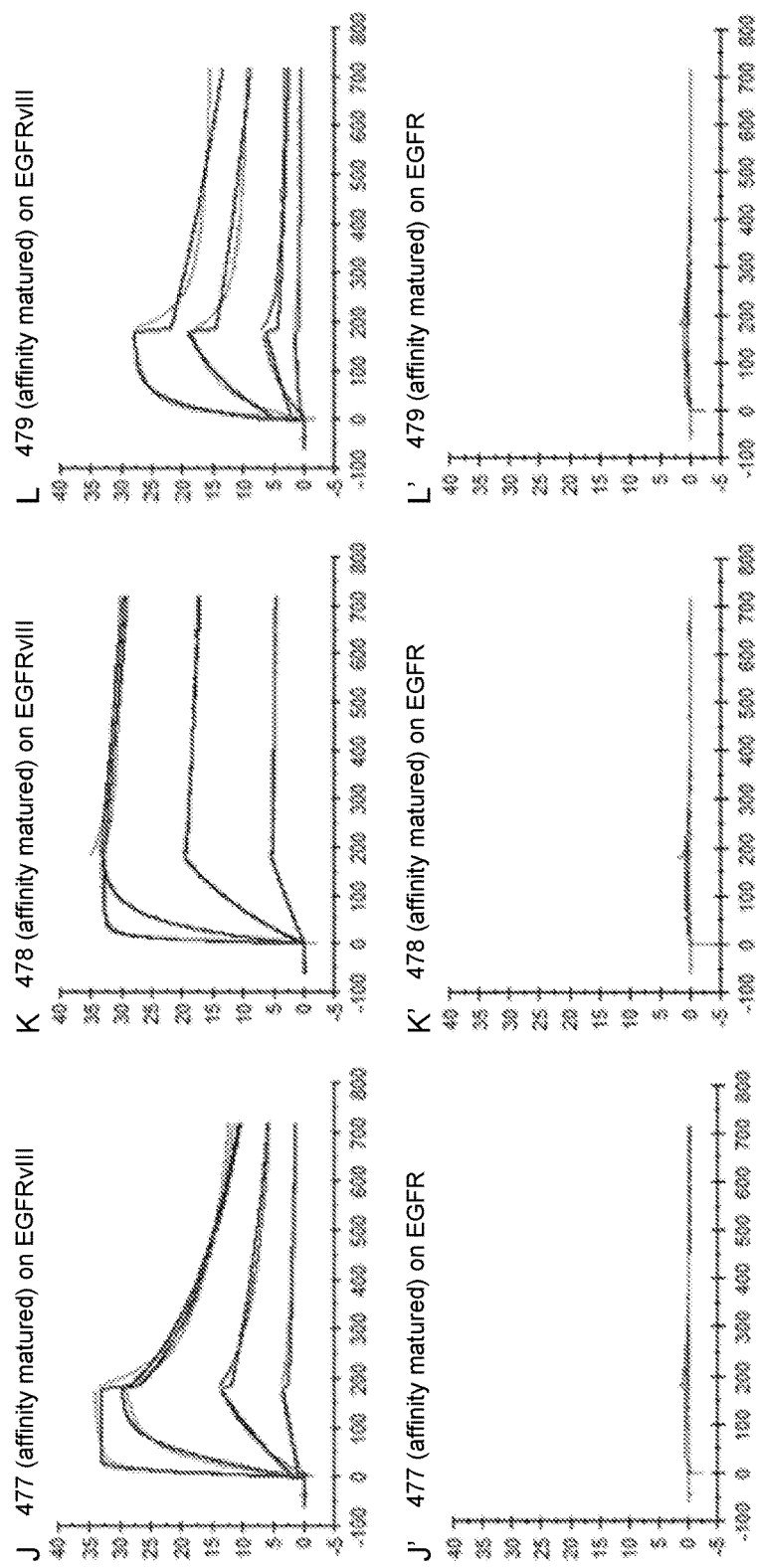

(legend also applies to the graphs on the following page)

Figure 5B
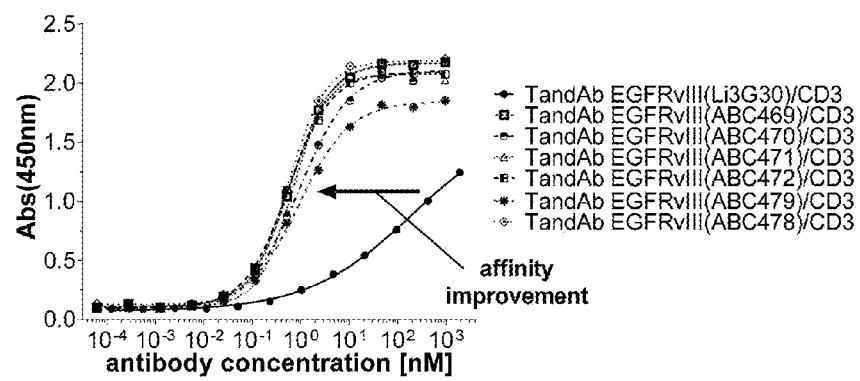
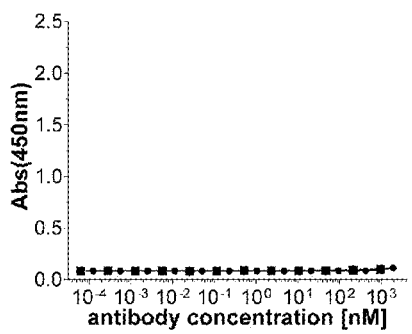
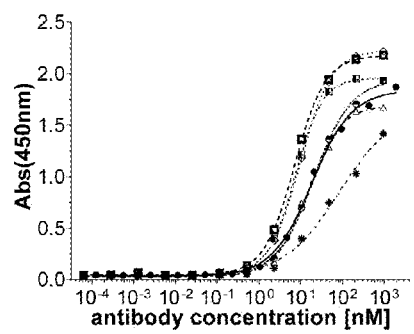

A      EGFRvIII/CD3 TandAb containing Li3G30 (parental)
(7 concentrations; range: 90 nM – 0.12 nM; dilution factor: 3)
Binding on EGFRvIII B      EGFRvIII/CD3 TandAb containing ABC 469 (affinity matured)
(6 concentrations; range: 150 nM – 0.048 nM; dilution factor: 5)
Binding on EGFRvIII Figure 8C
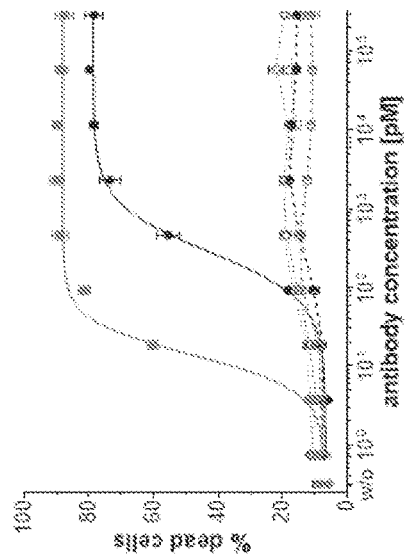
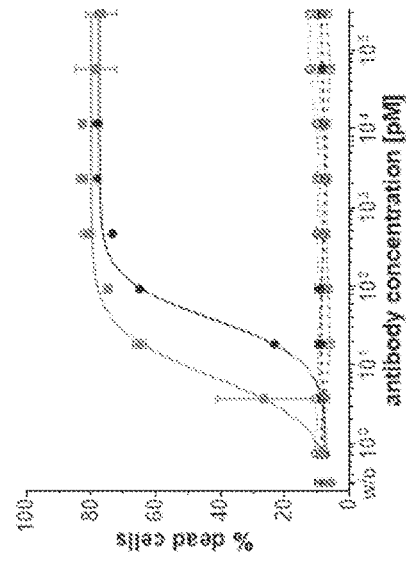

ANTIBODY BINDING SITES SPECIFIC FOR EGFRVIII

This application is a continuation of PCT/EP2014/002177, filed Aug. 7, 2014; which claims the priority of EP 13189599.7, filed Oct. 21, 2013, and EP 13179630.2, filed Aug. 7, 2013. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Feb. 3, 2016, and a size of 35.7 kilobytes. The Sequence Listing filed via EFS-Web is part of the specification and is hereby incorporated in its entirety by reference herein.

TECHNICAL FIELD

The present invention relates to binding proteins that specifically bind to EGFRvIII and to multispecific binding proteins that specifically bind to EGFRvIII and CD3. The invention further extends to a multispecific tandem diabody that binds to EGFRvIII and CD3. In particular, the invention relates to highly cytotoxic EGFRvIII/CD3 bispecific tandem diabody (TandAb®) for recruiting T cells to specifically and potently kill several types of solid tumor cancers.

BACKGROUND

EGFR dysregulation has been linked to numerous cancers and both, small molecules and EGFR targeting antibodies have successfully reached the clinic. However, the antibodies approved for clinical use, and those in development, all share a severe side effect profile due to the broad normal tissue-expression of EGFR. The deletion variant III of EGFR (EGFRvIII), with truncated extracellular domain and ensuing ligand-independent constitutive activity, is the most common mutant form associated with oncogenic transformation. EGFRvIII is expressed exclusively in cancer tissues and is associated with various solid tumor types.

BRIEF DESCRIPTION OF THE DRAWINGS

FIGS. 1A-1B illustrate variable sequence positions in the EGFRvIII specific, high affinity binding domains derived after affinity maturation. CDR positions of the heavy and light chain variable regions which differ from the parental sequence are indicated with asterisks and the respective amino acids cursive and underlined. Positions with beneficial mutations are highlighted in bold.

FIGS. 2A-2L show results from the multi-cycle kinetics measurement of binding of different scFv antibodies to recombinant EGFRvIII-Fc antigen or wild type EGFR-Fc antigen in a Biacore T200. Sensograms show the kinetics of Surface plasmon resonance (SPR) response units (RU) measured over time at 4 different concentration levels of scFv antibody (86 nM, 17.2 nM, 3.4 nM, 0.69 nM). Association is measured for 180 seconds, dissociation is measured thereafter. Data is analysed using a 1:1 binding model.

FIGS. 5A-5C show the concentration dependent binding of different EGFRvIII/CD3 specific tandem diabodies to EGFRvIII-Fc, EGFR-Fc, and CD3γε recombinant antigens analysed in ELISA. Binding signals are shown in (A) for EGFRvIII/CD3 specific tandem diabodies with the domain order $V_L^{CD3}$-$V_H^{EGFRvIII}$-$V_L^{EGFRvIII}$-$V_H^{CD3}$, in (B) for the EGFRvIII/CD3 specific tandem diabodies with the domain order $V_H^{EGFRvIII}$-$V_L^{CD3}$-$V_H^{CD3}$-$V_L^{EGFRvIII}$, and in (C) for the EGFRvIII/CD3 specific tandem diabodies containing the CD3 domain of SEQ ID NOs: 23, 24 and having the domain order $V_L^{CD3}$-$V_H^{EGFRvIII}$-$V_L^{EGFRvIII}$-$V_H^{CD3}$. Improvement in the binding to EGFRvIII for tandem diabodies containing affinity matured EGFRvIII-binding domains is clearly detectable as a shift of the respective binding curves to lower concentrations in all formats/domain orders.

FIGS. 8A-8C illustrate the improvements in the cytotoxic potency, efficacy and target-dependent specificity of EGFRvIII/CD3 tandem diabodies containing the different affinity matured EGFRvIII-specific binding domains in comparison to respective tandem diabodies containing the parental EGFRvIII binding domain (Li3G30) prior to the affinity maturation on EGFRvIII positive cells: (A) ABC 470 containing EGFRvIII/CD3 tandem diabodies, (B) ABC 471 containing EGFRvIII/CD3 tandem diabodies, (C) ABC 472 containing EGFRvIII/CD3 tandem diabodies. Antibody concentration dependent cytotoxicity was measured in a flow cytometry based assays using EGFRvIII expressing CHO cells ($CHO^{EGFRvIII}$), EGFRvIII negative EGFR expressing CHO cells ($CHO^{EGFR}$), or untransfected CHO cells as target cells and human PBMCs as effector cells. In each panel (A-C), tandem diabodies containing the individual EGFRvIII binding domains and the CD3 domain v64 in the order $V_L^{CD3}$-$V_H^{EGFRvIII}$-$V_L^{EGFRvIII}$-$V_H^{CD3}$ are shown on the left, and tandem diabodies containing the individual EGFRvIII binding domains combined with a different CD3 domain in the order $V_H^{EGFRvIII}$-$V_L^{CD3}$-$V_H^{CD3}$-$V_L^{EGFRvIII}$ On the right.

DETAILED DESCRIPTION OF THE INVENTION

The restricted EGFRvIII expression on cancer cells provides an opportunity to develop cytotoxic antibodies that exclusively target cancer, sparing normal tissues, and substantially reduce the side effects associated with EGFR therapy.

Figure 9:
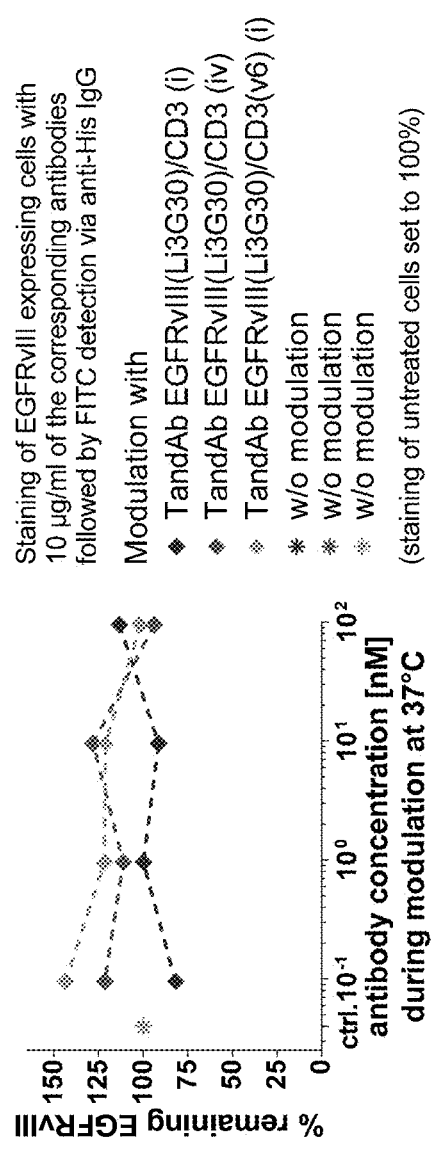
FIG. 9 shows results from the assessment of EGFRvIII receptor internalization from the cell surface upon binding of EGFRvIII-specific antibodies. EGFRvIII expressing cells were incubated with different concentrations of three different EGFRvIII/CD3 tandem diabodies antibodies having the domain order $V_L^{CD3}$-$V_H^{EGFRvIII}$-$V_L^{EGFRvIII}$-$V_H^{CD3}$ (i), or $V_H^{EGFRvIII}$-$V_L^{CD3}$-$V_H^{CD3}$-$V_L^{EGFRvIII}$ (iv), and/or containing different CD3-binding domains, at 37° C. for 24 hours. After the modulation, the respective tandem diabodies antibodies were used at a saturating concentration of 10 μg/ml to stain all remaining EGFRvIII receptor molecules on the cell surface.

In a first aspect of the invention, described herein are fully human, highly specific, high-affinity EGFRvIII binding proteins. The described EGFRvIII binding proteins possess the following advantages:

They facilitate no or very low internalization of the EGFRvIII from the cell surface of target positive cells, which is beneficial for recruiting cytotoxic T- or NK-cells. The results presented in FIG. 9 show that, relative to untreated cells of the EGFRvIII receptor molecule still remains on the cell surface after the exposure of the cells to the EGFRvIII-binding proteins according to the invention, under all conditions tested. These results suggest, that EGFRvIII/CD3 binding proteins according to the invention surprisingly do not show any internalization tendency (FIG. 9). Instead of inducing internalization, binding of the EGFRvIII-specific binding proteins according to the invention might either inhibit internalization or facilitate increased expression of EGFRvIII leading to its increased cell surface density.

These high-affinity binding proteins could have their affinity be further substantially improved employing affinity maturation techniques to obtain binding proteins specific for EGFRvIII with the $K_D$ in the 100 pM range or lower. The surprising fact is that these binding proteins demonstrate exquisite specificity of binding to EGFRvIII with no cross-reactivity to the native EGFR (wild type EGFR or EGFRwt). The neo-epitope in EGFRvIII relative to EGFRwt is formed due to the in-frame deletion of 269 amino acids from the extra cellular domain of EGFR (exons 2-7), and is expected to be rather small: it consists of the novel juxtaposition of amino acids (amino acid 5 is fused to amino acid 274) and a single novel GLY amino acid at the deletion site.

The affinity maturation screening procedure was aimed at improving binding affinity by facilitating the selection of the binding proteins with reduced dissociation rate ($k_{OFF}$). However, surprisingly, affinity maturated binding proteins displayed substantially increased association rate ($k_{ON}$), whereas the reduction of $k_{OFF}$ had only a minor contribution to the up to 100-fold improved binding of the binding proteins, with some variable antibody domains exhibiting $K_D$ below 100 pM.

These unique properties make these variable antibody domains specific for EGFRvIII described here specifically suited for the development of multispecific, e.g. bispecific, multivalent, immune effector cell engaging, tumor targeting antibody therapeutics, such as, for example, the EGFRvIII/CD3 bispecific tandem diabody (TandAb®).

In a further aspect of this invention, multivalent EGFRvIII binding antibodies are provided, having two binding sites for the EGFRvIII or in the case of multivalent bispecific antibodies, having in addition to two binding sites for EGFRvIII, binding sites for the T-cell antigen CD3 or for CD16A expressed specifically on natural killer (NK) cells.

Figure 3A:
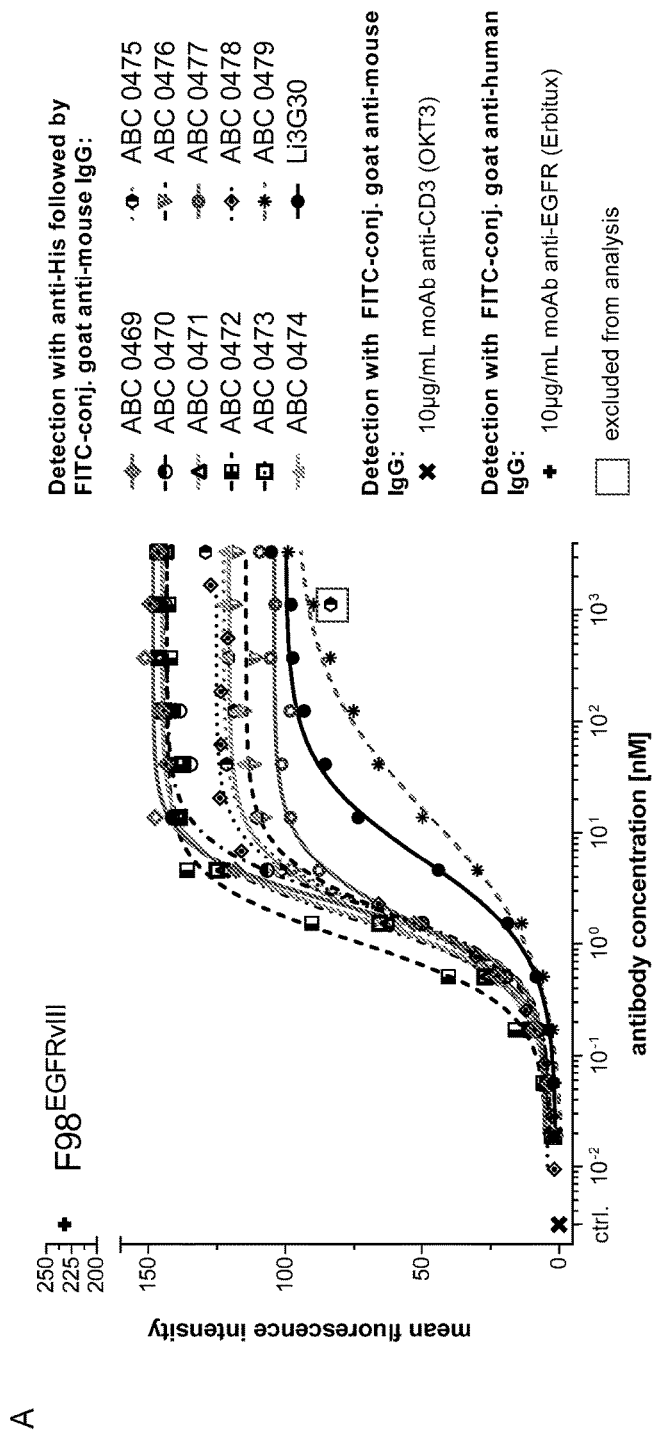
FIGS. 3A-3F show results from flow cytometic measurement of binding of scFv antibodies to (A) F98 rat glioma cells overexpressing EGFRvIII (F98$^{EGFRvIII}$), (B) F98 cells overexpressing native EGFR (F98$^{EGFR}$), (C) untransfected F98 cells (F98), as well as binding of the same scFv antibodies to (D) CHO cells overexpressing EGFRvIII (CHO$^{EGFRvIII}$), (E) CHO cells overexpressing native EGFR (CHO$^{EGFR}$) and (F) untransfected CHO cells (CHO).
Figure 3C:
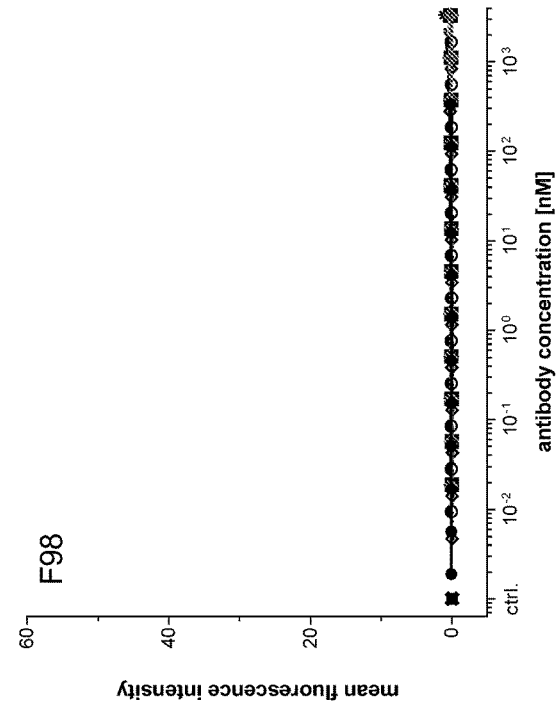
Figure 3B:
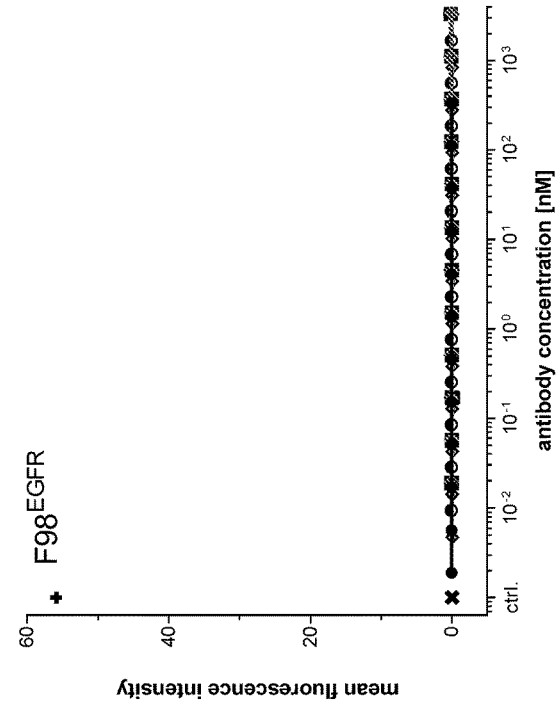
Figure 3D:
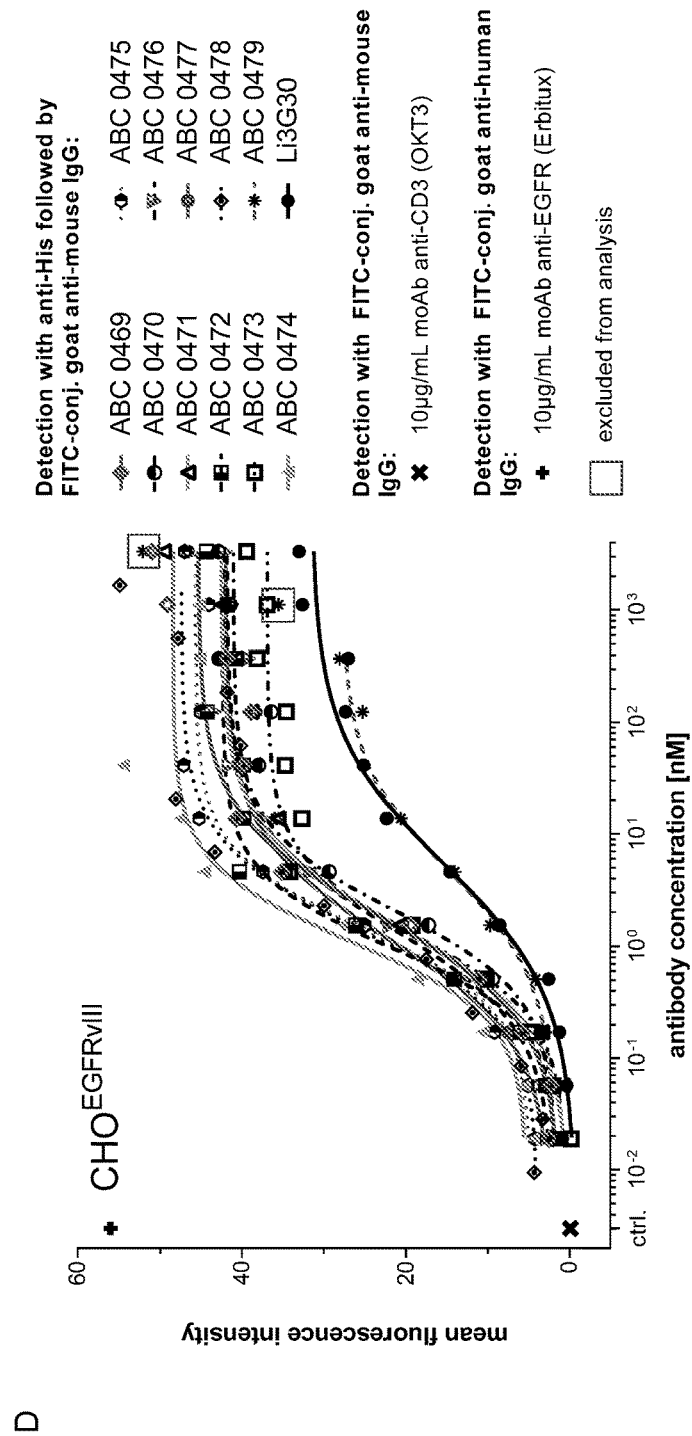
Figure 3F:
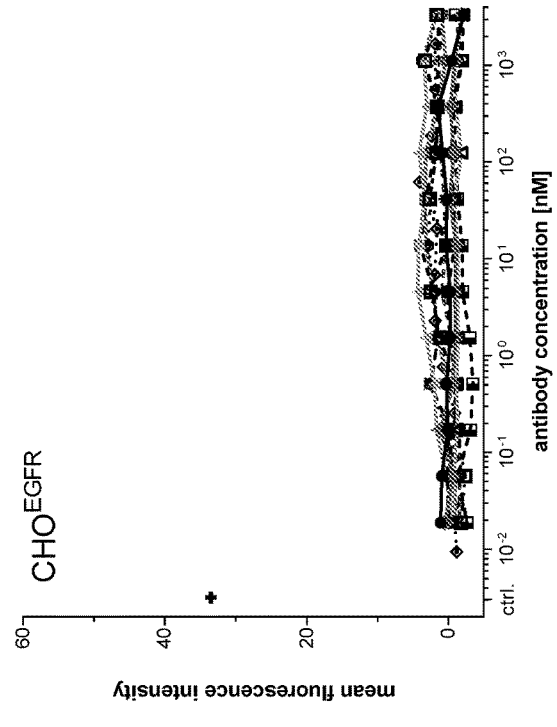
Figure 3E:
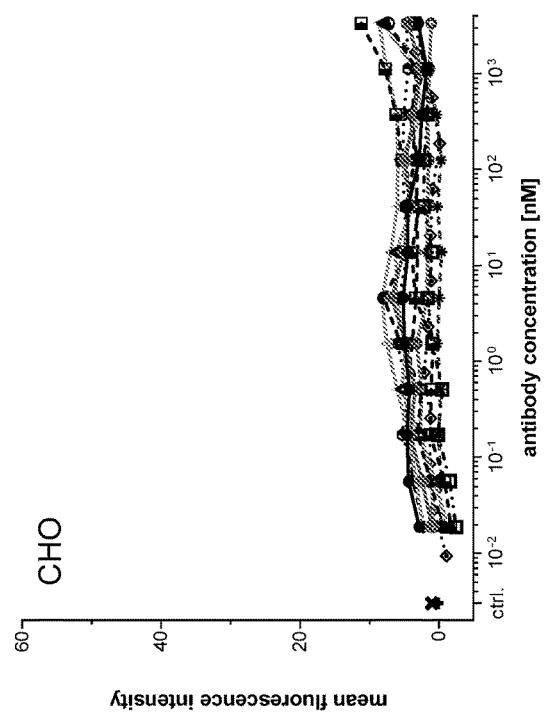
Figure 4A:
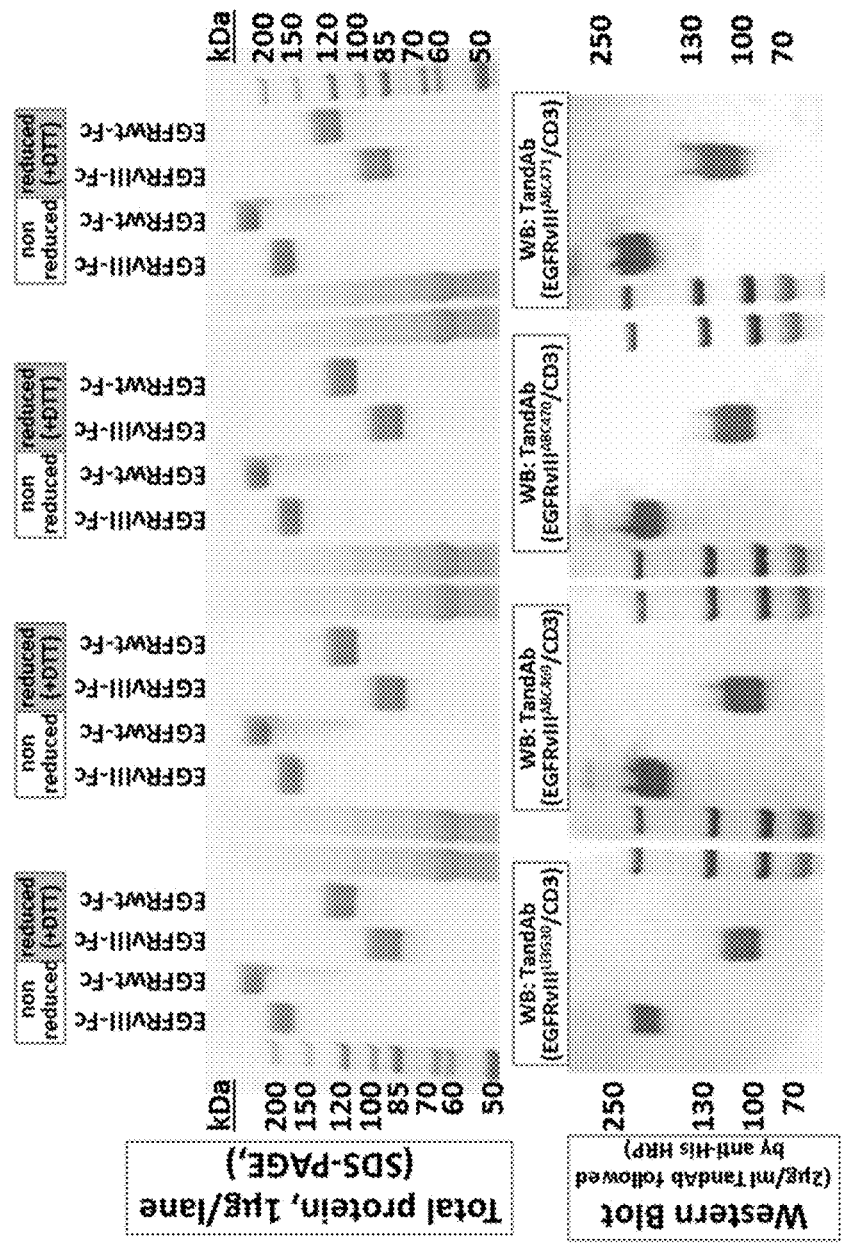
FIGS. 4A and 4B illustrate the binding of tandem diabodies containing different EGFRvIII binding domains to purified EGFRvIII- or native EGFR-Fc fusion antigens (non-reduced protein or protein reduced with DTT) which were separated by SDS-PAGE and transferred to a PVDF membrane by Western Blotting. The Fc-fusion proteins dimerize via disulfide bonds in the Fc portion but are monomeric after reduction with DTT. EGFRvIII-specific antibodies bind to the EGFRvIII-fusion antigen in the reduced and non-reduced conformation, but do not bind to the native EGFR. The anti-EGFR antibody Cetuximab was used as a control and recognizes both, the non-reduced EGFRvIII-Fc and the non-reduced EGFR-Fc antigen, but not the DTT-treated antigens.
Figure 4B:
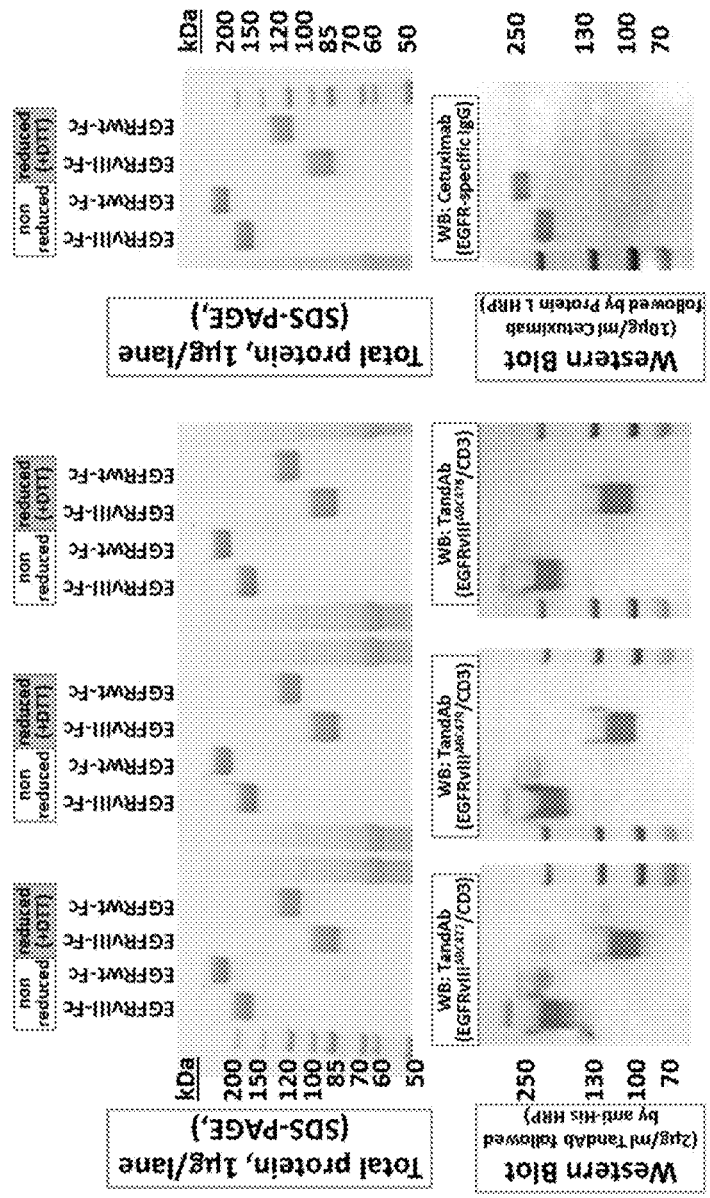

In one example EGFRvIII/CD3 tandem diabodies having two binding sites for EGFRvIII and additionally containing two binding sites for CD3 were used, and their binding to recombinant EGFRvIII- or EGFR-Fc fusion antigens were tested. The EGFRvIII- or EGFR-Fc fusion antigens were separated by SDS-PAGE either under non-reducing conditions (molecular structures remain partially preserved due to intact disulfide bonds), or under reducing conditions (protein structure is fully denatured), transferred to a PVDF membrane by Western Blotting and assessed for binding using different EGFRvIII/CD3 tandem diabody antibodies or the EGFR-binding IgG Cetuximab to decorate the blot (FIG. 4). The example shows that both, the parental and affinity matured EGFRvIII binding domains maintain their selective specificity for EGFRvIII also in multivalent antibody formats, containing two binding sites for EGFRvIII. All EGFRvIII/CD3 tandem diabodies recognize EGFRvIII both, under reducing and non-reducing conditions, but fail to recognize the full length wild type EGFR under any of these conditions. This example furthermore demonstrates that the EGFRVIII-specific binding domains described here recognize a linear epitope and do not require intact 3-dimensional structures for their reactivity. This is in contrast to the EGFR-binding IgG antibody Cetuximab (Erbitux), that recognizes both, wild type EGFR, as well as the mutated EGFRvIII, but clearly requires intact disulfide bonds for its reactivity with a conformational epitope (FIG. 4).

In another example EGFRvIII/CD3 tandem diabodies were used containing the parental, or affinity matured EGFRvIII specific domains combined with different CD3 binding domains and/or having a different order of the individual binding domains in the Tandem diabody molecules. Tandem diabodies with the domain order $V_L^{CD3}$-$V_H^{EGFRvIII}$-$V_L^{EGFRvIII}$-$V_H^{CD3}$ contain bivalent EGFRvIII binding sites in the middle of the tandem diabody molecules, whereas Tandem diabodies with the domain order $V_H^{EGFRvIII}$-$V_L^{CD3}$-$V_H^{CD3}$-$V_L^{EGFRvIII}$ have the two EGFRvIII binding sites in the outer position and the two CD3 binding sites in the middle. The different EGFRvIII-domain containing and domain order variants of tandem diabodies were analysed for their concentration-dependent binding to EGFRvIII antigen, wild type EGFR antigen, as well as binding to the CD3 antigen in ELISA (FIG. 6). All tandem diabodies containing affinity matured EGFRvIII binding domains showed a substantially improved binding to EGFRvIII, clearly visible as a shift of the corresponding binding curves to lower concentrations by more than two orders of magnitude (FIG. 6). Binding to the wild type EGFR antigen was not observed for any of the tandem diabodies.

Figure 10:
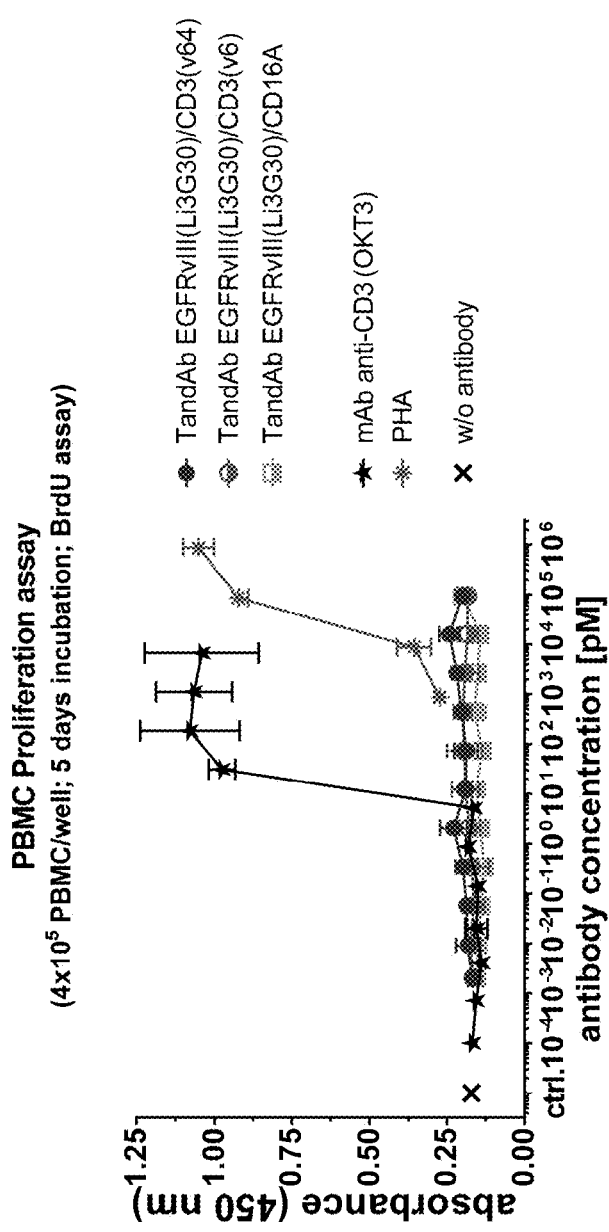
FIG. 10 shows results from the assessment of cell proliferation (BrdU incorporation) in human PBMC cultures in the presence of EGFRvIII/CD3 (or EGFRvIII/CD16A) tandem diabodies antibodies. PBMCs proliferate in the presence of the CD3 binding antibody OKT3 or the plant lectin phytohemagglutinin (PHA) which are used as positive controls. Incubation of PBMCs with different EGFRvIII/CD3 tandem diabodies in the absence of EGFRvIII-positive target cells does not induce activation and proliferation of PBMCs.

Anti-EGFRvIII antibodies, e.g. antigen-binding proteins that selectively bind to the mutated and not to the native form of EGFR can be selected and identified by phage display libraries. T cells are potent tumor-killing effector cells that cannot be recruited by native antibodies. Therefore, in a further aspect of the invention a panel of multi-specific EGFRvIII/CD3 antigen-binding proteins, in particular tandem diabodies are provided according to the invention, capable of T cell-recruitment, with a broad range of binding and cytotoxic properties. The binding properties, T cell-mediated cytotoxic activity, and target-mediated T cell activation of the antigen-binding proteins according to the invention are characterized in a panel of in vitro assays. The antigen-binding proteins according to the invention exhibit exquisite specificity towards EGFRvIII antigen in Biacore, ELISA and EGFRvIII-positive cells in FACS assays. No detectable binding was observed with any of the binding proteins on EGFR antigen or on EGFRwt-expressing cells over the complete concentration range tested. The most potent high affinity tandem diabodies display cytotoxicity towards EGFRvIII-expressing F98 glioma and CHO cells with EC50 in 1 pM-10 pM range; remaining tandem diabodies displayed cytotoxicity with EC50 up to about 10000 pM. The cytotoxicity of these tandem diabodies towards EGFRwt+ cells as a more sensitive probe of residual binding to the native form is also assayed. No cytotoxicity is observed on EGFRwt+ cells or other EGFRvIII-negative cells up to the maximally-evaluated tandem diabody concentration of 0.5 μM. High affinity binding to CD3 is essential for efficacious T cell recruitment and yet, in the absence of EGFRvIII+ target cells in vitro, tandem diabodies according to the invention do not elicit T cell activation, as measured by their lack of proliferation, contributing to a good preclinical safety profile (FIG. 10). In summary, a strict specificity and high potency of the anti-tumor cytotoxicity is mediated by the EGFRvIII/CD3 tandem diabody.

Figure 11:
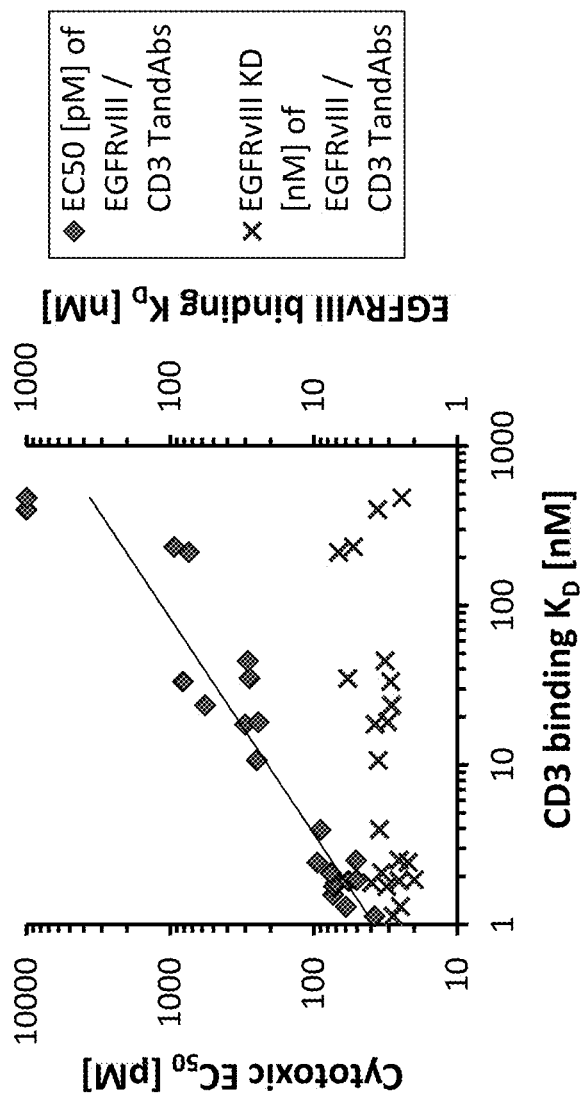
FIG. 11 illustrates the positive correlation of CD3-binding affinities of EGFRvIII/CD3 tandem diabodies with their cytotoxic potency. More than 20 EGFRvIII/CD3 tandem diabodies all containing the identical EGFRvIII binding domain (Li3G30) combined in the domain order $V_L^{CD3}$-$V_H^{EGFRvIII}$-$V_L^{EGFRvIII}$-$V_H^{CD3}$ with different CD3-binding domains having different affinities for CD3 were analysed regarding CD3 binding on CD3+-Jurkat cells, EGFRvIII-binding on $CHO^{EGFRvIII}$ cells as well as cytotoxic potency. CD3-binding $K_D$ values range from 1 nM to approx. 500 nM. EGFRvIII-binding $K_D$ values were and cytotoxic $EC_{50}$ values are plotted over the CD3-binding $K_D$ values for each of the analysed tandem diabodies. While the TandAbs show only little variability in the EGFRvIII-binding $K_D$ values, the cytotoxic $EC_{50}$ show an almost linear increase with increasing CD3-binding $K_D$ values of the tandem diabodies.
Figure 12A:
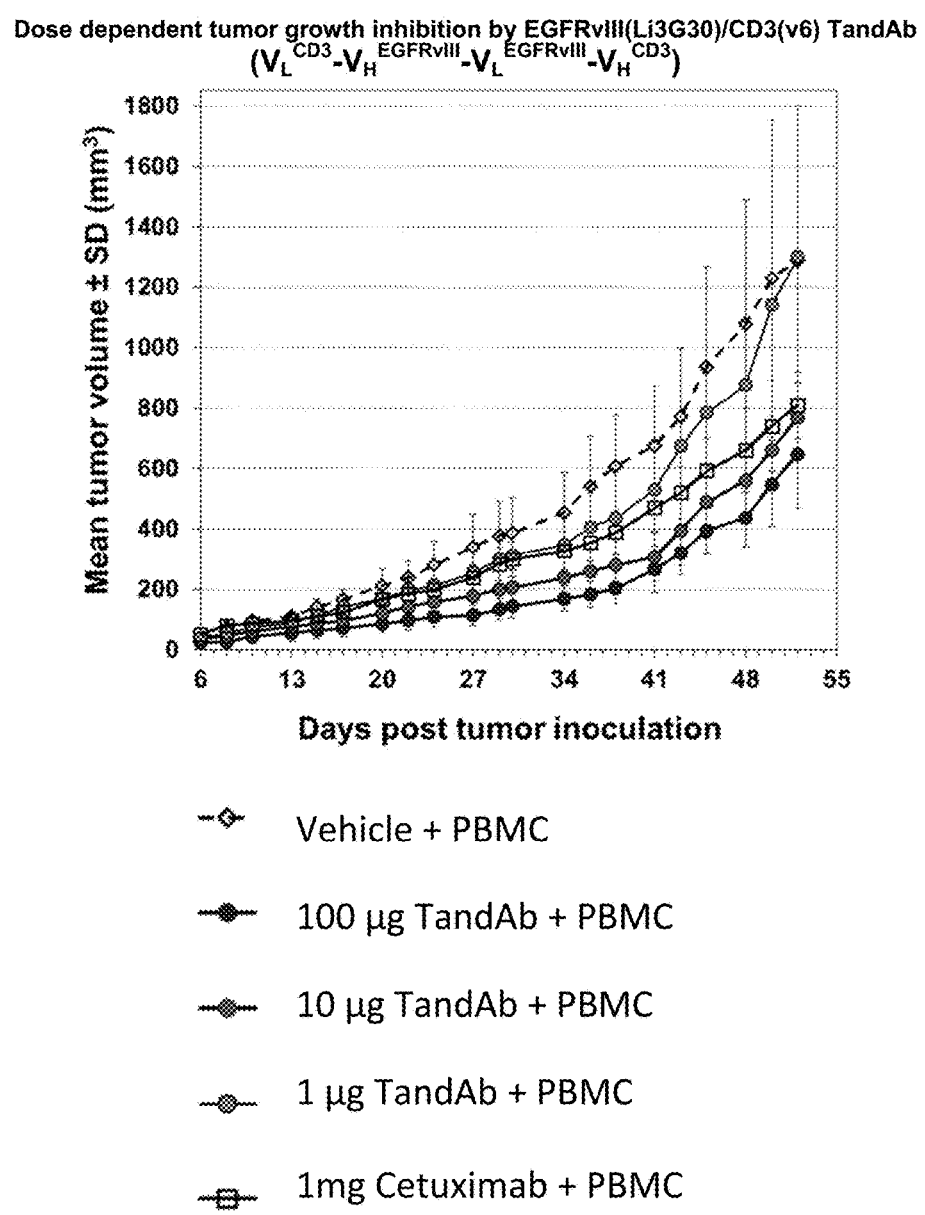
FIGS. 12A-12B show the results of an in vivo proof of concept study. The dose dependent inhibitory effect on the growth of subcutaneous $F98^{EGFRvIII}$ xenograft tumors was analysed for two EGFRvIII/CD3 tandem diabodies containing the same EGFRvIII-binding domain (Li3G30) but different CD3 binding domains or domain orders and compared to the effect of Cetuximab which was dosed at a much higher concentration level. (A) Dose dependent tumor growth inhibition by a EGFRvIII/$CD3^{v6}$ tandem diabodies having the domain order $V_L^{CD3}$-$V_H^{EGFRvIII}$-$V_L^{EGFRvIII}$-$V_H^{CD3}$; (B) Dose dependent tumor growth inhibition by a EGFRvIII/CD3 tandem diabodies containing a different high affinity CD3-binding domain and having the domain order $V_H^{EGFRvIII}$-$V_L^{CD3}$-$V_H^{CD3}$-$V_L^{EGFRvIII}$.
Figure 12B:
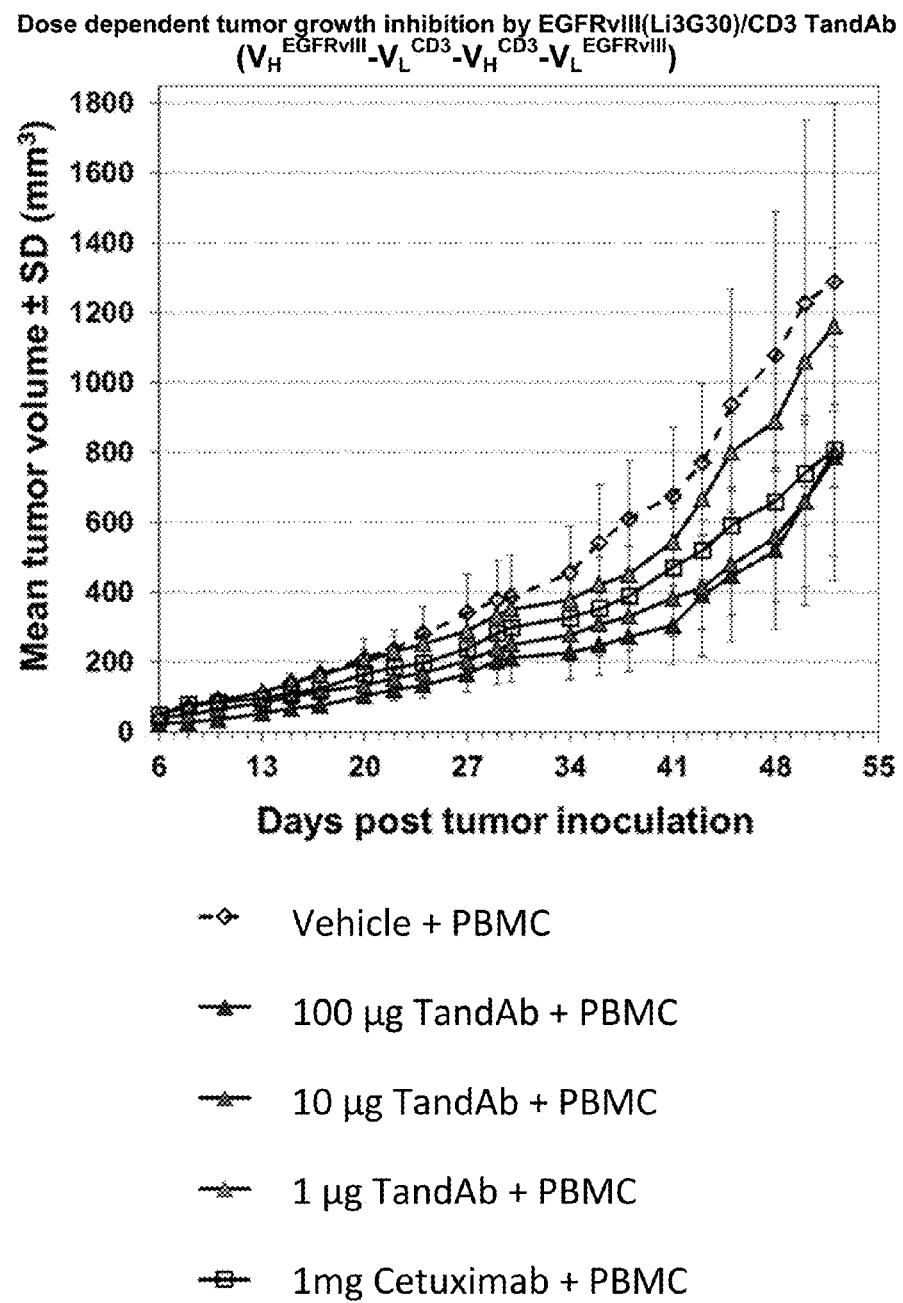

Tandem diabodies with CD3 binding $K_D$'s ranging from 1.1 nM to approximately 500 nM but relatively constant EGFRvIII binding $K_D$ (ranging from 2.0 nM to 6.7 nM) were generated and showed a good correlation of their CD3 binding strength and their cytotoxic potency towards EGFRvIII expressing cells with EC50 values ranging from 25 pM to approximately 10000 pM (FIG. 11).

Although the affinity to EGFRvIII of the antigen-binding proteins according to the invention has been significantly improved, there has been no loss of specificity.

TandAb® is a trademark of Affimed Therapeutics used for designating a tandem diabody. (Kipriyanov et al., 1999, J. Mol. Biol, 293:41-56; Cochlovius et al., 2000, Cancer Res., 60:4336-4341; Reusch et al., 2004, Int. J. Cancer, 112:509-518, Kipriyanov, 2009, Methods Mol Biol, 562:177-93; McAleese and Eser, 2012, Future Oncol. 8:687-95). In the context of the present invention TandAb and tandem diabodies are used as synonyms.

The sequences of the wild type EGFR gene and protein are known. The EGFRvIII is the result of an in-frame deletion of exons 2-7 (801 bp) of the wild type EGFR gene, resulting in the deletion of 267 amino acids in the external domain of the receptor, and the generation of a novel glycine residue at the junction of exons 1 and 8. This novel juxtaposition of amino acids within the extra-cellular domain of the EGFR creates a tumor specific and immunogenic epitope.

According to a first aspect of the invention, there is described a binding protein having specificity for at least EGFRvIII and is not cross-reactive with wild type EGFR. The binding protein preferably comprises CDR1, CDR2, CDR3 of an antibody variable heavy chain and CDR1, CDR2 and CDR3 of an antibody variable light chain selected from the CDRs described in Table 1A below.

TABLE 1A sequence identifier numbers of amino acid sequences of human light and heavy chain CDRs from binding proteins that specifically bind to EGFRvIII

| Clone | Chain | CDR1 | CDR2 | CDR3 |
|---|---|---|---|---|
| Li3G30 | VH | 27 | 28 | 29 |
|  | VL | 30 | 31 | 32 |
| 469 | VH | 33 | 28 | 29 |
|  | VL | 34 | 31 | 35 |
| 470 | VH | 33 | 28 | 29 |
|  | VL | 36 | 31 | 37 |
| 471 | VH | 33 | 38 | 29 |
|  | VL | 39 | 40 | 41 |
| 472 | VH | 42 | 43 | 29 |
|  | VL | 44 | 40 | 45 |
| 473 | VH | 46 | 28 | 29 |
|  | VL | 47 | 40 | 48 |
| 474 | VH | 49 | 50 | 29 |
|  | VL | 51 | 40 | 52 |

TABLE 1A-continued sequence identifier numbers of amino acid sequences of human light and heavy chain CDRs from binding proteins that specifically bind to EGFRvIII

| Clone | Chain | CDR1 | CDR2 | CDR3 |
|---|---|---|---|---|
| 475 | VH | 53 | 54 | 29 |
|  | VL | 44 | 40 | 55 |
| 476 | VH | 53 | 28 | 29 |
|  | VL | 56 | 57 | 58 |
| 477 | VH | 46 | 28 | 29 |
|  | VL | 59 | 40 | 60 |
| 478 | VH | 33 | 61 | 29 |
|  | VL | 44 | 40 | 62 |
| 479 | VH | 69 | 63 | 29 |
|  | VL | 64 | 31 | 65 |

Therefore, an embodiment of the invention is an EGFRvIII binding protein with at least one EGFRvIII binding site comprising an antibody variable heavy chain domain comprising a CDR1 selected from the group consisting of SEQ ID NOs: 27, 33, 42, 46, 49, 53; a CDR2 selected from the group consisting of SEQ ID NOs: 28, 38, 43, 50, 54, 61, 63; and a CDR3 of SEQ ID NO: 29, and/or an antibody variable light chain domain comprising a CDR1 selected from the group consisting of SEQ ID NOs: 30, 34, 36, 39, 44, 47, 51, 56, 59, 64; a CDR2 selected from the group consisting of SEQ ID NOs: 31, 40, 57, and a CDR3 selected from the group consisting of SEQ ID NOs: 32, 35, 37, 41, 45, 48, 52, 55, 58, 60, 62 and 65.

According to a further embodiment the binding protein comprises at least one EGFRvIII binding site having an antibody variable heavy chain domain selected from the group consisting of SEQ ID NOs: 1, 3, 5, 7, 9, 11, 13, 15, 17, 19, 21 and 25 as shown in Table 1B and/or an antibody variable light chain domain selected from the group consisting of SEQ ID NOs: 2, 4, 6, 8, 10, 12, 14, 16, 18, 20, 22 and 26 as shown in Table 1B. The amino acid sequences of the three variable light chain CDRs and three variable heavy chain CDRs are indicated in bold and underlined in Table 1. These binding sites show an improved affinity for EGFRvIII without a loss of specificity. These antigen-binding proteins are not cross-reactive with the wild type EGFR antigen.

Further, these antigen-binding proteins according to the invention show no or only minimal internalization of EGFRvIII upon binding thereto. According to the invention more than 80%, preferably more than 90%, most preferably more than 95% of the EGFRvIII receptor molecule still remains on the cell surface after the exposure of the cells to the EGFRvIII-binding antibodies, under the conditions tested according to Example 9. Instead of inducing internalization, binding of the EGFRvIII-specific binding proteins according to the invention might either inhibit internalization or facilitate increased expression of EGFRvIII leading to its increased cell surface density.

The term "binding protein" refers to an immunoglobulin derivative with antigen binding properties, i.e. immunoglobulin polypeptides or fragments thereof that contain an antigen binding site. The binding protein comprises variable domains of an antibody or fragments thereof. Each antigen-binding domain is formed by an antibody, i.e. immunoglobulin, variable heavy chain domain (VH) and an antibody variable light chain domain (VL) binding to the same epitope. A variable light chain domain or a variable heavy chain domain according to the invention is a polypeptide comprising CDR1, CDR2 and CDR3. Preferably, the binding protein according to the invention is devoid of immunoglobulin constant domains. The term "binding protein" refers also to antibody fragments or derivatives including Fab, Fab', F(ab')$_2$, Fv fragments, single-chain Fv, diabody, tandem diabody (TandAb®), flexibody (WO 03/025018), tandem single-chain Fv ((scFv)$_2$).

TABLE 1B amino acid sequences of all anti-EGFRvIII variable heavy chain domains (VH) and variable light chain domains (VL) (amino acid sequences of CDR1, CDR2 and CDR3 are indicated in bold and are underlined)

(Li3G30 VH)
SEQ ID NO: 25
EVQLVQSGAEVKKPGESLKISCKGSGYSFTSYWIGWVRQMPGKGLEWM
GIIYPGDSDTRYSPSFQGQVTISADKSISTAYLQWSSLKASDTAMYYC
ARLGSSWTNDAFDIWGQGTMVTVSS (Li3G30 VL)
SEQ ID NO: 26
SYELTQPPSVSVSPGQTARITCSGDALPKQYAYWYQQKPGQAPVLVIY
KDSERPSGIPERFSGSSSGTTVTLTISGVQAEDEADYYC**QSADSSGTP
LIV**FGTGTKLTVL (469 VH)
SEQ ID NO: 1
EVQLVQSGAEVKKPGESLKISCKGSGYSFNSYWIGWVRQMPGKGLEWM
GIIYPGDSDTRYSPSFQGQVTISADKSISTAYLQWSSLKASDTAMYYC
ARLGSSWTNDAFDIWGQGTLVTVSS (469 VL)
SEQ ID NO: 2
LTQPPSYESVSVSPGQTARITCSGDTLPKQYAYWYQQKPGQAPVLVIY
KDSERPSGIPERFSGSSSGTTVTLTISGVQAEDEADYYC**QSVDVSGTY
VV**FGGGTKLTVL (470 VH)
SEQ ID NO: 3
EVQLVQSGAEVKKPGESLKISCKGSGYSFNSYWIGWVRQMPGKGLEWM
GIIYPGDSDTRYSPSFQGQVTISADKSISTAYLQWSSLKASDTAMYYC
ARLGSSWTNDAFDIWGQGTLVTVSS (470 VL)
SEQ ID NO: 4
SYELTQPPSVSVSPGQTARITCSGDALDKQYAYWYQQKPGQAPVLVIY
KDSERPSGIPERFSGSSSGTTVTLTISGVQAEDEADYYC**QSVDSSETY
VV**FGGGTKLTVL (471 VH)
SEQ ID NO: 5
EVQLVQSGAEVKKPGESLKISCKGSGYSFNSYWIGWVRQMPGKGLEWM
GIIYPGDSANRYSPSFQGQVTISADKSISTAYLQWSSLKASDTAMYYC
ARLGSSWTNDAFDIWGQGTLVTVSS (471 VL)
SEQ ID NO: 6
SYELTQPPSVSVSPGQTARITCSGDYLPKQYAYVVYQQKPGQAPVLVI
YKDTERPSGIPERFSGSSSGTTVTLTISGVQAEDEADYYC**QSVDSSHP
SVV**FGGGTKLTVL (472 VH)
SEQ ID NO: 7
EVQLVQSGAEVKKPGESLKISCKGSGYSFGYYWIGWVRQMPGKGLEWM
GIIYPGDSHTRYSPSFQGQVTISADKSISTAYLQWSSLKASDTAMYYC
ARLGSSWTNDAFDIWGQGTLVTVSS (472 VL)
SEQ ID NO: 8
SYELTQPPSVSVSPGQTARITCSGDALPKQYAYWYQQKPGQAPVLVIY
KDTERPSGIPERFSGSSSGTTVTLTISGVQAEDEADYYC**QSVDSSGTQ
VV**FGGGTKLTVL (473 VH)
SEQ ID NO: 9
EVQLVQSGAEVKKPGESLKISCKGSGYSFSSYWIGWVRQMPGKGLEWM
GIIYPGDSDTRYSPSFQGQVTISADKSISTAYLQWSSLKASDTAMYYC
ARLGSSWTNDAFDIWGQGTLVTVSS

TABLE 1B-continued amino acid sequences of all anti-EGFRvIII variable
heavy chain domains (VH) and variable light chain
domains (VL) (amino acid sequences of CDR1, CDR2
and CDR3 are indicated in bold and are underlined)

(473 VL)
SEQ ID NO: 10
SYELTQPPSVSVSPGQTARITCSGHALPSQYAYWYQQKPGQAPVLVIY
KDTERPSGIPERFSGSSSGTTVTLTISGVQAEDEADYYC**QSVDSSGTS
VI**FGGGTKLTVL (474 VH)
SEQ ID NO: 11
EVQLVQSGAEVKKPGESLKISCKGSGYSFSHYWIGWVRQMPGKGLEWM
GITYPGDVDTRYDPSFQGQVTISADKSISTAYLQWSSLKASDTAMYYC
ARLGSSWTNDAFDIWGQGTLVTVSS (474 VL)
SEQ ID NO: 12
SYELTQPPSVSVSPGQTARITCSGDALPKTYAYWYQQKPGQAPVLVIY
KDTERPSGIPERFSGSSSGTTVTLTISGVQAEDEADYYC**QSADSSGTY
LV**FGGGTKLTVL (475 VH)
SEQ ID NO: 13
EVQLVQSGAEVKKPGESLKISCKGSGYSFTSYWIGWVRQMPGKGLEWM
GIIYPDDSDTRYSPSFQGQVTISADKSISTAYLQWSSLKASDTAMYYC
ARLGSSWTNDAFDIWGQGTLVTVSS (475 VL)
SEQ ID NO: 14
SYELTQPPSVSVSPGQTARITCSGDALPKQYAYWYQQKPGQAPVLVIY
KDTERPSGIPERFSGSSSGTTVTLTISGVQAEDEADYYC**QSVDSSGTY
YV**FGGGTKLTVL (476 VH)
SEQ ID NO: 15
EVQLVQSGAEVKKPGESLKISCKGSGYSFTSYWIGWVRQMPGKGLEWM
GIIYPGDSDTRYSPSFQGQVTISADKSISTAYLQWSSLKASDTAMYYC
ARLGSSWTNDAFDIWGQGTLVTVSS (476 VL)
SEQ ID NO: 16
SYELTQPPSVSVSPGQTARITCSGDNIPHQYAYWYQQKPGQAPVLVIY
KDTERPAGIPERFSGSSSGTTVTLTISGVQAEDEADYYC**QSADPTGAY
LV**FGGGTKLTVL (477 VH)
SEQ ID NO: 17
EVQLVQSGAEVKKPGESLKISCKGSGYSFSSYWIGWVRQMPGKGLEWM
GIIYPGDSDTRYSPSFQGQVTISADKSISTAYLQWSSLKASDTAMYYC
ARLGSSWTNDAFDIWGQGTLVTVSS (477 VL)
SEQ ID NO: 18
SYELTQPPSVSVSPGQTARITCSGDYLPKQYAYWYQQKPGQAPVLVIY
KDTERPSGIPERFSGSSSGTTVTLTISGVQAEDEADYYC**QSADASGTY
YV**FGGGTKLTVL (478 VH)
SEQ ID NO: 19
EVQLVQSGAEVKKPGESLKISCKGSGYSFNSYWIGWVRQMPGKGLEWM
GIIYPGDEDTRYSPSFQGQVTISADKSISTAYLQWSSLKASDTAMYYC
ARLGSSWTNDAFDIWGQGTLVTVSS (478 VL)
SEQ ID NO: 20
SYELTQPPSVSVSPGQTARITCSGDALPKQYAYWYQQKPGQAPVLVIY
KDTERPSGIPERFSGSSSGTTVTLTISGVQAEDEADYYC**QSVDPSGTY
YV**FGGGTKLTVL (479 VH)
SEQ ID NO: 21
QSGAEVKKPGEVQLVESLKISCKGSGYDFSSYWIGWVRQMPGKGLEWM
GIIYPGDSDTIYSPSFQGQVTISADKSISTAYLQWSSLKASDTAMYYC
ARLGSSWTNDAFDIWGQGTLVTVSS

TABLE 1B-continued amino acid sequences of all anti-EGFRvIII variable
heavy chain domains (VH) and variable light chain
domains (VL) (amino acid sequences of CDR1, CDR2
and CDR3 are indicated in bold and are underlined)

(479 VL)
SEQ ID NO: 22
SYELTQPPSVSVSPGQTARITCSGAALPEQYAYWYQQKPGQAPVLVIY
KDSERPSGIPERFSGSSSGTTVTLTISGVQAEDEADYYC**QSVDSSGTF
YV**FGGGTKLTVL

In a preferred embodiment the binding protein conferring specificity to EGFRvIII comprises an antigen binding site from one of the following combinations of a variable heavy chain domain and a variable light chain domain shown in Table 1:
(i) SEQ ID NO:1 and SEQ ID NO:2,
(ii) SEQ ID NO:3 and SEQ ID NO:4,
(iii) SEQ ID NO:5 and SEQ ID NO:6,
(iv) SEQ ID NO:7 and SEQ ID NO:8,
(v) SEQ ID NO:9 and SEQ ID NO: 10,
(vi) SEQ ID NO: 11 and SEQ ID NO: 12,
(vii) SEQ ID NO: 13 and SEQ ID NO: 14,
(viii) SEQ ID NO:15 and SEQ ID NO:16,
(ix) SEQ ID NO:17 and SEQ ID NO:18,
(x) SEQ ID NO:19 and SEQ ID NO:20,
(xi) SEQ ID NO:21 and SEQ ID NO:22, or
(xii) SEQ ID NO:25 and SEQ ID NO:26

The present invention also provides binding proteins that not only have specificity for EGFRvIII, but which also have at least one further functional domain. In a further embodiment at least one further functional domain is an effector domain. An "effector domain" is a binding site specific for an effector cell, which can stimulate or trigger cytotoxicity, phagocytosis, antigen presentation, cytokine release. Such effector cells are, for example but not limited to, T- or NK-cells. In particular, the further effector domain comprises at least one antibody variable heavy chain domain and at least one variable light chain domain forming an antigen binding site for CD3, preferably human CD3.

Thus, the EGFRvIII binding protein according to the invention may be multispecific. The term "multispecific" as used herein means that a binding protein of the invention has at least two antigen binding sites to different epitopes, wherein at least one is for EGFRvIII. For example, the binding protein may be trispecific and have binding sites to two different epitopes and/or antigens on a tumor cell and at least one binding site for an epitope or antigen on an effector cell, such as, for example CD3. The binding protein may have binding sites to different epitopes on the same antigen and/or epitopes on different antigens. Such multispecific binding proteins include single-chain diabodies, (scFv)$_2$, tandem diabodies (TandAb®), and flexibodies (see Le Gall et al. 1999 FEBS Letts 453:164-168 and WO 03/025018). In a particular embodiment of the invention, the binding protein is bispecific for EGFRvIII and CD3.

The CD3 binding site of the multispecific binding protein according to the invention may be composed of the variable heavy chain domain (SEQ ID NO: 23) and the variable light chain domain (SEQ ID NO: 24) as shown in Table 2 or a close homolog of this sequence differing in only 2 amino acids of the CDR sequences or any other fully human, humanized or not human variable antibody domains specific for CD3 (termed CD3), such as, for example, variable antibody domains of or any other fully human, humanized or not human variable antibody domains specific for CD3, in particular CD38, such as, for example, variable antibody domains of UCHT1 or OKT3.

TABLE 2 amino acid sequences of a fully human anti-CD3 variable heavy chain domain (VH) and variable light chain domain (VL) (amino acid sequences of CDR1, CDR2 and CDR3 are indicated in bold and are underlined)

aa sequence anti-CD3

SEQ ID NO: 23   EVQLVESGGGLVQPGGSLRLSCAASGFTFSTYAM
                NWVRQAPGKGLEWVGRIRSKYNNYATYYADSVKD
                RFTISRDDSKNSLYLQMNSLKTEDTAVYYCARHG
                NFGNSYVSYFAYWGQGTLVTVSS

SEQ ID NO: 24   DIQMTQSPSSLSASVGDRVTITCRSSTGAVTTSN
                YANWVQQKPGKAPKALIGGTNKRAPGVPSRFSGS
                LIGDKATLTISSLQPEDFATYYCALWYSNLWVFG
                QGTKVEIK

Furthermore, the EGFRvIII binding protein according to the invention may be multivalent. The term "multivalent" as used herein means that a binding protein according to the invention comprises at least two antigen binding sites. The antigen binding sites can have the same or different specificities. In an embodiment of the invention the binding protein binds with at least two binding sites, i.e. bivalently, to the same epitope. An example of a bivalent binding protein is a diabody and an example of an at least tetravalent binding protein is a tandem diabody.

In a further aspect of the invention the described EGFRvIII binding protein as well as the bispecific EGFRvIII and CD3 binding sites are humanized or fully human, i.e. of human origin.

In a further aspect of the invention the EGFRvIII binding protein or the multispecific EGFRvIII and CD3 binding protein is a dimer, i.e. comprises two polypeptides with antigen binding sites for EGFRvIII and CD3.

According to the invention a dimeric and bispecific EGFRvIII and CD3 binding protein is provided in the format of a tandem diabody (TandAb®). Such tandem diabodies are constructed by linking four antibody variable binding domains (heavy-chain variable domain (VH) and light-chain variable domains (VL) in a single gene construct (see McAleese and Eser, 2012, Future Oncol. 8:687-95) enabling homo-dimerization. In such tandem diabodies the linker length is such that it prevents intermolecular pairing of the variable domains so that the molecule cannot fold back upon itself to form a single-chain diabody, but rather is forced to pair with the complementary domains of another chain. The domains are also arranged such that the corresponding VH and VL domains pair during this dimerization. Following expression from a single gene construct, two identical polypeptide chains fold head-to-tail forming a functional non-covalent homodimer of approximately 110 kDa (McAleese and Eser, 2012, Future Oncol. 8:687-95). Despite the absence of intermolecular covalent bonds, the homodimer is highly stable once formed, remains intact and does not revert back to the monomeric form.

In one embodiment of multispecific tandem diabody, a humanized bispecific tetravalent antibody (TandAb®) is provided, with two binding sites each for CD3 and EGFRvIII (the EGFRvIII/CD3 RECRUIT-TandAb®) to harness the cytotoxic capacity of T cells for the treatment of glioblastoma (GB), prostate, head and neck, and other epidermal growth factor receptor mutant vIII positive (EGFRvIII+) cancers.

Tandem diabodies have a number of properties that provide advantages over traditional monoclonal antibodies and also smaller multispecific molecules. Tandem diabodies are fully functional in the absence of glycosylation. Tandem diabodies contain only antibody variable domains and therefore lack any of the side effects that may be associated with the Fc moiety. Because bispecific tandem diabodies allow for bivalent binding to each of EGFRvIII and CD3, the avidity is the same as that of an IgG. The size of a tandem diabody, of approximately 110 kDa is smaller than an IgG, which may allow for enhanced tumor penetration. However, this size is well above the renal threshold for first-pass clearance, offering a pharmacokinetic advantage compared with smaller bispecific formats based on antibody-binding domains or non-antibody scaffolds. The generation and production of such tandem diabodies is described, for example, in Kipriyanov S M: Methods Mol. Biol. 2009; 562:177-93 Kipriyanov S M: Methods Mol Biol 2003; 207:323-33 or McAleese and Eser, 2012, Future Oncol. 8:687-95.

Tandem diabodies are well expressed in CHO cells. A robust upstream and downstream manufacture process can be put in place.

The EGFRvIII and CD3 bispecific tandem diabody according to the invention is designed to allow specific targeting of EGFRvIII+ tumor cells by recruiting cytotoxic T cells. Antibodies are not capable of directly recruiting cytotoxic T cells. In contrast, by engaging CD3 molecules expressed specifically on these cells, the tandem diabody can crosslink cytotoxic T cells with EGFRvIII+ tumor cells in a highly specific fashion, thereby significantly increasing the cytotoxic potential of such molecules. The tandem diabody displays strong, specific and efficient cytotoxicity. There is significant evidence that T cells can play a role in controlling tumor growth. For example the presence of cytotoxic T cells in colorectal tumors as well as lymph nodes from NHL patients was shown to correlate with a better clinical outcome. Furthermore, the potential of therapies designed to induce T-cell responses has been demonstrated for melanoma vaccines, as well as the antibody directed against CTLA-4, a negative regulator of T-cell activation. The tandem diabody according to the invention engages cytotoxic T cells via binding to the surface-expressed CD3, preferably CD3ε, which forms part of the T-cell receptor. Simultaneous binding of this tandem diabody to CD3 and to EGFRvIII expressed on the surface of particular tumor cells causes T-cell activation and mediates the subsequent lysis of the tumor cell.

"Dimer" refers to a complex of two polypeptides. Preferably, the two polypeptides are non-covalently associated with each other, in particular with the proviso that there is no covalent bond between the two polypeptides. Preferably, the bispecific dimer is homodimeric, i.e. comprises two identical polypeptides. However, trispecific or other multispecific dimers may be heterodimeric and comprise two different polypeptides, e.g., wherein of at least one binding site the variable light chain domain is located on one polypeptide and the variable heavy chain domain is located on the other domain. The term "polypeptide" refers to a polymer of amino acid residues linked by amide bonds. The polypeptide is, preferably, a single chain fusion protein which is not branched. In the polypeptide, the variable antibody domains are linked one after another. The polypeptide may have contiguous amino acid residues in addition to the variable domain N-terminal and/or C-terminal. For example, such contiguous amino acid residues may comprise a Tag sequence, preferably at the C-terminus which might be useful for the purification of the polypeptide.

Each polypeptide of the bispecific tandem diabody comprises at least four variable domains, a variable light chain (VL) and a variable heavy chain (VH) of a CD3 binding protein as well as a variable light chain (VL) and a variable heavy chain (VH) of an EGFRvIII binding protein. The four variable domains are linked by peptide linkers L1, L2 and L3 and may be arranged from the N- to the C-terminus as follows:
(i) VL (CD3)-L1-VH (EGFRvIII)-L2-VL(EGFRvIII)-L3-VH(CD3); or
(ii) VH (CD3)-L1-VL(EGFRvIII)-L2-VH(EGFRvIII)-L3-VL(CD3); or
(iii) VL(EGFRvIII)-L1-VH(CD3)-L2-VL(CD3)-L3-VH (EGFRvIII); or
(iv) VH(EGFRvIII)-L1-VL(CD3)-L2-VH(CD3)-L3-VL (EGFRvIII).

Figure 5A:
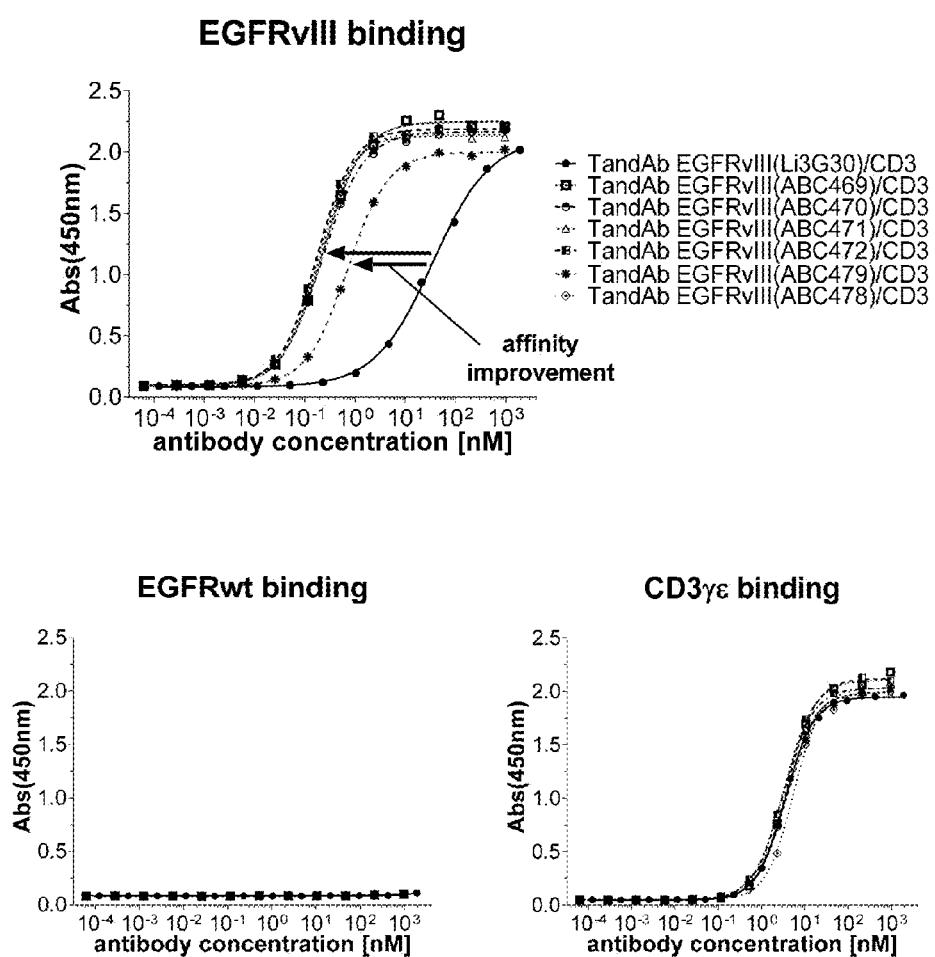
Figure 5C:
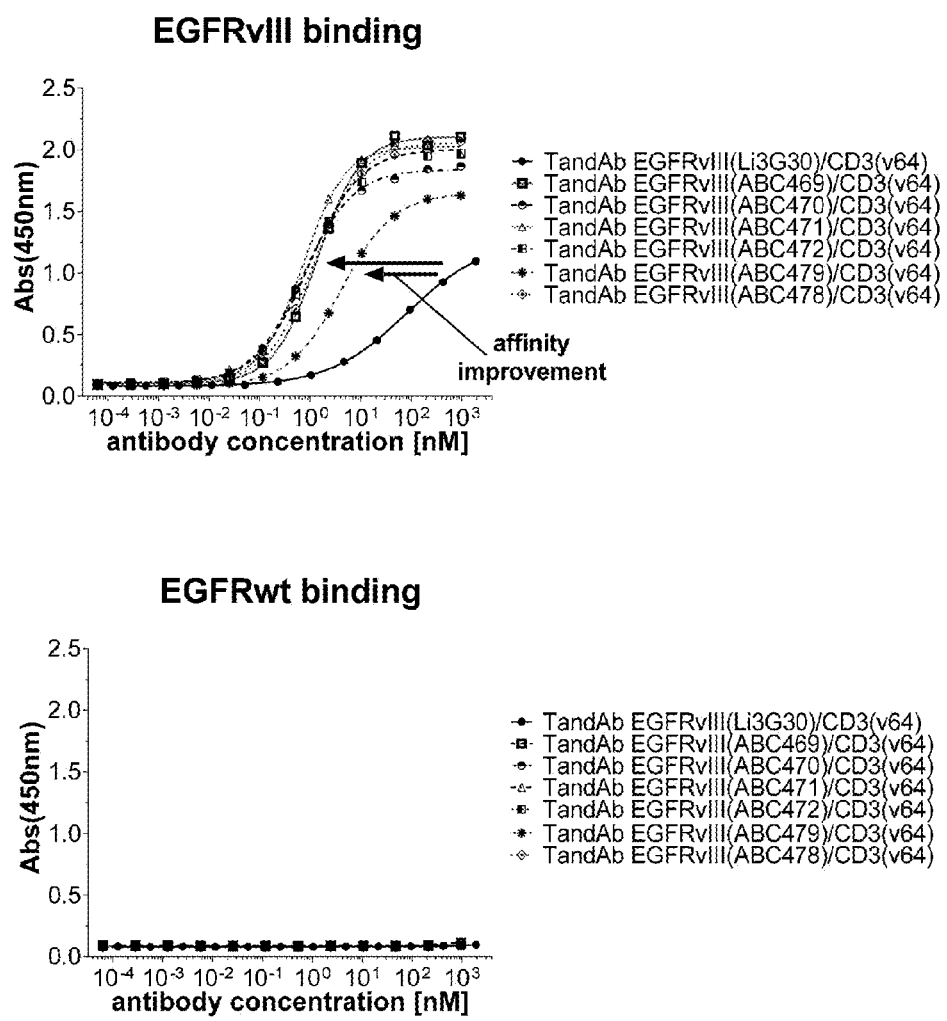
Figure 6A:
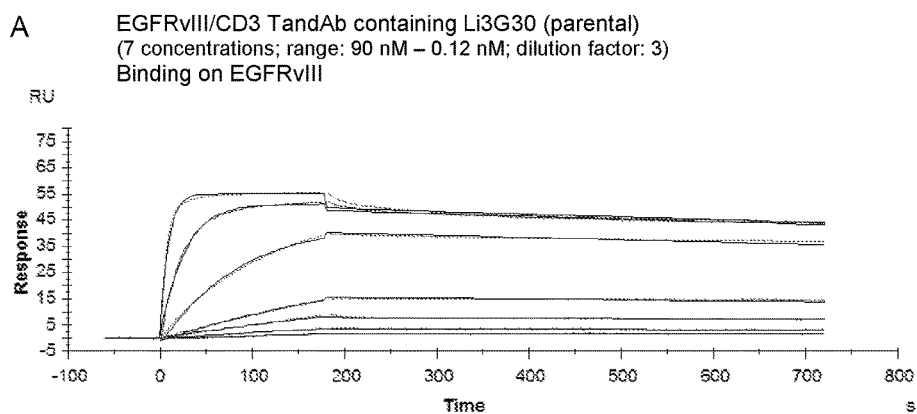
FIGS. 6A-6G show results from the multi-cycle kinetics measurement of EGFRvIII/CD3 specific tandem diabodies containing different bivalent EGFRvIII binding domains in the domain order $V_L^{CD3}$-$V_H^{EGFRvIII}$-$V_L^{EGFRvIII}$-$V_H^{CD3}$ to recombinant EGFRvIII-Fc antigen in Biacore X100. Sensograms show the kinetics of Surface plasmon resonance (SPR) response units (RU) measured over time at different concentration levels of the tandem diabodies. Association is measured for 180 seconds, dissociation is measured thereafter. Data is analysed using a 1:1 binding model.
Figure 6B:
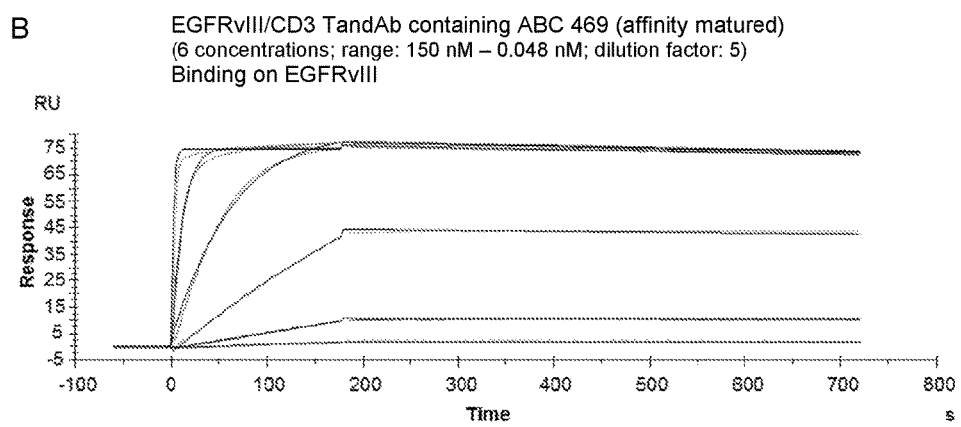
Figure 6C:
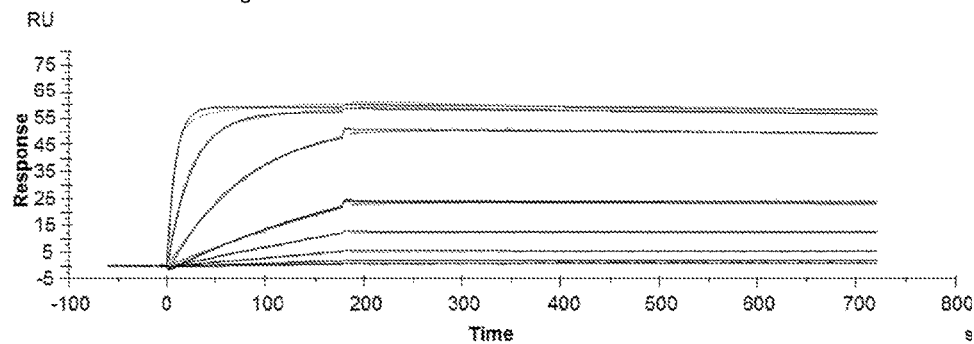
Figure 6D:
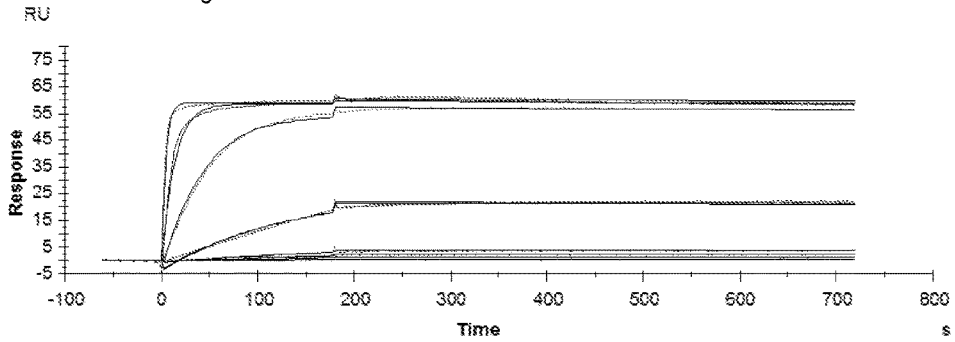
Figure 6E:
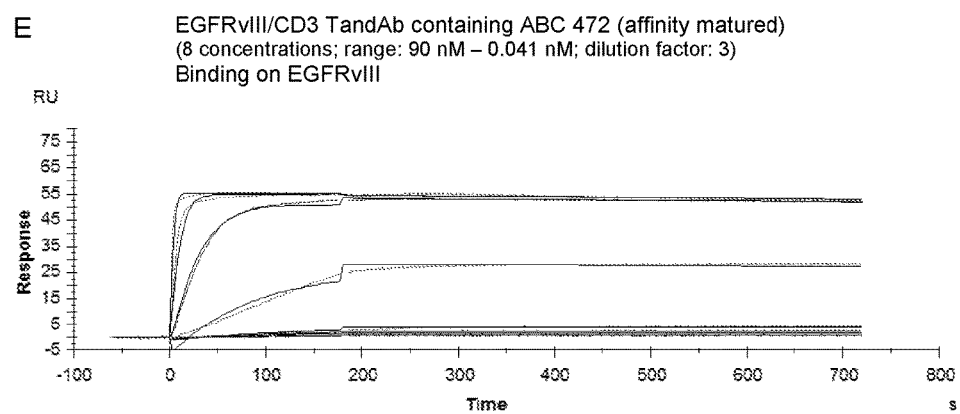
Figure 6F:
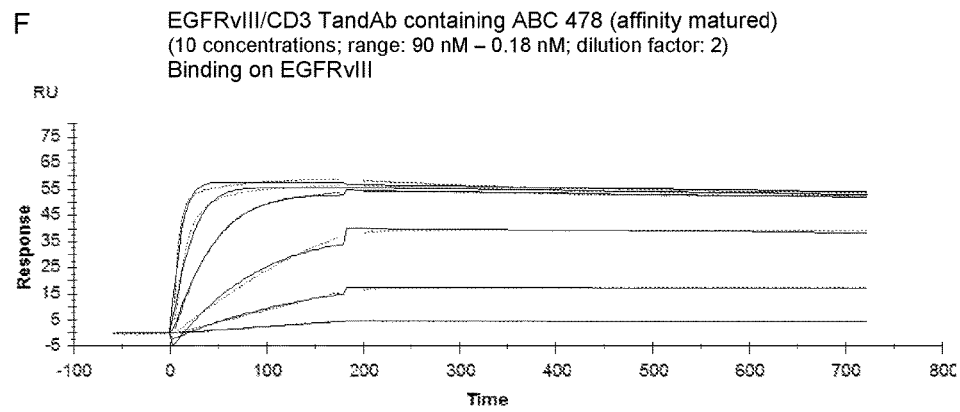
Figure 6G:
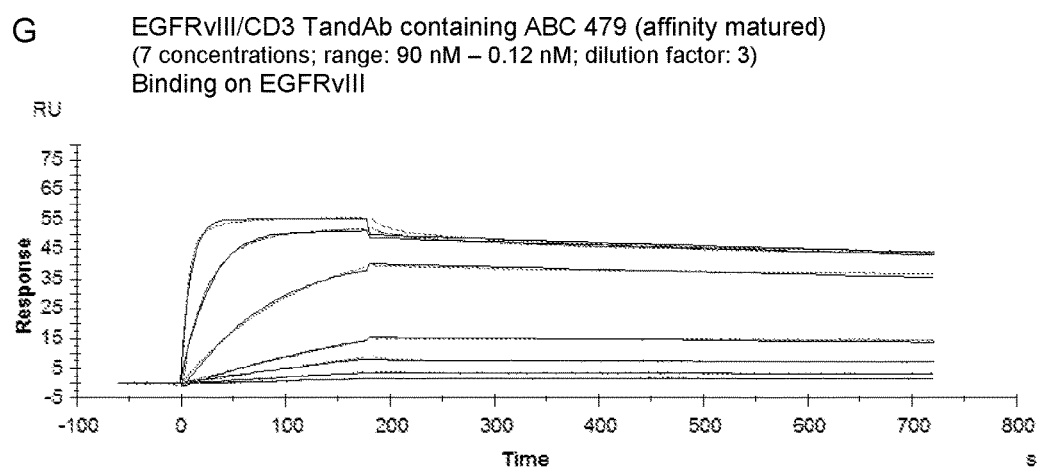

In an embodiment of the invention the four variable domains are arranged as VL (CD3)-L1-VH (EGFRvIII)-L2-VL(EGFRvIII)-L3-VH(CD3). Tandem diabodies with the domain order $V_L^{CD3}$-$V_H^{EGFRvIII}$-$V_L^{EGFRvIII}$-$V_H^{CD3}$ and containing different EGFRvIII binding sequences despite having different affinities for EGFRvIII all showed very similar binding to the second specificity, CD3, as shown by ELISA on CD3γε antigen (FIG. 5A). In the other tandem diabody domain order ($V_H^{EGFRvIII}$-$V_L^{CD3}$-$V_H^{CD3}$-$V_L^{EGFRvIII}$) containing the EGFRvIII binding domains in the outer position and the two CD3 binding sites in the middle, the substantial improvement in EGFRvIII binding with affinity matured EGFRvIII binding domains is similarly apparent, whereas the binding to CD3 of the domains in the middle of the tandem diabodies is slightly weaker and more variable between individual Tandem diabodies than in the first domain order (FIG. 5B). Similar observations were made when a different CD3 domain (SEQ ID NOs:23 and 24) was used to construct tandem diabodies containing the different EGFRvIII-binding domains (FIG. 5C).

The length of the linkers influences the flexibility of the antigen-binding tandem diabody. The effect of linker length on the formation of dimeric antigen-binding proteins is described, for example, in Todorovska et al., 2001 Journal of Immunological Methods 248:47-66; Perisic et al., 1994 Structure 2:1217-1226; Le Gall et al., 2004, Protein Engineering 17:357-366 and WO 94/13804.

According to the invention it is preferred that the length of the peptide linkers L1, L2 and L3 is such that the domains of one polypeptide can associate intermolecularly with the domains of another polypeptide to form the dimeric antigen-binding tandem diabody. Such linkers are "short", i.e. consist of 0, 1, 2, 3, 4, 5, 6, 7, 8, 9, 10, 11 or 12 amino acid residues. Thus, the linkers consist of about 12 or less amino acid residues. In the case of 0 amino acid residues the linker is a peptide bond. Such short linkers favor the intermolecular dimerization of the two polypeptides by binding and forming correct antigen-binding sites between antibody variable light chain domains and antibody variable heavy chain domains of different polypeptides. A short linker of about 12 amino acid residues or less generally prevents adjacent domains of the same polypeptide chain from intramolecular interaction with each other. In one embodiment of the invention these linkers consist of about 3 to about 10, for example 4, 5 or 6 contiguous amino acid residues.

Regarding the amino acid composition of the linkers, peptides are selected that do not interfere with the dimerization of the two polypeptides. For example, linkers comprising glycine and serine residues generally provide protease resistance. The amino acid sequence of the linkers can be optimized, for example, by phage-display methods to improve the antigen binding and production yield of the antigen-binding polypeptide dimer. Examples of peptide linkers suitable for a tandem diabody according to the invention are GGSGGS (SEQ ID NO:66), GGSG (SEQ ID NO:67) or GGSGG (SEQ ID NO:68).

The EGFRvIII binding protein and the multispecific tandem diabody described herein may be produced by expressing polynucleotides encoding the polypeptide of the tandem diabody which associates with another identical polypeptide to form the antigen-binding tandem diabody. Therefore, a further embodiment of the invention is a polynucleotide, e.g. DNA or RNA, encoding the polypeptide of the antigen-binding tandem diabody as described herein.

The polynucleotide may be constructed by methods known to the skilled person, e.g. by combining the genes encoding at least four antibody variable domains either separated by sequences encoding peptide linkers or directly linked by a peptide bond, into a single genetic construct operably linked to a suitable promoter, and optionally a protein-tag for detection and purification as well as a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

The polynucleotide may be inserted into a vector, preferably an expression vector, which represents a further embodiment of the invention. This recombinant vector can be constructed according to methods well known to the person skilled in the art.

A variety of expression vector/host systems may be utilized to contain and express the polynucleotide encoding the polypeptide of the present invention. Examples for expression vectors for expression in *E. coli* is pSKK (Le Gall et al., J Immunol Methods. (2004) 285(1): 111-27) or pcDNA5 (Invitrogen) for the expression in mammalian cells.

Thus, the antigen-binding tandem diabody as described herein may be produced by introducing a vector encoding the polypeptide as described above into a host cell and culturing said cell under conditions whereby the polypeptide chains are expressed, may be isolated from the culture media and, optionally, thereafter purified.

In a further embodiment the invention provides a pharmaceutical composition comprising the EGFRvIII binding protein, the antigen-binding tandem diabody, the vector comprising the polynucleotide encoding the polypeptide of the antigen binding tandem diabody or a host cell transformed by this vector and at least one pharmaceutically acceptable carrier. The term "pharmaceutically acceptable carrier" is meant to encompass any carrier, which does not interfere with the effectiveness of the biological activity of the ingredients and that is not toxic to the patient to whom it is administered. Examples of suitable pharmaceutical carriers are well known in the art and include normal saline solutions, phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents.

Prevention of the action of microorganisms may be ensured by the inclusion of various antibacterial and antifungal agents.

A skilled person will readily be able without undue burden to construct and obtain the antigen-binding proteins like tandem diabodies described herein by utilizing established techniques and standard methods known in the art, see for example Sambrook, Molecular Cloning A Laboratory Manual, Cold Spring Harbor Laboratory (1989) N.Y.; The Protein Protocols Handbook, edited by John M. Walker, Humana Press Inc. (2002); or Antibody engineering: methods and protocols/edited by Benny K. C. Lo; Benny K. C. II Series: Methods in molecular biology (Totowa, N.J.)).

The invention is further illustrated, but not limited thereto, by the following examples.

EXAMPLES

Example 1: Discovery and Affinity Maturation of EGFRvIII Specific Binding Proteins Discovery of Li3G30:

The Phage Display library of human scFv sequences of the IgM-based origin was subjected to two to three panning rounds to enrich binders that are specific for EGFRvIII. The library was preincubated on EGFR-Fc prior to every panning round to deplete binders to the wild type form of EGFR or to the Fc part of the fusion protein. The selection was done in parallel on solid phase coated EGFRvIII and in solution. After two and three panning rounds, single colonies were picked, expression of soluble scFv was induced and the extracts were screened for binding to EGFRvIII-Fc and EGFR-Fc.

According to this invention, fully human, highly specific variable antibody domains binding to EGFRvIII, a deletion mutant of the EGFR, which in the mutated form is exclusively expressed in tumors, but not on healthy tissues, are described. Fully human EGFRvIII specific domains described herein were initially discovered in a phage display screen using a fully human scFv library of the IgM-based origin. Surprisingly, despite using a depletion procedure on wild type EGFR antigen for two or three panning rounds, which should enrich binders that are specific for EGFRvIII, the majority of resulting scFv bound to both proteins (EGFRvIII and wild type EGFR) in ELISA. One highly EGFRvIII-specific sequence, entitled Li3G30, was identified. Besides few deviations at the N-terminus of VH and VL, the framework regions as well as CDR1 and 2 of heavy and light chain are completely identical to the germline encoded sequences VH5-51 and VL3-25, respectively. Li3G30 was identified from the third liquid phase panning round.

Affinity Maturation:

A library for the antibody framework pair VH5-51/VL3-25 was designed by an algorithm ordered from Distributed-Bio. Specificity determining residues from Li3G30 were identified and included into the library design. The design included 52 randomized CDR positions, each with an individually defined distribution of amino acids. Three different loop lengths were built into VL CDR3. Gene fragments encoding the randomized positions of VH and VL were ordered from Geneart/Lifetechnologies, and synthesized via TRIM-technology. The fragments were cloned into the phage display vector pEXHAM (Schwarz et al. 2004), reaching a final library size of 3.7E+8 transformed E. coli cells. The library was packaged in phage particles, and subjected to a panning and screening procedure to isolate variants with improved affinities and retained specificity for EGFRvIII. The panning was done with EGFRvIII-Fc antigen which was immobilized on a protein binding plastic surface. The panning procedure was designed to favour EGFRvIII binding scFvs with slow dissociation rates ($k_{OFF}$) by performing the following steps: the washing procedure included several washing buffer incubation steps up to 30 min in duration to favour the selection of slowly dissociating scFvs. Another procedure was based on an overnight competition with soluble EGFRvIII. To assure that no EGFR-EGFRvIII cross-reacting antibodies or antibodies binding to the Fc were selected in the process of affinity maturation prior to the first panning step the library was depleted of possible wild type EGFR binders by pre-incubation on wild type EGFR-Fc. Moreover, the screening protocol disfavoured cross-reactive binders due to the presence of soluble EGFR in the course of the panning procedure on immobilized EGFRvIII.

Unique EGFRvIII-specific scFv were further tested for binding to EGFRvIII-expressing transfected CHO and F98 cells in flow cytometry. ScFv which showed binding to wild type EGFR-expressing and/or untransfected cells were excluded from further analyses. An initial $K_D$ ranking in a Biacore X100 was used to identify the scFv with improved affinities to EGFRvIII compared to the starting clone Li3G30. The best variants were characterized in detailed SPR measurements and fluorescence-based stability assays.

The initial library for affinity maturation included three different loop lengths for VL CDR3, all of which were known to be compatible with the VH5-51/VL3-25 frameworks. Surprisingly, the middle loop length was clearly favoured during the selection. As a consequence the VL CDR3 is shortened by one amino acid compared to the parent anti-EGFRvIII antibody for all affinity-matured variants (Table 1, FIG. 1). The sequences of selected scFv were compared to the input library, and the analysis suggests three beneficial mutations in VL CDR3. The CDR1 and 2 of heavy and light chain of the parent anti-EGFRvIII antibody are identical to the sequence encoded by the respective germline sequences VH5-51 and VL3-25. The respective germline encoded residue was reconstituted or clearly favoured in 75% of the positions. One beneficial mutation is suggested in VH CDR1, and one in VL CDR1 (FIG. 1). The amino acid distribution in the remaining randomized positions was very close to the distribution in the library prior to selection.

Example 2: Measurement of scFv Binding to EGFRvIII and Wild Type EGFR in Biacore Preparation of Anti-Hu Fc IgG CM5-Chip:

Anti-hu Fc IgG CM5-chip was prepared by covalent amine coupling by using the Amine-Coupling-Kit (GE), according to the instructions of the manufacturer. The IgG was diluted in the provided immobilization buffer (10 mM sodium acetate, pH 5.0) to a concentration of 25 µg/ml. For the coupling procedure, the predefined method "Amine" of the Biacore T200 control software was applied. A target level between 5000-10000 RU for all 4 flow cells was reached. The surface of the chip was activated with EDC/NHS before injecting the recombinant protein solutions. Free binding sites on the surface were blocked with ethanolamine. 1×HBS-P+ was selected as a running buffer for the entire coupling procedure.

Concentration Range of the Single Chain Fv's (scFvs) Used in the SPR Measurement:

ScFv concentrations were checked before SPR measurement by A280 determination using Nandrop. The concentration in the stock solution (c) was calculated according to the equation:

$$c[mg/ml] = (A280)/(2.25\ [cm2/mg] \times 1\ [cm])$$

The different extinction coefficients were calculated with the 'Expasy Protparam' prediction tool (web.expasy.org/protparam/). For calculation of the molar concentration of His-tagged scFv antibodies, a molecular weight of approx. 28 kD was assumed. The scFvs were adjusted to the final concentrations mentioned below by serial dilution in 1×HBS-P+ buffer. The following concentrations were prepared: 430 nM, 86 nM, 17.2 nM, 3.44 nM, 0.688 nM and 0 nM.

Conditions of Measurement for the scFvs:

EGFRvIII-Fc and wild type EGFR-Fc fusion-proteins were diluted in 1×HBS-P+ to a concentration of 6.25 nM. Both antigens were injected at a flow rate of 10 μl/min for 75 sec for EGFRvIII-Fc and 90 sec for wild type EGFR-Fc. EGFRvIII-Fc was injected over flowcell 2 and wild type EGFR-Fc was injected over flowcell 4. Flowcell 1 and 3 were blanks. 1×HBS-P+ was used as running buffer for the entire procedure. The scFv antibodies were injected at a flow rate of 30 μL/min for 180 sec over all four flowcells. Signals measured in the flowcell 1 without captured antigen were subtracted from signals in the flowcell 2 to correct the binding curves for background binding. Signals measured in the flowcell 3 without captured antigen were subtracted from signals in the flowcell 4 to correct the binding curves for background binding. After 540 sec dissociation time the chip was regenerated as described below.

The anti-hu Fc IgG Chip was regenerated by injection of high salt buffer 3.0 M $MgCl_2$ (30 sec, 10 μL/min). Prior to each measurement, four "start-up cycles" were performed without scFv. ScFv solutions were measured from lowest to highest concentration. One cycle with neat running buffer (0 μM) was included.

The Kinetics of scFv antibodies were determined in MCK (Multi Cycle Kinetic) measurements. For estimation of apparent binding affinities the binding curves were evaluated using the "Kinetic" method included in the Biacore evaluation software. By this method the binding curves are globally fitted by the software using the "Langmuir 1:1 interaction model". The results are shown in Table 3.

The applied affinity maturation screening procedure was aimed at improving the EGFRvIII binding affinity of the EGFRvIII-specific binding domains by facilitating the selection of binders with reduced dissociation rate ($k_{OFF}$). However, surprisingly, the resulting affinity matured binders (Table 3) displayed substantially increased association rates ($k_{ON}$), whereas the reduction of $k_{OFF}$ had only a minor contribution to the up to 100-fold improved binding of the scFvs, with some binders exhibiting $K_D$ below 100 pM (Table 3). It is especially surprising that the reduction in the $K_D$ was achieved predominantly due to the increase in the $k_{ON}$ though the screening procedure favoured the selection of scFvs with reduced $k_{OFF}$. This is also surprising since affinity maturation of antibodies is usually associated with the reduction of $k_{OFF}$ (Schier et al., 1996, Pini et al., 1998, Boder et al., 2000).

TABLE 3

Summary of binding affinities of scFv ("VH" is variable heavy chain domain of scFv and "VL" is variable light chain domain of scFv). $K_D$ values, association rate ($k_{ON}$) and dissociation rate ($k_{OFF}$) measured for the different EGFRvIII binding domains in the scFv format to recombinant EGFRvIII-Fc antigen in Biacore (SPR) 1:1 binding model; "improvement factor" refers to fold-change relative to the parental scFv, Li3G30 (VH SEQ ID NO: 25 and VL SEQ ID NO: 26).

| | | EGFRvIII binding | | | | | | Wild type EGFR Binding |
|---|---|---|---|---|---|---|---|---|
| | | Affinity | | association rate | | dissociation rate | | |
| | | $K_D$ [nM] | improvement factor | $k_{ON}$ [1/Ms] | improvement factor | $k_{OFF}$ [1/s] | improvement factor | |
| 469 | VH SEQ ID NO: 1 VL SEQ ID NO: 2 | 0.72 | 10.8 | 8.3E+5 | 5.2 | 6.0E−4 | 2.0 | No |
| 470 | VH SEQ ID NO: 3 VL SEQ ID NO: 4 | 1.18 | 6.6 | 4.3E+5 | 2.7 | 5.0E−4 | 2.4 | No |
| 471 | VH SEQ ID NO: 5 VL SEQ ID NO: 6 | 0.26 | 29.9 | 1.1E+6 | 6.9 | 2.9E−4 | 4.1 | No |
| 472 | VH SEQ ID NO: 7 VL SEQ ID NO: 8 | 0.08 | 96.3 | 3.8E+6 | 23.8 | 3.0E−4 | 4.0 | No |
| 473 | VH SEQ ID NO: 9 VL SEQ ID NO: 10 | 0.67 | 11.6 | 1.2E+6 | 7.5 | 8.0E−4 | 1.5 | No |
| 474 | VH SEQ ID NO: 11 VL SEQ ID NO: 12 | 0.48 | 16.3 | 3.3E+6 | 20.6 | 1.6E−3 | 0.8 | No |
| 475 | VH SEQ ID NO: 13 VL SEQ ID NO: 14 | 0.70 | 11.1 | 1.2E+6 | 7.5 | 8.0E−4 | 1.5 | No |
| 476 | VH SEQ ID NO: 15 VL SEQ ID NO: 16 | 1.56 | 5.0 | 6.9E+5 | 4.3 | 1.1E−3 | 1.1 | No |
| 477 | VH SEQ ID NO: 17 VL SEQ ID NO: 18 | 1.30 | 6.0 | 3.0E+6 | 18.8 | 3.8E−3 | 0.3 | No |
| 478 | VH SEQ ID NO: 19 VL SEQ ID NO: 20 | 0.16 | 49.6 | 1.4E+6 | 8.8 | 2.3E−4 | 5.2 | No |
| 479 | VH SEQ ID NO: 21 VL SEQ ID NO: 22 | 2.54 | 3.1 | 3.8E+5 | 2.4 | 9.6E−4 | 1.3 | No |

Eight of 11 affinity matured scFv showed at least 5-fold improvement in the $k_{ON}$ compared to the parental scFv; three of them had a 20-fold higher $k_{ON}$. Compared to the improvement of the $k_{ON}$, the effects of affinity maturation on the $k_{OFF}$ were rather minor. Only three affinity-matured scFv demonstrated 4-5-fold improved $k_{OFF}$. Interestingly, two of them have been isolated from a selection approach with competition, which might be a more efficient method of selection for scFv with reduced $k_{OFF}$ compared to prolonged incubations in the wash buffer. Melting temperatures of the selected affinity matured candidates have a mean value of 62.2° C. as determined by differential scanning fluorimetry (DSF), ranging from 53° C. to 67.2° C.

Maintenance of High Specificity for EGFRvIII Vs Wild Type EGFR During Affinity Maturation Affinity maturation in general is frequently accompanied by small changes of the binding epitope, which may affect specificity/cross-reactivity (Barbas et al, 1994, Parsons et al., 1996, Winkler et al., 2000). The EGFRvIII neo-epitope relative to wild type EGFR is formed due to the in-frame deletion of 269 amino acid of the extra-cellular domain of wild type EGFR (exons 2-7), and is expected to be rather small: it consists of the novel juxtaposition of amino acids (amino acid 5 is fused to amino acid 274) and a single novel GLY amino acid at the deletion site. Even small changes in the binding epitope in this case are expected to quickly destroy the exquisite specificity for EGFRvIII and may result in cross-reactive binders which also recognize native EGFR.

Surprisingly, affinity maturation described herein resulted in up to 100-fold improved binding of anti-EGFRvIII antibodies without any such loss of exclusive specificity for EGFRvIII (Table 3, FIG. 2).

During the selection of affinity matured binders, unique EGFRvIII-specific scFv were tested for binding to EGFRvIII-expressing CHO (CHO$^{EGFRvIII}$) and F98 cells (F98$^{EGFRvIII}$) in flow cytometry as well as to human wild type EGFR expressing CHO (CHO$^{EGFR}$) and F98 (F98$^{EGFR}$) cells, and untransfected CHO and F98 cells.

11 highly specific anti-EGFRvIII scFv without any measurable background binding on wild type EGFR-positive cells (CHO$^{EGFR}$) or untransfected CHO cells were characterized in more detail. In the best case affinity of 80 pM for EGFRvIII antigen was measured, corresponding to an improvement factor of 100-fold compared to the parental scFv (Table 3). At the same time, none of the tested anti-EGFRvIII scFvs displayed any cross-reactivity with the wild type EGFR antigen (FIG. 2).

To the best of our knowledge, such high affinity for EGFRvIII of a human antibody domain combined with an exclusive specificity for EGFRvIII and without measurable cross-reactivity with the wild type EGFR has never been observed before. Safdari and colleagues recently described the results of the humanization of a murine, EGFRvIII-binding antibody domain, MR1 (Safdari et al., 2014), which in its murine form was firstly described by Lorimer and colleagues (Lorimer et al., 1996, Beers et al., 2000, Kuan et al., 2000). During the humanization approach they achieved an affinity improvement for humMR1 reaching similar picomolar $K_D$ values as reported here, however, in contrast to our invention, they fail to completely abolish cross-reactivity of the antibody domain with wild-type EGFR, which can be clearly seen in FIG. 4 of their publication (Safdari et al., 2014). Therefore, humMR1 is not fully specific for EGFRvIII (145 kD) but also recognizes EGFR (170 kD) after SDS PAGE and Western blot (Safdari et al., 2014). We extensively tested specificity and cross-reactivity of our EGFRvIII-binding domains, both, before and after the affinity maturation, and surprisingly found no signs of cross-reactivity with the wild type EGFR, either with purified recombinant wild type EGFR-antigen analysed in Biacore (FIG. 2), or in SDS PAGE and Western blotting (FIG. 4), or in ELISA (FIG. 5). Our EGFRvIII-binding domains also did not display any cross-reactivity with wild type EGFR overexpressed on the cell surface of transfected CHO cells (CHO$^{EGFR}$) or F98 glioma cells (F98$^{EGFR}$) (FIG. 3).

Example 3: Assessment by Flow Cytometry of Highly Specific and High Affinity EGFRvIII-Specific scFv Antibodies to F98 Rat Glioma Cells Overexpressing EGFRvIII (F98$^{EGFRvIII}$) or Stably Transfected CHO Cells Overexpressing EGFRvIII (CHO$^{EGFRvIII}$); Absence of Binding to F98 Cells Overexpressing Native EGFR (F98$^{EGFR}$) or Untransfected F98 Cells (F98), as Well as Absence of Binding to CHO Cells Overexpressing Native EGFR (CHO$^{EGFR}$) or Untransfected CHO Cells (CHO)

Material (Media, Buffer and Reagents):
Anti-His IgG 13/45/31 (Dianova), FCS (Invitrogen), Ficoll Paque PLUS (GE Healthcare), FITC-conj. goat anti-human IgG (Dianova), FITC-conj. goat anti-mouse IgG, minx(Dianova), L-Glutamine (Invitrogen), NaN$_3$ (Carl Roth), PBS (Invitrogen), Penicillin/Streptomycin (Invitrogen), Propidium iodide (Sigma), RPMI-1640 (Invitrogen)

Cells and cell lines:
F98 rat glioma cells, F98 cells overexpressing EGFR (F98$^{EGFR}$), as well as F98 cells overexpressing EGFRvIII (F98$^{EGFRvIII}$), were purchased from the American type culture collection (ATCC) and cultured according to the recommended protocols.
F98 (ATCC CRL-2397)
F98$^{EGFR}$ (ATCC CRL-2948)
F98$^{npEGFRvIII}$ (ATCC CRL-2949)

Stably transfected CHO cells expressing recombinant EGFR or EGFRvIII were generated at Affimed according to the following protocol:

The genes encoding the wild type EGFR or the deletion mutant EGFRvIII were synthesized by Life Technologies/GeneArt (Regensburg, Germany) and subcloned into the mammalian expression vector pcDNA5/FRT. Stable CHO cell lines expressing recombinant wild type EGFR or EGFRvIII were generated based on the host cell line Flp-In CHO (Life Technologies) previously adapted to suspension growth. One day prior to the transfection, Flp-In CHO cells were subcultured in HyClone CDM4 CHO supplemented with L-Glutamine, HT Supplement, and Penicillin/Streptomycin (without Zeocin). Stable expression cell lines were generated by co-transfection of the Flp-In CHO cell line with pcDNA5/FRT-based product expression and integration plasmid and the Flp recombinase expression plasmid pOG44 (Life Technologies) using Polyethylenimine (PEI) transfection reagent. 2.5 µg total DNA were diluted in 50 µL OptiMEMI medium and combined with 7.5 g PEI diluted in 50 µl OptiMEMI medium. The mixture was incubated for 10 minutes and then added to 2×10$^6$ Flp-In CHO cells suspended in 1 mL CHO—S—SFMII medium. One day after the transfection, cells were diluted to a density of 1×10$^5$ viable cells/mL in CHO—S—SFMII medium supplemented with 50 µg/mL Hygromycin B and seeded in T75 culture flasks. Flp recombinase mediates the insertion of the Flp-In expression construct into the genome at the integrated FRT site through site-specific DNA recombination. During the selection phase, the viable cell density was measured once or twice a week, and cells were centrifuged and resuspended in fresh selection medium at a maximal density of 1×10$^5$ viable cells/mL. Stable cells expressing EGFR or EGFRvIII recovered after approximately 2-3 weeks of selection using 500 µg/mL Hygromycin B and were then transferred into HyClone CDM4 CHO suspension culture medium. Stable wild type EGFR or EGFRvIII expressing cells were cryopreserved in medium containing 50% ProFreeze (Lonza) and 7.5% DMSO.

To determine the density of wild type EGFR or EGFRvIII cell surface antigens on the stably transfected cell lines, a flow cytometric indirect immunofluorescence assay (QI-FIKIT, Dako) was used according to the manufacturer's instructions and demonstrated approximately equal densities of the wild type EGFR on CHO$^{EGFR}$ stably transfected cells and EGFRvIII on CHO$^{EGFRvIII}$ stably transfected cells, whereas on untransfected CHO cells no wild type EGFR or EGFRvIII binding sites could be detected.

Determination of Antibody Binding and Affinity by Flow Cytometry:

Cells were incubated with 100 µL of serial dilutions of the indicated scFv antibodies starting at 100 µg/mL (~3300 nM) in FACS buffer for 45 min on ice. After three times washing with FACS buffer the cells were incubated with 0.1 mL of 10 µg/mL mouse monoclonal anti-His antibody clone 13/45/31 in the same buffer for 45 min on ice. After a second washing cycle, the cells were incubated with 0.1 mL of 15 µg/mL FITC-conjugated goat anti-mouse IgG antibodies under the same conditions as before. As a control, cells were incubated with the anti-His IgG 13/45/31 followed by the FITC-conjugated goat anti-mouse IgG antibodies without scFvs. The cells were then washed again and resuspended in 0.2 mL of FACS buffer containing 2 µg/mL propidium iodide in order to exclude dead cells. The fluorescence of 1×10$^4$ living cells was measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples were calculated using CXP software (Beckman-Coulter, Krefeld, Germany) or Incyte software (Merck Millipore, Schwalbach, Germany).

In case of analysis with Beckman-Coulter FC500 MPL flow cytometer 0.5×10$^6$ cells/staining and in case of Millipore Guava EasyCyte flow cytometer only 0.25×10$^6$ cells/staining were used.

After subtracting the fluorescence intensity values of the cells stained with the secondary and tertiary reagents alone the KD values were calculated employing the equation for one-site-binding (hyperbola) of the GraphPad Prism software (GraphPad Prism version 6.00 for Windows, GraphPad Software, La Jolla Calif. USA).

Results are shown in FIG. 3.

Example 4: SDS PAGE and Western Blot to Analyse Binding Specificity of EGFRvIII-Binding Antibodies To test binding specificity of EGFRvIII/CD3 Tandem diabodies containing different binding domains for EGFRvIII antigen and to demonstrate the absence of binding to the wild type EGFR antigen, sodium dodecyl sulfate Polyacrylamide gel electrophoresis (SDS-PAGE) and Western blot analysis is performed.

Sequences encoding the extracellular domain of the wild type EGFR or the truncated EGFRvIII are fused by recombinant DNA technologies to the Fc portion of a human IgG antibody. DNA constructs are transfected into CHO cells which secrete the recombinant wild type EGFR-Fc or EGFRvIII-Fc as soluble proteins into the cell culture supernatant, from where it is purified using Protein A chromatography. Through intramolecular disulfide bond formation in the Fc-portion, the wild type EGFR-Fc (or EGFRvIII-Fc) fusion antigens are forming dimers of two identical chains. EGFRvIII-Fc due to the EGFRvIII-specific 267 amino acid deletion is approx. 25 kD smaller than EGFR-Fc, resulting in an approx. 50 kD size difference in the dimeric forms of the Fc fusion proteins.

Equal amounts of the purified wild type EGFR-Fc (and EGFRvIII-Fc) are mixed with non-reducing 2×SDS PAGE sample buffer, or reducing 2×SDS PAGE sample buffer containing dithiothreitol (DTT) as reducing agent. Samples with DTT are heated at 95° C. for 5 min prior to loading on 4-20% Criterion TGX Precast SDS PAGE Gels (Biorad). 1 g of protein sample per lane is used. To separate the proteins in the gel, SDS-PAGE is run in 1×Tris/Glycine/SDS buffer (Biorad) at 300 V for approx. 25 min. Total protein is visualized in the gel using the Criterion Stain-free Molecular Imaging System (Biorad). Page Ruler Unstained Protein ladder (Thermo Scientific) is used as a molecular weight marker. Gel is then blotted on a PVDF Membrane using Semi-dry blotting Fastblot system from BioRad. The membrane is blocked in 3% (w/v) skim milk powder in 1×TBS for 30 min at room temperature. The membranes are cut into pieces, each containing similar protein samples blotted. Different Tandem diabodies are diluted to a concentration of 2 g/ml in 3% (w/v) skim milk powder in 1×TBS and incubated with individual membrane pieces for 1 hour on a shaking platform. The anti-EGFR antibody Cetuximab is used as a control at a concentration of 10 µg/ml. Membranes are washed with TBST (TBS+0.1% (v/v) Tween 20) three times for 10 min each and once with TBS prior to incubation with secondary HRP-conjugated detection antibodies, Penta HIS-HRP (QIAGEN) for the detection of Tandem diabodies or Protein L-HRP (Thermo Scientific) for the detection of Cetuximab, 1:5000 diluted in 3% skim milk powder in TBS for 1 hour on a shaking platform. Membranes are washed with TBST (TBS+0.1% (v/v) Tween 20) three times for 10 min each and once with TBS. HRP mediated color development on the membrane is initiated by the addition of 0.06% DAB+0.02% CoCl$_2$+0.015% H$_2$O$_2$ in TBS. The reaction is stopped by adding water. Membranes are dried and scanned.

Results are shown in FIG. 4.

Example 5: Analysis of Binding by Enzyme Linked Immunosorbent Assay (ELISA) of EGFRvIII/CD3 Tandem Diabody Antibodies Containing Different EGFRvIII Binding Domains to EGFRvIII Antigen and Binding to CD3, as Well as their Specificity of Binding to EGFvIII with No Binding to the Wild Type EGFR Antigen ELISA Procedure:

96-well ELISA plates (Immuno MaxiSorp; Nunc) are coated overnight at 4° C. with EGFRvIII-Fc, wild type EGFR-Fc or CD3γε recombinant antigen in 100 mM Carbonate-bicarbonate buffer. To obtain approximately equal molar coating densities of the antigens, EGFRvIII-Fc is coated at a concentration of 4 µg/ml, EGFR-Fc at a concentration of 6 µg/ml, and CD3γε antigen is coated at a concentration of 1.5 µg/ml. After a blocking step with 3% (w/v) skimmed milk powder (Merck) dissolved in PBS, 11 serial dilutions of the different EGFRvIII/CD3 Tandem diabodies ranging from 200 ng/µl to 6.5×10$^{-6}$ ng/µl in PBS containing 0.3% (w/v) skimmed milk powder (Merck) are incubated on the plates for 1.5 h at 25° C. Following the incubation, plates are washed three times with 300 µl per well of PBS containing 0.1% (v/v) Tween 20 (Serva). 50 ng/ml of Protein L-HRP is added and incubated on the plates for 1 h at 25° C. After washing three times with 300 µl per well of PBS containing 0.1% (v/v) Tween 20, Tetramethylbenzidine (TMB) Substrate (Seramun) is added for the detection. The reaction is stopped after approx. 2 minutes through the addition of 100 µl per well of 0.5 M $H_2SO_4$. The absorbance of the wells is measured at 450 nm with a multiwell plate reader (Victor, Perkin Elmer).

Absorbance values are plotted in a diagram using GraphPad Prism software (GraphPad Software, San Diego Calif.).

Results are shown in FIG. 5.

Example 6: Measurement of Tandem Diabody Binding to EGFRvIII by SPR

Preparation of Anti-Hu Fc IgG CM5-Chip

Anti-hu Fc IgG CM5-chip was prepared as described above (Example 2).

Concentration Range of the Tandem Diabodies Used in the SPR Measurement:

tandem diabody concentrations were checked before SPR measurement by A280 determination using Nandrop. The concentration in the stock solution (c) was calculated according to the equation:

$$c[mg/ml] = (A280)/(2.25\ [cm^2/mg] \times 1\ [cm])$$

The different extinction coefficients were calculated with the 'Expasy Protparam' prediction tool (web.expasy.org/protparam/). For calculation of the molar concentration a molecular weight of 105 kD was assumed for all tandem diabodies. The tandem diabody concentrations were adjusted to the final dilutions mentioned below by serial dilution in 1 x HBS-P+ buffer. The following concentrations were prepared: 150 nM, 30 nM, 6 nM, 1.2 nM, 0.24 nM, 0.048 nM and 0 nM, or 90 nM, 30 nM, 10 nM, 3.33 nM, 1.11 nM, 0.37 nM, 0.123 nM, 0.041 nM and 0 nM, or as indicated.

Binding Assay Conditions for KD Measurement of Tandem Diabodies

EGFRvIII-Fc fusion-protein was diluted in 1×HBS-P+ to a concentration of 6.25 nM. The antigen solution was injected at a flow rate of 10 µl/min for 40 sec for EGFRvIII-Fc. The antigen was injected over flowcell 2. Flowcell 1 was the reference cell.

1×HBS-P+ was used as running buffer for the entire procedure. The tandem diabody dilutions were injected at a flow rate of 30 L/min for 180 sec over all flowcells. Signals measured in flow cell 1 without captured antigen were subtracted from signals in flow cell 2 to correct the binding curves for background binding. After 540 sec dissociation time the chip was regenerated as described below.

The anti-hu Fc IgG Chip was regenerated by injection of high salt buffer 3.0 M $MgCl_2$ (3×15 sec, 10 µL/min). Prior to each measurement, three "start-up cycles" were performed without tandem diabodies. The tandem diabody solutions were measured from lowest to highest concentration. One cycle with neat running buffer (0 µM) was included.

The binding parameters of the tandem diabodies were determined in MCK (Multi Cycle Kinetic) measurements. For estimation of apparent binding affinities the binding curves were evaluated using the "Kinetic" method included in the Biacore X100 evaluation software. By this method the binding curves are globally and locally fitted by the software using the "Langmuir 1:1 interaction model".

Binding Parameters of Tandem Diabodies

To analyse the effect of combining two EGFRvIII binding domains into a bivalent or multivalent or multispecific molecule, like the EGFRvIII/CD3 tandem diabody, the apparent affinities of EGFRvIII/CD3 tandem diabodies to EGFRvIII antigen were measured by SPR employing Biacore X100 (FIG. 6).

Apparent affinities of EGFRvIII-specific binding domains in EGFRvIII/tandem diabodies were improved for all tested molecules, reaching a $K_D$ of 11 pM for the best binding tandem diabody. Reduction of the $K_D$ of tandem diabodies containing affinity matured domains relative to the corresponding tandem diabody containing the parental EGFRvIII binding domain were up to 25-fold. Improvements in the $K_D$ relative to the $K_D$ measured for the monovalently binding scFvs were also up to 25-fold. Interestingly, in contrast to the improvements achieved through the affinity maturation, which was predominantly driven by improved $k_{ON}$, the further improvement in the binding affinities in the bivalent Tandem diabody format is largely achieved through slower $k_{offOFF}$ (Table 4).

The tandem diabody format thereby provides a means of further enhancing binding affinities while maintaining the specificity of an antibody binding domain.

TABLE 4

Summary of $K_D$, association rate ($k_{ON}$) and dissociation rate ($k_{OFF}$) measured for binding of different EGFRvIII/CD3 tandem diabodies, containing bivalent parental or affinity matured EGFRvIII-specific binding domains in the domain order $V_L^{CD3}$-$V_H^{EGFRvIII}$-$V_L^{EGFRvIII}$-$V_H^{CD3}$, to recombinant EGFRvIII-Fc antigen in the SPR 1:1 binding model.

| | | EGFRvIII binding | | | | | | | |
|---|---|---|---|---|---|---|---|---|---|
| | | Affinity | | | association rate | | | dissociation rate | |
| EGFRvIII binding | | improvement factor | | | improvement factor | | | improvement factor | |
| domain in tandem diabody | $K_D$ [nM] | to parent. tandem diabody | rel. to scFv | $k_{on}$ [1/Ms] | to parent. tandem diabody | rel. to scFv | $k_{off}$ [1/s] | to parent. tandem diabody | rel. to scFv |
| parental: | | | | | | | | | |
| Li3G30 | 0.289 | 1 | 26.9 | 6.7E+5 | 1 | 4.2 | 1.9E−4 | 1 | 6.3 |

TABLE 4-continued

Summary of $K_D$, association rate ($k_{ON}$) and dissociation rate ($k_{OFF}$) measured for binding of different EGFRvIII/CD3 tandem diabodies, containing bivalent parental or affinity matured EGFRvIII-specific binding domains in the domain order $V_L^{CD3}$-$V_H^{EGFRvIII}$-$V_L^{EGFRvIII}$-$V_H^{CD3}$, to recombinant EGFRvIII-Fc antigen in the SPR 1:1 binding model.

| | EGFRvIII binding | | | | | | | | |
|---|---|---|---|---|---|---|---|---|---|
| | Affinity | | | association rate | | | dissociation rate | | |
| EGFRvIII binding domain in tandem diabody | $K_D$ [nM] | improvement factor to parent. tandem diabody | rel. to scFv | $k_{on}$ [1/Ms] | improvement factor to parent. tandem diabody | rel. to scFv | $k_{off}$ [1/s] | improvement factor to parent. tandem diabody | rel. to scFv |
| Affinity matured: | | | | | | | | | |
| 469 | 0.029 | 10.1 | 25.3 | 3.2E+6 | 4.8 | 3.8 | 9.0E−5 | 2.1 | 6.6 |
| 470 | 0.049 | 5.9 | 24.0 | 1.3E+6 | 2.0 | 3.0 | 6.4E−5 | 3.0 | 7.8 |
| 471 | 0.014 | 20.0 | 18.0 | 2.7E+6 | 4.0 | 2.4 | 3.8E−5 | 5.0 | 7.6 |
| 472 | 0.011 | 25.2 | 7.0 | 4.4E+6 | 6.6 | 1.2 | 5.0E−5 | 3.8 | 6.0 |
| 478 | 0.032 | 8.9 | 4.8 | 2.9E+6 | 4.4 | 2.1 | 9.5E−5 | 2.0 | 2.4 |
| 479 | 0.166 | 1.7 | 15.3 | 1.4E+6 | 2.2 | 3.8 | 2.4E−4 | 0.8 | 4.0 |

Example 7: Immunohistochemistry (IHC) Staining of Solid Tumor Tissue Sections with an Anti-EGFRvIII Bispecific Diabody or Cetuximab In contrast to wild type EGFR, which is widely expressed on healthy tissues, expression of the mutated receptor EGFRvIII is highly tumor specific. Whereas a high frequency of expression of EGFRvIII in glioblastoma is consistently described in the literature, expression prevalence of EGFRvIII and its homogeneity of expression in other tumors remain controversial.

Figure 7A:
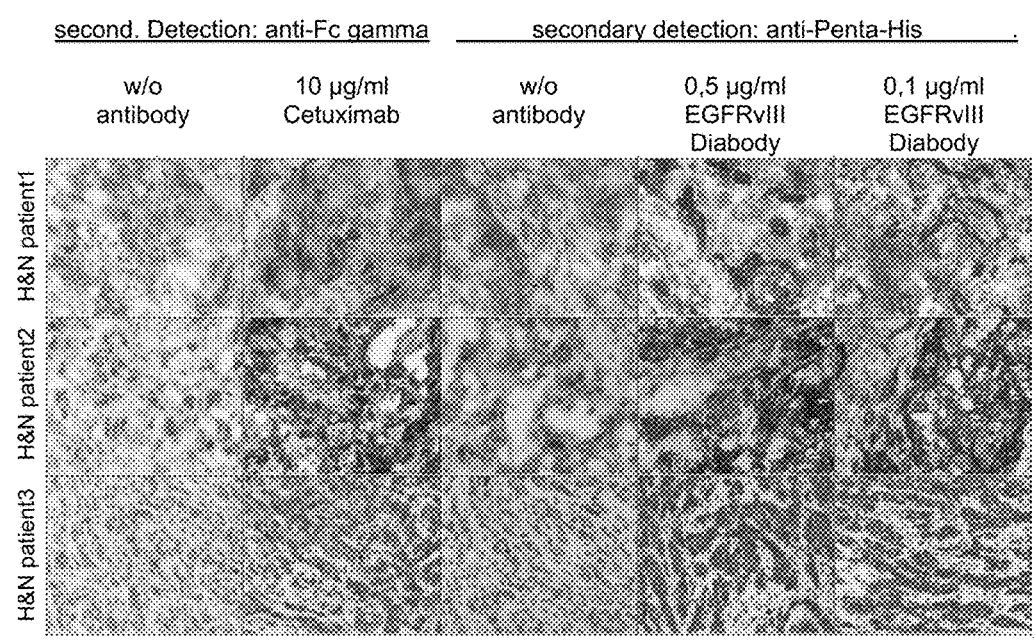
FIGS. 7A-7C show results from immunohistochemistry (IHC) staining of tissue sections from (A) three individual Head and Neck (H&N) cancer patients, (B) three individual Glioblastoma patients, and (C) representative results from prostate cancer, breast cancer (Her2 neg), and Non-small-cell lung cancer (NSCLC). Sections were stained with 2 different concentrations of an EGFRvIII-specific Diabody containing the EGFRvIII-specific binding domain Li3G30 in a bivalent conformation similar to the arrangement in EGFRvIII targeting tandem diabodies antibodies (e.g. ($V_L^{CD3}$-)$V_H^{EGFRvIII}$-$V_L^{EGFRvIII}$(-$V_H^{CD3}$), but lacking the CD3 binding portions. As a control, sections were stained with the EGFR-specific IgG antibody Cetuximab, which recognizes EGFR (present on healthy as well as cancer tissue) as well as EGFRvIII. Specificity of the staining was confirmed by control sections incubated with the secondary reagents in the absence of EGFR- or EGFRvIII-specific primary antibodies.
Figure 7B:
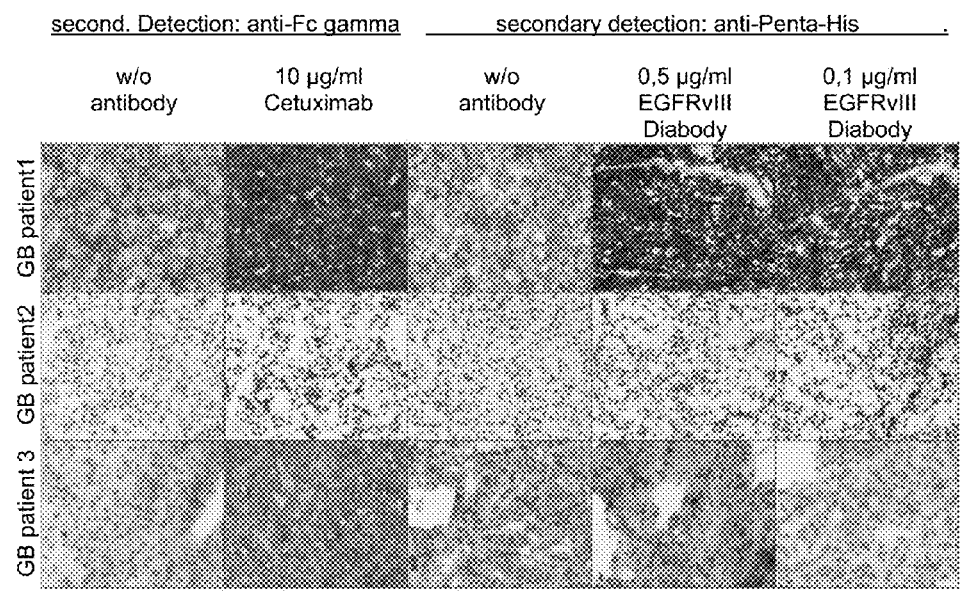
Figure 7C:
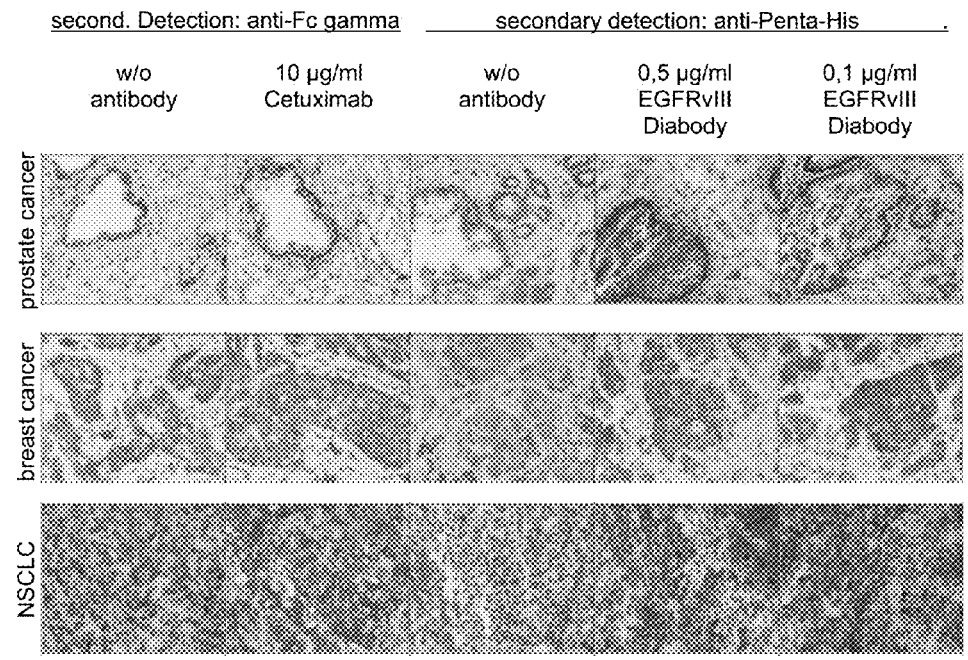

A small immunohistochemistry (IHC) study was initiated and tissue sections from up to 3 individual cancer patients with Glioblastoma (GB), Head and Neck (H&N) cancer, prostate cancer, Her2-negative breast cancer, as well as Non-small-cell lung cancer (NSCLC) were analysed for reactivity with the EGFRvIII specific binding domain according to the invention in a bivalent Diabody format (FIG. 7).

The immunohistochemistry study was performed to assess expression of EGFRvIII in different tumors as well as the tumor specificity of EGFRvIII binding antibodies. EGFRvIII binding of EGFRvIII-specific variable domains was tested in a bivalent diabody format containing the EGFRvIII binding domain Li3G30 in the arrangement $V_H^{EGFRvIII}$-$V_L^{EGFRvIII}$. Secondary detection was performed via the His-tag on the Diabody protein. As a control the native EGFR-specific IgG antibody Cetuximab (Erbitux) was used.

All human tissue sections were purchased from BioChain Institute, Inc. and sections were handled according to the instruction of the Supplier. Tissue sections were adapted to room temperature and incubated with DAKO peroxidase block followed blocking with 10% goat serum. The EGFRvIII-specific Diabody was incubated at two concentration levels of 0.5 g/ml and 0.1 g/ml for one hour followed by an anti His antibody (Dianova) and detected by Envision+ HRP-DAB system for mouse antibody (DAKO). Staining of tissue sections with the control item Erbitux (Merck KGaA) was performed at a concentration of 10 μg/ml using the Klear Human HRP-Polymer DAB Detection System (GBI Labs) according to the manufacturer's instructions.

Finally sections were stained with hematoxylin and mounted with mountant medium (Shandon Consul Mount™, Thermo Scientific).

Results are shown in FIG. 7.

Two of the three Glioblastoma samples showed a clear and specific reactivity with the EGFRvIII-specific Diabody. Surprisingly, all three Head and Neck cancer samples showed a strong and clear positivity for EGFRvIII and also on prostate cancer, breast cancer and NSCLC, specific staining of the tumor tissue was obtained with the EGFRvIII-specific antibody described herein (FIG. 7).

Based on these properties, the EGFRvIII binding domains described here are excellently suited for the development of multispecific, multivalent, immune-effector cell engaging, tumor targeting antibody therapeutics, such as, for example, EGFRvIII/CD3 bispecific tandem diabodies.

Figure 8A:
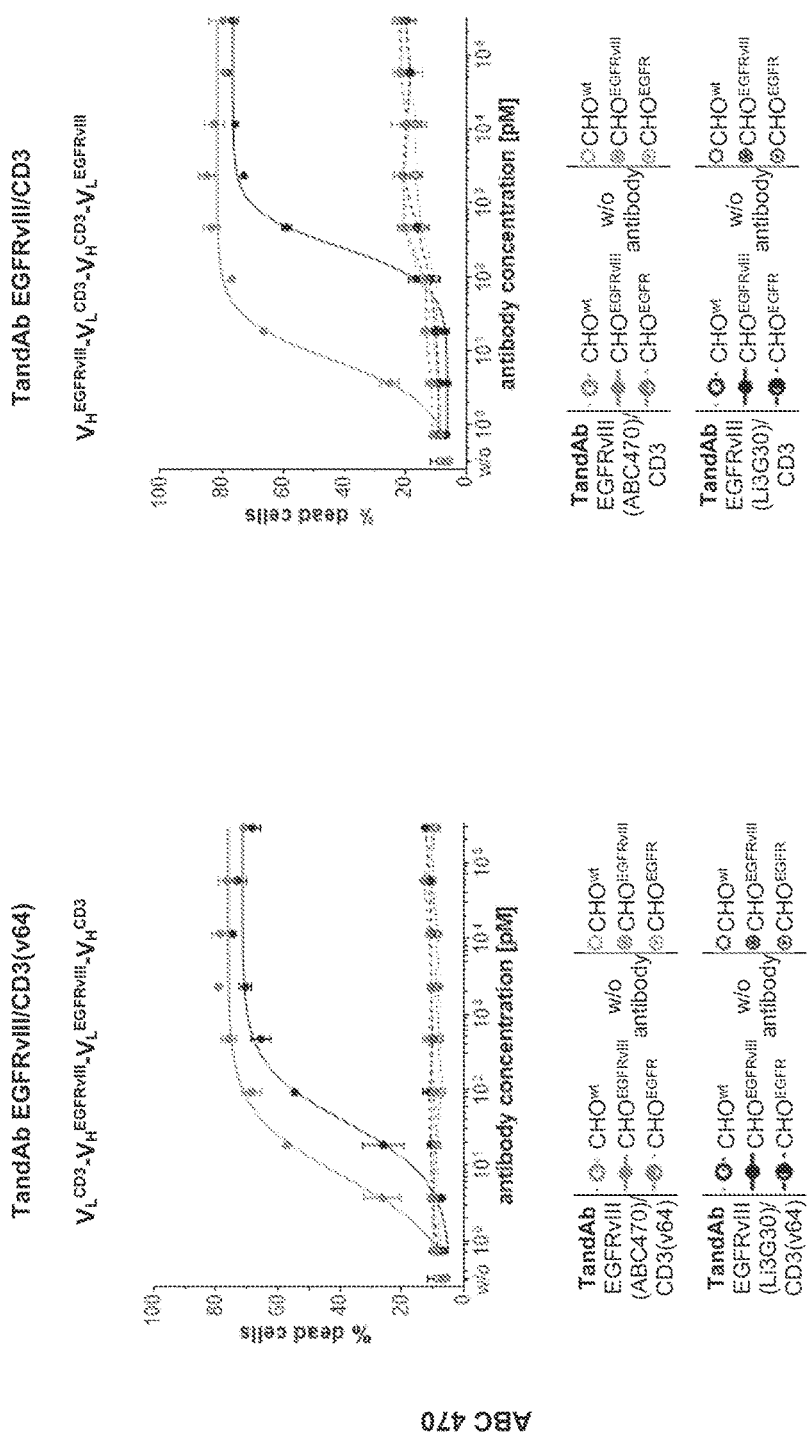
Figure 8B:
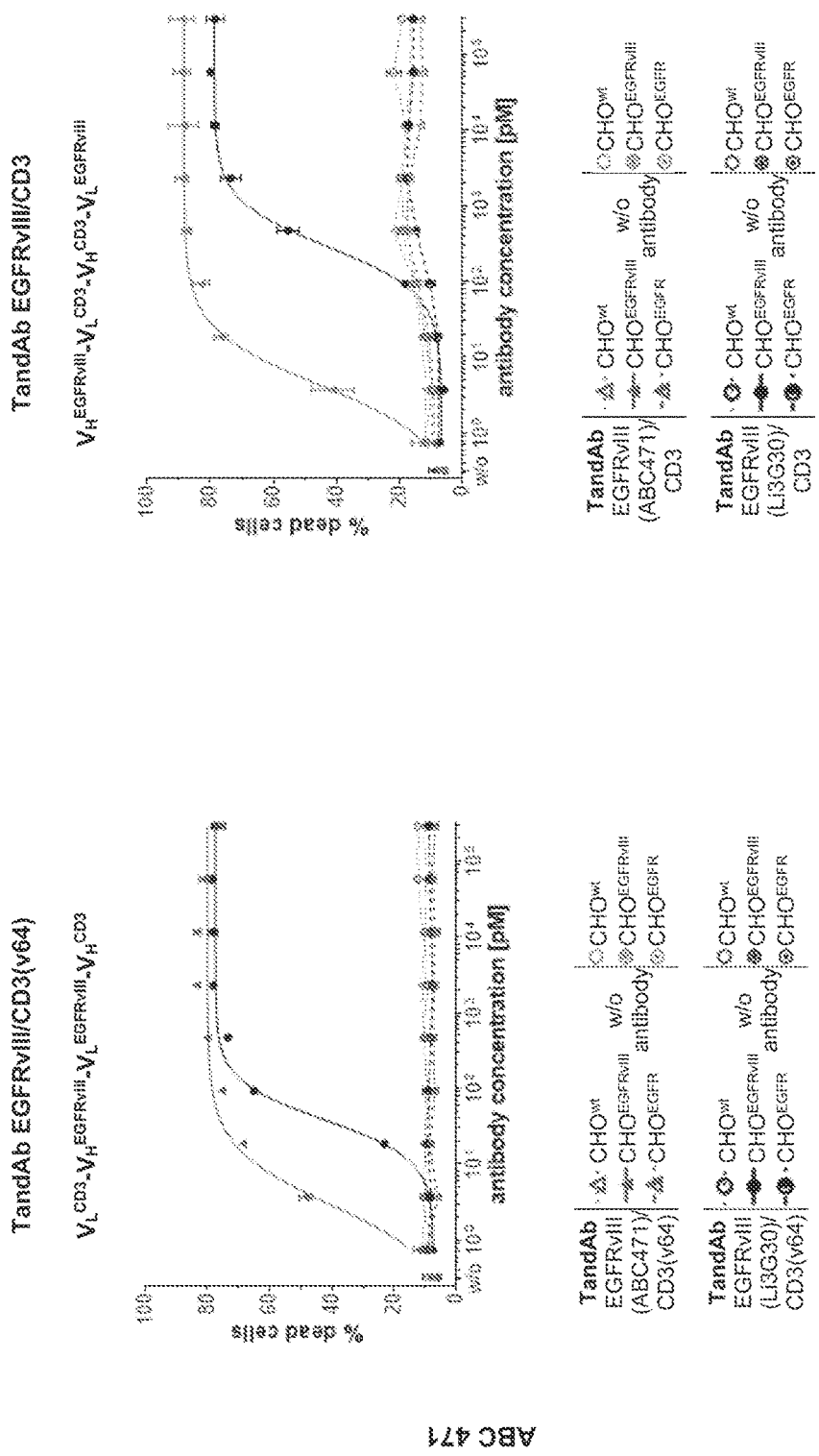

Example 8: Assessment of Cytotoxic Activity Mediated by EGFRvIII/CD3 Tandem Diabodies in FACS-Based Cytotoxicity Assay EGFRvIII/CD3 tandem diabody antibodies containing the parental or affinity matured EGFRvIII specific domains combined with different CD3 binding domains and/or having a different order of the individual binding domains in the tandem diabody molecules, were analysed in cell based cytotoxicity assays (FIG. 8). Target-mediated dependency, specificity of tandem diabodies, and T cell-mediated killing were analysed by employing EGFRvIII expressing CHO cells ($CHO^{EGFRvIII}$), wild type EGFR expressing CHO cells ($CHO^{EGFR}$), and untransfected CHO cells as target cells.

Material (Media, Buffer and Reagents):

DMSO (Sigma), EasySep™ Human T Cell Enrichment Kit (Stem Cell Technologies), EasySep™ Human CD4+ T Cell Enrichment Kit (Stem Cell Technologies), EasySep™ Human CD8+ T Cell Enrichment Kit (Stem Cell Technologies), The Big Easy EasySep™ Magnet (Stem Cell Technologies), FCS (Invitrogen), Lymphoprep (Stem Cell), L-Glutamine (Invitrogen), mIgG1 FITC (ADG), CD16-FITC (MEM-154) (Thermo Fisher Scientific), mIgG1-FITC/mIgG1-PE/mIgG1-ECD (Beckman Coulter), mIgG1-PE (Beckman Coulter), mIgG1-PC5 (Beckman Coulter), mIgG1-PC7 (Beckman Coulter), CD8-FITC/CD4-PE/CD3-ECD (Beckman Coulter), CD16-PC5 (Beckman Coulter), CD19-PC7 (Beckman Coulter), CD16-FITC/CD56-PE/CD3-ECD (Beckman Coulter), CD14-PC7 (Beckman Coulter), CD33-PE (MACS Miltenyi Biotech), $NaN_3$ (Roth), PBS (Invitrogen), Penicillin/Streptomycin (Invitrogen), PKH67 Green Fluorescent Cell Linker Midi Kit (Sigma), Gammanorm human IgG (Octapharma), Propidium iodide (Sigma), RPMI-1640 (Invitrogen)

Isolation of PBMC from Buffy Coats and Enrichment of T Cells:

Buffy coats were purchased from the Deutsches Rotes Kreuz, DRK-Blutspendedienst Baden-Württemberg-Hessen (Mannheim, Germany) on the day of blood withdrawal; buffy coat preparations were stored overnight at room temperature before PBMCs were isolated by density gradient centrifugation. The buffy coat sample was diluted with a two-to-threefold volume of PBS, layered on a cushion of Lymphoprep and centrifuged at 800×g for 25 min at room temperature w/o brake. PBMC located at the interface were collected and washed 3 times with PBS before they were used for the enrichment of T cells or flow cytometric analysis. T cells were enriched from the PBMC population using the EasySep™ Human T Cell Enrichment Kit for the immunomagnetic isolation of untouched human T cells and the Big Easy EasySep™ Magnet according to the manufacturer's instructions.

Characterization of Effector Cells by Flow Cytometric Analysis:

Staining of the PBMC was performed to assess the distribution of the PBMC subpopulation and the purity of enriched PBMC or T cell subsets.

For flow cytometric analysis, isolated PBMC or enriched PBMC subpopulations were resuspended in PBS supplemented with 2% heat-inactivated FCS and 0.1% sodium azide (referred to as a FACS buffer) and 1 mg/mL polyclonal human IgG to a density of $0.5-2\times10^6$/mL. Aliquots of 0.5 mL cell suspension were then incubated for 15 min in the dark with antibodies according the following scheme as recommended by the manufacturer.

TABLE 5

Pipetting scheme for characterization of PBMC and fractionated PBMC by flow cytometry

| sample | Antibody | Volume/test |
|---|---|---|
| 1 | CD8-FITC/CD4-PE/CD3-ECD | 20 µL |
|   | CD16-PC5 | 10 µL |
|   | CD19-PC7 | 10 µL |
| 2 | use sample (4) after measurement and add: | |
|   | mIgG$_1$-PC5 | 10 µL |
|   | mIgG$_1$-PC7 | 10 µL |
| 3 | CD16-FITC/CD56-PE/CD3-ECD | 20 µL |
| 4 | mIgG$_1$-FITC/mIgG$_1$-PE/mIgG$_1$-ECD | 20 µL |
| 5 | CD16-FITC (MEM-154) | 20 µL |
|   | CD33-PE | 10 µL |
|   | CD16-PC5 | 10 µL |
|   | CD14-PC7 | 10 µL |
| 6 | mIgG$_1$-FITC | 20 µL |
|   | mIgG$_1$-PE | 20 µL |
|   | mIgG$_1$-PC5 | 10 µL |
|   | mIgG$_1$-PC7 | 10 µL |

After incubation the samples were measured in the order: 3. 4. 5. 6. 1. 2 on a Beckman-Coulter FC500 MPL flow cytometer (Beckman-Coulter, Krefeld, Germany) using protocols established for PBMC and multicolor stainings (FITC PE ECD PC5 PC7; FITC PE ECD; FITC PE PC5 PC7) in the MXP acquisition software (Beckman-Coulter). For the analysis and data plotting, the CXP analysis software (Beckman-Coulter) was used.

Cytotoxicity Assay:

T cells that were used as effector cells were characterized by flow cytometry as described. Target cells used in the cytotoxicity assay were CHO cells stably transfected to overexpress EGFRvIII ($CHO^{EGFRvIII}$), CHO cells stably transfected to express wild type EGFR ($CHO^{EGFR}$) or untransfected CHO cells (CHO). The cell lines were generated as previously described and were cultured under standard conditions as described. For the cytotoxicity assay, target cells were harvested, washed twice with RPMI 1640 medium without FCS, and resuspended in diluent C provided in the PKH67 Green Fluorescent Cell Linker Midi Kit to a density of $2\times10^7$/mL. The cell suspension was then mixed with the equal volume of a double-concentrated PKH67-labeling solution (e.g. 1 µL PKH67 in 250 µL diluent C) and incubated for 2-5 min at RT with periodical mixing according to the manufacturer's instructions. The staining reaction was stopped by adding the equal volume of FCS and incubation for 1 min. After washing the labeled target cells with complete RPMI medium, cells were counted and resuspended to a density of $2\times10^5$/mL in complete RPMI medium.

$2\times10^4$ target cells were then seeded together with T cells at an E:T ratio of 5:1 and the indicated antibodies in individual wells of a round-bottom 96-well micro plate in a total volume of 200 µL/well. Usually 9 serial 1:5 dilutions starting at 30 µg/mL were tested. Spontaneous cell death and killing of targets by effectors in the absence of antibodies were determined in at least three replicates on each plate. Tandem diabody-mediated killing was usually determined in duplicates.

After centrifugation for 2 min at 200 g at RT the assay plates were incubated for 40 h-48 h at 37° C. in a humidified atmosphere with 5% $CO_2$. After incubation, cultures were washed once with FACS buffer and then resuspended in 150 µL FACS buffer supplemented with 2 µg/mL PI. The absolute amount of living target cells that were characterized by a positive green PKH67 staining but are negative for the PI staining was measured using a Millipore Guava EasyCyte flow cytometer (Merck Millipore).

Based on the measured remaining living target cells, the percentage of specific cell lysis was calculated according to the following formula: [1-(number of living targets$_{(sample)}$)/ (number of living targets$_{(spontaneous)}$)]×100%. Sigmoidal dose response curves and EC50 values were calculated by non-linear regression/4-parameter logistic fit using the GraphPad Prism software (GraphPad Prism version 6.00 for Windows, GraphPad Software, La Jolla Calif. USA).

Statistical Analysis:

The lysis values obtained for a given antibody concentration were determined in duplicates and analysed by sigmoidal dose-response/4 parameter logistic fit analysis using the Prism software (GraphPad Prism version 6.00 for Windows, GraphPad Software, La Jolla Calif. USA) and used to calculate EC50 values mean and SD of replicates of lysis percentage.

The results are shown in FIG. 8 and Table 6.

All tested tandem diabodies exhibited concentration dependent, highly specific, cytotoxicity and high efficacy towards EGFRvIII expressing cells, whereas EGFRvIII negative cells were not impaired in their survival. No detectable cytotoxicity was observed in the complete concentration range of any tandem diabody tested on EGFRwt-expressing cells or untransfected cells. Cytotoxicity mediated by EGFRvIII/CD3 tandem diabodies is therefore strictly target dependent. Tandem diabody containing the parental EGFRvIII-binding domain prior to the affinity maturation and having the domain order $V_L^{CD3}$-$V_H^{EGFRvIII}$-$V_L^{EGFRvIII}$-$V_H^{CD3}$, $EC_{50}$ of 25 pM in the cytotoxicity assay (FIG. 8). Corresponding tandem diabodies containing the affinity improved EGFRvIII binding domains in the same domain order ($V_L^{CD3}$-$V_H^{EGFRvIII}$-$V_L^{EGFRvIII}$-$V_H^{CD3}$), consistently demonstrated enhanced cytotoxic potency, reaching $EC_{50}$ of 1.5 pM in the best case (Table 6). The relative improvement in cytotoxic activity was more pronounced in tandem diabodies having the EGFRvIII-specific binding domains in the outer position (domain order $V_H^{EGFRvIII}$-$V_L^{CD3}$-$V_H^{CD3}$-$V_L^{EGFRvIII}$) (Table 6). Up to 70-fold improved cytotoxic potency could be achieved in these tandem diabodies by replacing the low affinity EGFRvIII binding domain Li3G30 with the affinity-improved domains (FIG. 8, Table 6).

TABLE 6

Summary of EC50 values measured in cytotoxicity assays with different EGFRvIII/CD3 Tandem diabodies containing affinity matured EGFRvIII-specific binding domains in two different domain orders. Improvement factor relative to a corresponding Tandem diabody containing the parental EGFRvIII binding domains are indicated.

| | Cytotoxic potency of EGFRvIII/CD3 TandAb domain with order | | | |
|---|---|---|---|---|
| EGFRvIII binding domain in TandAb | (i) $V_L^{CD3(v64)}$-$V_H^{EGFRvIII}$-$V_L^{EGFRvIII}$-$V_H^{CD3(v64)}$ | | (iv) $V_H^{EGFRvIII}$-$V_L^{CD3}$-$V_H^{CD3}$-$V_L^{EGFRvIII}$ | |
| | $EC_{50}$ [nM] | improvement factor relative to parental TandAb | $EC_{50}$ [nM] | improvement factor relative to parental TandAb |
| ABC469 | 11.0 | 2.5 | 6.5 | 33.3 |
| ABC470 | 4.0 | 6.8 | 3.8 | 56.9 |
| ABC471 | 1.5 | 18.2 | 3.1 | 69.8 |
| ABC472 | 4.2 | 6.5 | 10.1 | 21.4 |

Choi et al. (Proc Natl Acad Sci USA. 2013 Jan. 2; 110(1):270-5; WO2013/7185010) describe comparator to t EGFRvIII/CD3 a EGFRvIII/CD3 bispecific T-cell engager (BiTE) having a single binding site for EGFRvIII (based on the murine MR1 domain) and a single binding site for CD3 (based on the anti-CD3 antibody OKT3). In a cell based cytotoxicity assays, this antibody reached 50% of the maximally achieved specific lysis at a concentration of approx. $10^{-2}$ g/ml which corresponds to a molar EC50 concentration of approximately 200 pM for the 52 kD BiTE (FIG. 4C in Choi et al., 2013). The comparison shows that even the herein described tandem diabody containing the parental, not affinity matured EGFRvIII binding domain, has an approximately 10-fold higher cytotoxicity than the EGFRvIII/CD3 BiTE. Moreover, the tandem diabodies according to the invention containing the affinity matured EGFRvIII binding domains, even exhibit 100-fold higher cytotoxicity relative to that of the EGFRvIII/CD3 BiTE.

Example 9: EGFRvIII Receptor Internalization by EGFRvIII/CD3 Tandem Diabodies on CHO Cells Expressing Recombinant EGFRvIII ($CHO^{EGFRvIII}$) or F98 Cells Expressing Recombinant EGFRvIII ($F98^{EGFRvIII}$)

For the assessment of EGFRvIII modulation by EGFRvIII/CD3 tandem diabodies, CHO cells expressing recombinant EGFRvIII ($CHO^{EGFRvIII}$) or F98 cells expressing recombinant EGFRvIII ($F98^{EGFRvIII}$) were incubated in aliquots of $2.5\times10^5$ cells in individual wells of a round-bottom 96 well micro plate together with increasing concentrations of EGFRvIII/CD3 Tandem diabodies in RPMI 1640 medium supplemented with 10% FCS, 2 mM L-glutamine, 100 IU/mL penicillin G sodium, 100 µg/mL streptomycin sulfate, 100 µg/mL sodium pyruvate (herein referred to as complete RPMI medium; all components from Invitrogen) for 24 hours in a humidified incubator with 5% $CO_2$ at 37° C. Several aliquots of cells were cultured in the absence of antibody and served as control samples for the detection of the maximal EGFRvIII cell surface level and as negative controls for the staining with the secondary reagents alone.

After the incubation, cells were washed twice with ice-cold phosphate-buffered saline (PBS, Invitrogen) supplemented with 2% heat-inactivated FCS (Invitrogen) and 0.1% sodium azide (Roth, Karlsruhe, Germany) (herein referred to as FACS buffer) and then stained with saturating concentrations (10 µg/mL) of the identical antibody with which they were incubated during the modulation culture to assess the maximal antibody binding corresponding to remaining EGFRvIII antigens on the cell surface. Aliquots of cells that were cultured in the absence of antibodies were stained with the identical antibody at saturating concentrations to determine the maximal antibody binding capacity corresponding to the maximal measurable EGFRvIII level on the cell surface. After washing with FACS buffer three times, cells that were treated with tandem diabodies and stained with 10 µg/mL anti-His mAb (Dia910, Dianova) followed by 15 µg/mL FITC-conjugated goat anti-mouse IgG (Dianova). After repeated washing with FACS buffer, cells were resuspended in FACS buffer containing 2 µg/mL propidium iodide (Sigma) to exclude dead cells. From each sample ~$5\times10^3$ propidium iodide-negative cells were analyzed using the MXP software with a FC500 MPL flow cytometer (Beckman-Coulter, Krefeld, Germany), and the mean fluorescent intensities (MFI) of the measured samples were determined with the CXP software (Beckman-Coulter) or cells were analysed with a Millipore Guava EasyCyte flow cytometer using the Incyte software (Merck Millipore, Schwalbach, Germany).

After subtraction of the signal obtained from staining of the cells with the secondary reagents alone, the mean fluorescent intensities of the measured samples were plotted in a diagram using GraphPad Prism software (GraphPad Software, San Diego Calif.), and the relative amount of remaining EGFRvIII on the cell surface was calculated using the fluorescence signal obtained by staining at 37° C.

in the absence of EGFRvIII/CD3 tandem diabodies of untreated cell samples, which was set to represent 100% of cell surface EGFRvIII.

The results are shown in FIG. 9.

Several literature reports describe that the deletion mutant EGFRvIII shows impaired internalization compared to the native EGFR (Fenstermaker et al. 2000, Han et al. 2006, Grandal et al. 2007, Gan et al. 2009). Despite that, several published reports with EGFRvIII specific antibodies or antibodies directed against the wild type EGFR which also bind to EGFRvIII (e.g. Cetuximab) describe rapid internalization and degradation of the EGFRvIII in EGFRvIII expressing cells after binding of the respective antibodies (Reist et al. 1995, Foulon et al. 2000, Kuan et al. 2000, Patel et al. 2007, Jutten et al. 2009, Dreier et al. 2012).

For internalization assays transfected CHO$^{EGFRvIII}$ cells were used which overexpress EGFRvIII. These EGFRvIII expressing cells were incubated with different concentrations of EGFRvIII/CD3 Tandem diabodies at 37° C. for 24 hours, conditions which in the context of other EGFRvIII binding antibodies are described to induce strong internalization. After this modulation, during which antibody-receptor complexes could either internalize or not, the respective antibodies were used at a saturating concentration of 10 µg/ml to stain all remaining EGFRvIII receptor molecules on the cell surface (FIG. 9). The results presented in FIG. 9 show, that under all tested conditions, more than 80% and up to 140% of the EGFRvIII receptor molecules present on untreated cells are still available after the exposition of the cells to the EGFRvIII-binding tandem diabodies (140% or more general values >100% mean that cells treated with the tandem diabodies in contrast to having (through internalization) a reduced numbers of the receptor on the cell surface, show an increase of the receptor on the cell surface. The normalization to 100% comes from the comparison to cells which were not treated). These results suggest, that EGFRvIII/CD3 tandem diabodies according to the invention surprisingly do not show any internalization tendency (FIG. 9). Instead of inducing internalization, binding of EGFRvIII-specific domains according to the invention might even inhibit internalization and lead to an increase of the EGFRvIII receptor level on the cell surface. The results presented in FIG. 9 show that, relative to untreated cells at least more than 80% still remains on the cell surface after the exposure of the cells to the EGFRvIII-binding antibodies, under all conditions tested. These results suggest, that EGFRvIII/CD3 antibodies according to the invention, in particular EGFRvIII/CD3 tandem diabodies, surprisingly do not show any internalization tendency (FIG. 9). Instead of inducing internalization, binding of EGFRvIII-specific domains according to the invention might either inhibit internalization or facilitate increased expression of EGFRvIII leading to its increased cell surface density.

Example 10: Assessment of Cell Proliferation in PBMC Cultures in the Presence of EGFRvIII/CD3 (or EGFRvIII/CD16A) Tandem Diabodies In order to assess whether EGFRvIII/CD3 (or EGFRvIII/CD16A) tandem diabodies induce activation of T cells and subsequent proliferation in the absence of EGFRvIII+ target cells, human PBMC were cultured in the presence of increasing concentrations EGFRvIII/CD3 Tandem diabodies. Proliferation was assessed in a BrdU incorporation assay after 5 days incubation.

Material (Media, Buffer and Reagents):
FCS (Invitrogen), Human serum (Sigma), Lymphoprep (Stemcell Technologies), L-Glutamine (Invitrogen), OKT3 (Biolegend), PBS (Invitrogen), beta-Mercaptoethanol (Invitrogen), Penicillin/Streptomycin (Invitrogen), RPMI-1640 (Invitrogen), Sodium pyruvate (Invitrogen), BrdU Cell Proliferation ELISA (Roche).

Cells:
Buffy coats were purchased from the Deutsches Rotes Kreuz, DRK-Blutspendedienst Baden-Württemberg-Hessen (Mannheim, Germany) on the day of blood withdrawal; buffy coat preparation was stored overnight at room temperature before PBMC were isolated.

Isolation of PBMC from Buffy Coats and Enrichment of T Cells:
PBMC were isolated from buffy coats by density gradient centrifugation. The buffy coat sample was diluted with a two-to-threefold volume of PBS, layered on a cushion of Lymphoprep and centrifuged at 800×g for 25 min at room temperature w/o brake. PBMC located in the interface were collected and washed 3 times with PBS before they were used in the proliferation assay.

Proliferation Assay:
All assay plates were blocked with RPMI 1640 medium supplemented with 10% heat-inactivated human serum, 4 mM L-glutamine, 100 U/mL penicillin G sodium, 100 µg/mL streptomycin sulfate, 1 mM sodium pyruvate, 0.05 mM beta-mercaptoethanol (herein referred to as complete RPMI medium) for 2 hours at RT to prevent unspecific binding of antibodies to the plastic surface. After removal of the blocking medium 4×10$^5$ PBMC were seeded in complete RPMI medium in individual wells of flat-bottom 96-well micro plates together with the indicated concentrations of test and control items in a total volume of 200 µL/well in triplicates. IgG anti-CD3 clone OKT3 was used as a positive control. To assess spontaneous proliferation cells were cultured in the absence of antibodies in 6 replicates. Plates were then incubated for 4 days at 37° C. and 5% CO$_2$ in a humidified atmosphere. 18 hours prior to the end of incubation cell cultures were pulsed with 100 µM BrdU. Incorporated BrdU was quantified using the BrdU Proliferation ELISA kit according to the instruction of the manufacturer. After stopping the color development by adding 100 mM H$_2$SO$_4$ the absorption was measured at 450 nm with a multilabel plate reader (Victor 3, Perkin Elmer). Absorbance values were analyzed and mean values together with SDs were plotted using GraphPad Prism software (GraphPad Prism version 6.00 for Windows, GraphPad Software, La Jolla Calif. USA).

The results are shown in FIG. 10.

Example 11: Correlation of CD3 Binding Affinity and Cytotoxic Potency of EGFRvIII/CD3 Tandem Diabodies EGFRvIII/CD3 Tandem diabodies containing the same EGFRvIII binding domain (Li3G30) combined with different CD3 binding domains having a range of affinities for the CD3 T-cell antigen were constructed, expressed and binding to CD3+ Jurkat cells and EGFRvIII+ CHO$^{EGFRvIII}$ cells was determined; additionally, cytotoxicity assays using CHO$^{E-}$$_{GFRvIII}$ cells as target cells and PBMC as effector cells were performed. All tested tandem diabodies tested in this example have the same order of the individual VH and VL (heavy and light chain) domains: $V_L^{CD3}$-$V_H^{EGFRvIII}$-$V_L^{EGFRvIII}$-$V_H^{CD3}$.

Flow cytometric assessment of both antibody binding to EGFRvIII+ CHO$^{EGFRvIII}$ cells and cytotoxic activity mediated by EGFRvIII/CD3 Tandem diabodies was performed as described in previous examples.

The apparent affinity of EGFRvIII/CD3 Tandem diabodies to CD3+ cells was determined by flow cytometry after staining of CD3+ Jurkat cells with increasing concentrations of the Tandem diabodies. $K_D$ values were calculated by non-linear regression/hyperbola using the mean fluorescence values determined by flow cytometry for the individual Tandem diabody concentrations.

Material (Media, Buffer and Reagents):

Anti-His IgG 13/45/31 (Dianova), FCS (Invitrogen), FITC-conj. goat anti-mouse IgG min X (Dianova), L-Glutamine (Invitrogen), $NaN_3$ (Carl Roth), PBS (Invitrogen), Penicillin/Streptomycin (Invitrogen), Propidium iodide (Sigma), RPMI-1640 (Invitrogen) Cells:

Jurkat cells (kindly provided by Dr. G. Moldenhauer, DKFZ, Heidelberg, Germany) were cultured in RPMI 1640 medium supplemented with 2 mM L-glutamine and 100 IU/mL penicillin G sodium and 100 µg/mL streptomycin sulfate (all components from Invitrogen, herein referred to as completed RPMI 1640 medium).

Determination of Antibody Affinity to CD3+ Cells by Flow Cytometry:

Cells were incubated with 100 µL of serial dilutions of the indicated antibodies starting at 100 µg/mL (~1000 nM) in ice-cold PBS supplemented with 2% heat-inactivated FCS and 0.1% sodium azide (referred to as a FACS buffer) for 45 min on ice. After three times washing with FACS buffer the cells were incubated with 0.1 mL of 10 µg/mL mouse monoclonal anti-His antibody clone 13/45/31 in the same buffer for 45 min on ice. After a second washing cycle, the cells were incubated with 0.1 mL of 15 µg/mL FITC-conjugated goat anti-mouse IgG antibodies under the same conditions as before. As a control, cells were incubated with the anti-His IgG 13/45/31 followed by the FITC-conjugated goat anti-mouse IgG antibodies without primary antibody. The cells were then washed again and resuspended in 0.2 mL of FACS buffer containing 2 µg/mL propidium iodide in order to exclude dead cells. The fluorescence of $1 \times 10^4$ living cells was measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples were calculated using CXP software (Beckman-Coulter, Krefeld, Germany) or Incyte software (Merck Millipore, Schwalbach, Germany). In case of analysis with Beckman-Coulter FC500 MPL flow cytometer $0.5 \times 10^6$ cells/staining and in case of Millipore Guava EasyCyte flow cytometer only $0.25 \times 10^6$ cells/staining were used. After subtracting the fluorescence intensity values of the cells stained with the secondary and tertiary reagents alone the values were used for calculation of the KD values with the equation for one-site-binding (hyperbola) of the GraphPad Prism software (GraphPad Prism version 6.00 for Windows, GraphPad Software, La Jolla Calif. USA).

EGFRvIII binding KD values and EC50 values of cytotoxicity are plotted as a function of the CD3 binding KD values for each of the analysed Tandem diabodies. While the tandem diabodies show only little variability in the EGFRvIII binding KD values, the EC50 cytotoxicity values show an almost linear increase with increasing CD3 binding KD values of the tandem diabodies (FIG. 11).

Example 12: $F98^{EGFRvIII}$ Xenograft Tumor Inhibition by EGFRvIII/CD3 Tandem Diabodies (In Vivo-Proof of Concept)

Nine experimental groups of immunodeficient NOD/scid mice (NOD/MrkBomTac-Prkdcscid, Taconic Denmark) were xenotransplanted by a subcutaneous (s.c.) injection with a suspension of $4 \times 10^6$ of $F98^{npEGFRvIII}$ cells mixed with $1 \times 10^7$ purified human PBMC from healthy donors on day 0 (d0). To account for potential donor variability of the PBMC, each of the experimental groups was subdivided into two cohorts each receiving PBMCs of only one individual donor. Animals were dosed into the tail vein (i.v.) 2 h post tumor cell inoculation and subsequently at 24 h, 48 h, 72 h and 96 h with 100 µg, 10 µg, or 1 µg of the respective tandem diabody test items. A control group received vehicle only. An additional control was dosed i.p. twice a week with 1 mg of Cetuximab (Erbitux) starting on d0. Table 6 summarizes dose groups and donor allocation. The tumor volume was monitored 3 times per week from day 3 to day 52 by measuring the large diameter and the small diameter of a tumor with a caliper. Tumor volumes were calculated from diameters according to the following formula:

$$\text{Vol.} = (\text{small diameter})^2 \times \text{large diameter} \times 0.5.$$

TABLE 7

Dose groups of animals

| Group | Animals (n) | s.c. injection (d 0) | Cohort | (i.v. injection d 0, 1, 2, 3, 4; once/day) |
|---|---|---|---|---|
| 1 | 4 | $4 \times 10^6$ | w/o | Vehicle |
| 2 | 4 | $F98^{npEGFRvIII}$ | $1 \times 10^7$ PBMC (Donor 1) Cohort 1 | Vehicle |
|  | 4 |  | $1 \times 10^7$ PBMC (Donor 2) Cohort 2 |  |
| 3 | 4 |  | $1 \times 10^7$ PBMC (Donor 1) Cohort 1 | 100 µg Tandem diabody |
|  | 4 |  | $1 \times 10^7$ PBMC (Donor 2) Cohort 2 | EGFRvIII(Li3G30)/CD3 |
| 4 | 4 |  | $1 \times 10^7$ PBMC (Donor 1) Cohort 1 | 10 µg (v6) |
|  | 4 |  | $1 \times 10^7$ PBMC (Donor 2) Cohort 2 | $(V_L^{CD3}\text{-}V_H^{EGFRvIII}\text{-}$ |
| 5 | 4 |  | $1 \times 10^7$ PBMC (Donor 1) Cohort 1 | 1 µg $V_L^{EGFRvIII}\text{-}V_H^{CD3})$ |
|  | 4 |  | $1 \times 10^7$ PBMC (Donor 2) Cohort 2 |  |
| 6 | 4 |  | $1 \times 10^7$ PBMC (Donor 1) Cohort 1 | 100 µg Tandem diabody |
|  | 4 |  | $1 \times 10^7$ PBMC (Donor 2) Cohort 2 | EGFRvIII(Li3G30)/CD3 |
| 7 | 4 |  | $1 \times 10^7$ PBMC (Donor 1) Cohort 1 | 10 µg $(V_H^{EGFRvIII}\text{-}V_L^{CD3}\text{-}$ |
|  | 4 |  | $1 \times 10^7$ PBMC (Donor 2) Cohort 2 | $V_H^{CD3}\text{-}V_L^{EGFRvIII})$ |
| 8 | 4 |  | $1 \times 10^7$ PBMC (Donor 1) Cohort 1 |  |
|  | 4 |  | $1 \times 10^7$ PBMC (Donor 2) Cohort 2 | 1 µg (i.p. injection d 0, and d 4, in the following twice per week) |
| 9 | 4 | $4 \times 10^6$ | $1 \times 10^7$ PBMC (Donor 1) Cohort 1 | 1 mg Erbitux |
|  | 4 | $F98^{npEGFRvIII}$ | $1 \times 10^7$ PBMC (Donor 2) Cohort 2 |  |

REFERENCES

Schwarz M, Röttgen P, Takada Y, Le Gall F, Knackmuss S, Bassler N, Büttner C, Little M, Bode C, Peter K. Single-chain antibodies for the conformation-specific blockade of activated platelet integrin alphaIIbbeta3 designed by subtractive selection from naive human phage libraries. FASEB J. 2004 November; 18(14):1704-6.

Schier R, McCall A, Adams G P, Marshall K W, Merritt H, Yim M, Crawford R S, Weiner L M, Marks C, Marks J D. Isolation of picomolar affinity anti-c-erbB-2 single-chain Fv by molecular evolution of the complementarity determining regions in the center of the antibody binding site. J Mol Biol. 1996

Pini A, Viti F, Santucci A, Camemolla B, Zardi L, Neri P, Neri D. Design and use of a phage display library. Human antibodies with subnanomolar affinity against a marker of angiogenesis eluted from a two-dimensional gel. J Biol Chem. 1998

Boder E T, Midelfort K S, Wittrup K D. Directed evolution of antibody fragments with monovalent femtomolar antigen-binding affinity. Proc Natl Acad Sci USA. 2000 Sep. 26; 97(20): 10701-5.

Barbas C F 3rd, Hu D, Dunlop N, Sawyer L, Cababa D, Hendry R M, Nara P L, Burton D R. In vitro evolution of a neutralizing human antibody to human immunodeficiency virus type 1 to enhance affinity and broaden strain cross-reactivity. Proc Natl Acad Sci USA. 1994 Apr. 26; 91(9):3809-13.

Parsons H L, Eamshaw J C, Wilton J, Johnson K S, Schueler P A, Mahoney W, McCafferty J. Directing phage selections towards specific epitopes. Protein Eng. 1996 November; 9(11): 1043-9.

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. 2000 Oct. 15; 165(8):4505-14.

Safdari Y, Farajnia S, Asgharzadeh M, Omidfar K, Khalili M. humMR1, a highly specific humanized single chain antibody for targeting EGFRvIII. Int Immunopharmacol. 2014 February; 18(2):304-10.

Lorimer I A, Keppler-Hafkemeyer A, Beers R A, Pegram C N, Bigner D D, Pastan I. Recombinant immunotoxins specific for a mutant epidermal growth factor receptor: targeting with a single chain antibody variable domain isolated by phage display. Proc Natl Acad Sci USA. 1996 Dec. 10; 93(25):14815-20.

Beers R, Chowdhury P, Bigner D, Pastan I. Immunotoxins with increased activity against epidermal growth factor receptor vIII-expressing cells produced by antibody phage display. Clin Cancer Res. 2000 July; 6(7):2835-43.

Kuan C T, Wikstrand C J, Archer G, Beers R, Pastan I, Zalutsky M R, Bigner D D. Increased binding affinity enhances targeting of glioma xenografts by EGFRvIII-specific scFv. Int J Cancer. 2000 Dec. 15; 88(6):962-9.

Choi B D, Kuan C T, Cai M, Archer G E, Mitchell D A, Gedeon P C, Sanchez-Perez L, Pastan I, Bigner D D, Sampson J H. Systemic administration of a bispecific antibody targeting EGFRvIII successfully treats intracerebral glioma. Proc Natl Acad Sci USA. 2013 Jan. 2; 110(1):270-5.

Fenstermaker R A, Ciesielski M J. Deletion and tandem duplication of exons 2-7 in the epidermal growth factor receptor gene of a human malignant glioma. Oncogene. 2000 Sep. 14; 19(39):4542-8.

Han W, Zhang T, Yu H, Foulke J G, Tang C K. Hypophosphorylation of residue Y1045 leads to defective down-regulation of EGFRvIII. Cancer Biol Ther. 2006 October; 5(10):1361-8.

Grandal M V, Zandi R, Pedersen M W, Willumsen B M, van Deurs B, Poulsen H S. EGFRvIII escapes down-regulation due to impaired internalization and sorting to lysosomes. Carcinogenesis. 2007 July; 28(7):1408-17.

Gan H K, Kaye A H, Luwor R B. The EGFRvIII variant in glioblastoma multiforme. J Clin Neurosci. 2009 June; 16(6):748-54.

Reist C J, Archer G E, Kurpad S N, Wikstrand C J, Vaidyanathan G, Willingham M C, Moscatello D K, Wong A J, Bigner D D, Zalutsky M R. Tumor-specific anti-epidermal growth factor receptor variant III monoclonal antibodies: use of the tyramine-cellobiose radioiodination method enhances cellular retention and uptake in tumor xenograflts. Cancer Res. 1995 Oct. 1; 55(19):4375-82.

Foulon C F, Reist C J, Bigner D D, Zalutsky M R. Radioiodination via D-amino acid peptide enhances cellular retention and tumor xenograft targeting of an internalizing anti-epidermal growth factor receptor variant III monoclonal antibody. Cancer Res. 2000 Aug. 15; 60(16):4453-60.

Kuan C T, Wikstrand C J, Archer G, Beers R, Pastan I, Zalutsky M R, Bigner D D. Increased binding affinity enhances targeting of glioma xenografts by EGFRvIII-specific scFv. Int J Cancer. 2000 Dec. 15; 88(6):962-9.

Patel D, Lahiji A, Patel S, Franklin M, Jimenez X, Hicklin D J, Kang X. Monoclonal antibody cetuximab binds to and down-regulates constitutively activated epidermal growth factor receptor vIII on the cell surface. Anticancer Res. 2007 September-October; 27(5A):3355-66.

Jutten B, Dubois L, Li Y, Aerts H, Wouters B G, Lambin P, Theys J, Lammering G. Binding of cetuximab to the EGFRvIII deletion mutant and its biological consequences in malignant glioma cells. Radiother Oncol. 2009 September; 92(3):393-8.

Dreier A, Barth S, Goswami A, Weis J. Cetuximab induces mitochondrial translocalization of EGFRvIII, but not EGFR: involvement of mitochondria in tumor drug resistance? Tumour Biol. 2012 February; 33(1):85-94.

The invention claimed is:

1. An EGFRvIII binding protein with at least one EGFRvIII binding site comprising an antibody variable heavy chain domain and an antibody variable light chain domain, wherein:

(a1) the CDR1, CDR2, and CDR3 of the antibody variable heavy chain domain comprises the amino acid sequences of SEQ ID NOs: 27, 28, and 29, respectively, and the CDR1, CDR2, and CDR3 of the antibody variable light chain domain comprises the amino acid sequences of SEQ ID NOs: 30, 31, and 32, respectively; or (a2) the CDR1, CDR2, and CDR3 of the antibody variable heavy chain domain comprises the amino acid sequences of SEQ ID NOs: 33, 28, and 29, respectively, and the CDR1, CDR2, and CDR3 of the antibody variable light chain domain comprises the amino acid sequences of SEQ ID NOs: 34, 31, and 35, respectively; or (a3) the CDR1, CDR2, and CDR3 of the antibody variable heavy chain domain comprises the amino acid sequences of SEQ ID NOs: 33, 28, and 29, respectively, and the CDR1, CDR2, and CDR3 of the antibody variable light chain domain comprises the amino acid sequences of SEQ ID NOs: 36, 31, and 37, respectively; or (a4) the CDR1, CDR2, and CDR3 of the antibody variable heavy chain domain comprises the amino acid sequences of SEQ ID NOs: 33, 38, and 29, respectively, and the CDR1, CDR2, and CDR3 of the antibody variable light chain domain comprises the amino acid sequences of SEQ ID NOs: 39, 40, and 41, respectively; or (a5) the CDR1, CDR2, and CDR3 of the antibody variable heavy chain domain comprises the amino acid sequences of SEQ ID NOs: 42, 43, and 29, respectively, and the CDR1, CDR2, and CDR3 of the antibody variable light chain domain comprises the amino acid sequences of SEQ ID NOs: 44, 40, and 45, respectively; or (a6) the CDR1, CDR2, and CDR3 of the antibody variable heavy chain domain comprises the amino acid sequences of SEQ ID NOs: 46, 28, and 29, respectively, and the CDR1, CDR2, and CDR3 of the antibody variable light chain domain comprises the amino acid sequences of SEQ ID NOs: 47, 40, and 48, respectively; or (a7) the CDR1, CDR2, and CDR3 of the antibody variable heavy chain domain comprises the amino acid sequences of SEQ ID NOs: 49, 50, and 29, respectively, and the CDR1, CDR2, and CDR3 of the antibody variable light chain domain comprises the amino acid sequences of SEQ ID NOs: 51, 40, and 52, respectively; or (a8) the CDR1, CDR2, and CDR3 of the antibody variable heavy chain domain comprises the amino acid sequences of SEQ ID NOs: 53, 54, and 29, respectively, and the CDR1, CDR2, and CDR3 of the antibody variable light chain domain comprises the amino acid sequences of SEQ ID NOs: 44, 40, and 55, respectively; or (a9) the CDR1, CDR2, and CDR3 of the antibody variable heavy chain domain comprises the amino acid sequences of SEQ ID NOs: 53, 28, and 29, respectively, and the CDR1, CDR2, and CDR3 of the antibody variable light chain domain comprises the amino acid sequences of SEQ ID NOs: 56, 57, and 58, respectively; or (a10) the CDR1, CDR2, and CDR3 of the antibody variable heavy chain domain comprises the amino acid sequences of SEQ ID NOs: 46, 28, and 29, respectively, and the CDR1, CDR2, and CDR3 of the antibody variable light chain domain comprises the amino acid sequences of SEQ ID NOs: 59, 40, and 60, respectively; or (a11) the CDR1, CDR2, and CDR3 of the antibody variable heavy chain domain comprises the amino acid sequences of SEQ ID NOs: 33, 61, and 29, respectively, and the CDR1, CDR2, and CDR3 of the antibody variable light chain domain comprises the amino acid sequences of SEQ ID NOs: 44, 40, and 62, respectively; or (a12) the CDR1, CDR2, and CDR3 of the antibody variable heavy chain domain comprises the amino acid sequences of SEQ ID NOs: 69, 63, and 29, respectively, and the CDR1, CDR2, and CDR3 of the antibody variable light chain domain comprises the amino acid sequences of SEQ ID NOs: 64, 31, and 65, respectively;

or (b) the antibody variable heavy chain domain is selected from the group consisting of SEQ ID NOs: 1, 3, 5, 7, 9, 11, 13, 15, 17, 19, 21, 25; and the antibody variable light chain domain is selected from the group consisting of SEQ ID NOs: 2, 4, 6, 8, 10, 12, 14, 16, 18, 20, 22, and 26.

2. The EGFRvIII binding protein according to claim 1, comprising an antibody variable heavy chain domain of SEQ ID NO: 5 or 7, and an antibody variable light chain domain of SEQ ID NO: 8 or 26.

3. The EGFRvIII binding protein according to claim 1, wherein at least 80% of EGFRvIII receptor molecules present on untreated cells are still available on the cell surface after the exposition of the cells to the EGFRvIII binding protein at saturation conditions of the binding protein at 37° C. for 24 hours.

4. The EGFRvIII binding protein according to claim 1, wherein the protein comprises at least one further antigen-binding site.

5. The EGFRvIII binding protein according to claim 4, wherein the at least one further antigen-binding site is an effector domain.

6. The EGFRvIII binding protein according to claim 5, wherein the further antigen-binding site is specific for T- or NK-cells.

7. The EGFRvIII binding protein according to claim 6, wherein the further antigen-binding site is a CD3 binding site comprising at least one antibody variable heavy chain domain and at least one variable light chain domain forming an antigen binding site for CD3.

8. The EGFRvIII binding protein of claim 1, wherein the binding protein is multispecific.

9. The EGFRvIII binding protein of claim 1, wherein the binding protein is trispecific.

10. The EGFRvIII binding protein of claim 1, wherein the binding protein is a dimeric protein.

11. The EGFRvIII binding protein of claim 10, wherein the binding protein is a tandem diabody specific for EGFRvIII and CD3 or a tandem diabody specific for EGFRvIII and CD16A.

12. The dimeric EGFRvIII binding protein of claim 11, wherein in each tandem diabody the four variable chain domains are fused with one another by peptide linkers L1, L2 and L3 in the order of:

(i) VL (CD3)-L1-VH (EGFRvIII)-L2-VL(EGFRvIII)-L3-VH(CD3); or (ii) VH (CD3)-L1-VL(EGFRvIII)-L2-VH(EGFRvIII)-L3-VL(CD3); or (iii) VL(EGFRvIII)-L1-VH(CD3)-L2-VL(CD3)-L3-VH (EGFRvIII); or (iv) VH(EGFRvIII)-L1-VL(CD3)-L2-VH(CD3)-L3-VL (EGFRvIII);

wherein linkers L1, L2 and L3 consist of about 12 amino acid residues or less.

13. The tandem diabody according to claim 12, wherein linkers L1, L2 and L3 consist of 3 to 10 amino acid residues.

14. The tandem diabody according to claim 13, wherein the linkers are SEQ ID NO: 66, 67, or 68.

15. A polynucleotide encoding the EGFRvIII binding protein according to claim 1.

16. A vector comprising the polynucleotide of claim 15.

17. A host cell transformed or transfected with the vector according to claim 16.

18. A pharmaceutical composition comprising the EGFRvIII binding protein according to claim 1, and a pharmaceutically acceptable carrier.

19. A pharmaceutical composition comprising the tandem diabody according to claim 13, and a pharmaceutically acceptable carrier.

20. The EGFRvIII binding protein according to claim 7, wherein the CD3 binding site comprises a variable heavy chain domain having the amino acid sequence of SEQ ID NO: 23 and a variable light chain domain having the amino acid sequence of SEQ ID NO: 24.

21. The EGFRvIII binding protein according to claim 1, comprising a variable heavy chain domain of SEQ ID NO: 25 and a variable light chain domain of SEQ ID NO: 6.

* * * * *

UNITED STATES PATENT AND TRADEMARK OFFICE
CERTIFICATE OF CORRECTION

PATENT NO. : 10,273,309 B2
APPLICATION NO. : 15/015261
DATED : April 30, 2019
INVENTOR(S) : Kristina Ellwanger et al.

It is certified that error appears in the above-identified patent and that said Letters Patent is hereby corrected as shown below:

On the Title Page

Item (73) delete:
"AFFEMED GmbH"
And insert:
--Affimed GmbH--

Signed and Sealed this
Twenty-fifth Day of June, 2019

Andrei Iancu
*Director of the United States Patent and Trademark Office*

SEQUENCE LISTING

```
<160> NUMBER OF SEQ ID NOS: 70

<210> SEQ ID NO 1
<211> LENGTH: 121
<212> TYPE: PRT
<213> ORGANISM: artificial sequence
<220> FEATURE:
<223> OTHER INFORMATION: variable domain
```

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 2
<211> LENGTH: 108
<212> TYPE: PRT
<213> ORGANISM: artificial sequence
<220> FEATURE:
<223> OTHER INFORMATION: variable domain

<400> SEQUENCE: 2

Leu Thr Gln Pro Pro Ser Tyr Glu Ser Val Ser Val Ser Pro Gly Gln
1               5                   10                  15

Thr Ala Arg Ile Thr Cys Ser Gly Asp Thr Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Val Ser Gly Thr Tyr
                85                  90                  95

Val Val Phe Gly Gly Gly Thr Lys Leu Thr Val Leu
            100                 105

<210> SEQ ID NO 3
<211> LENGTH: 121
<212> TYPE: PRT
<213> ORGANISM: artificial sequence
<220> FEATURE:
<223> OTHER INFORMATION: variable domain

<400> SEQUENCE: 3

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 4
<211> LENGTH: 108
<212> TYPE: PRT
<213> ORGANISM: artificial sequence
<220> FEATURE:
<223> OTHER INFORMATION: variable domain

<400> SEQUENCE: 4

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Asp Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser Glu Thr Tyr
                85                  90                  95

Val Val Phe Gly Gly Gly Thr Lys Leu Thr Val Leu
            100                 105

<210> SEQ ID NO 5
<211> LENGTH: 121
<212> TYPE: PRT
<213> ORGANISM: artificial sequence
<220> FEATURE:
<223> OTHER INFORMATION: variable domain

<400> SEQUENCE: 5

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Ala Asn Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 6

```
<211> LENGTH: 108
<212> TYPE: PRT
<213> ORGANISM: artificial sequence
<220> FEATURE:
<223> OTHER INFORMATION: variable domain

<400> SEQUENCE: 6

Ser Tyr Glu Leu Thr Gln Pro Pro Ser Val Ser Val Ser Pro Gly Gln
1               5                   10                  15

Thr Ala Arg Ile Thr Cys Ser Gly Asp Tyr Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser His Pro Ser
                85                  90                  95

Val Val Phe Gly Gly Gly Thr Lys Leu Thr Val Leu
            100                 105

<210> SEQ ID NO 7
<211> LENGTH: 121
<212> TYPE: PRT
<213> ORGANISM: artificial sequence
<220> FEATURE:
<223> OTHER INFORMATION: variable domain

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Gly Tyr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser His Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 8
<211> LENGTH: 108
<212> TYPE: PRT
<213> ORGANISM: artificial sequence
<220> FEATURE:
<223> OTHER INFORMATION: variable domain

<400> SEQUENCE: 8

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30
```

Tyr Trp Tyr Gln Gln Lys Pro Gly Gln Ala Pro Val Leu Val Ile Tyr
            35                  40                  45

Lys Asp Thr Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Val Asp Ser Ser Gly Thr Gln
                 85                  90                  95

Val Val Phe Gly Gly Gly Thr Lys Leu Thr Val Leu
                100                 105

<210> SEQ ID NO 9
<211> LENGTH: 121
<212> TYPE: PRT
<213> ORGANISM: artificial sequence
<220> FEATURE:
<223> OTHER INFORMATION: variable domain

<400> SEQUENCE: 9

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ser Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Ser Ser Trp Thr Asn Asp Ala Phe Asp Ile Trp Gly
                100                 105                 110

Gln Gly Thr Leu Val Thr Val Ser Ser
            115                 120

<210> SEQ ID NO 10
<211> LENGTH: 108
<212> TYPE: PRT
<213> ORGANISM: artificial sequence
<220> FEATURE:
<223> OTHER INFORMATION: variable domain

<400> SEQUENCE: 10

Ser Tyr Glu Leu Thr Gln Pro Pro Ser Val Ser Val Ser Pro Gly Gln
 1               5                  10                  15

Thr Ala Arg Ile Thr Cys Ser Gly His Ala Leu Pro Ser Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Val Asp Ser Ser Gly Thr Ser
                 85                  90                  95

Val Ile Phe Gly Gly Gly Thr Lys Leu Thr Val Leu
                100                 105

```
<210> SEQ ID NO 11
<211> LENGTH: 121
<212> TYPE: PRT
<213> ORGANISM: artificial sequence
<220> FEATURE:
<223> OTHER INFORMATION: variable domain

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser His Tyr
            20                  25                  30

Trp Ile Gly Trp Val Arg Gln Met Pro Gly Lys Gly Leu Glu Trp Met
        35                  40                  45

Gly Ile Thr Tyr Pro Gly Asp Val Asp Thr Arg Tyr Asp Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 12
<211> LENGTH: 108
<212> TYPE: PRT
<213> ORGANISM: artificial sequence
<220> FEATURE:
<223> OTHER INFORMATION: variable domain

<400> SEQUENCE: 12

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Thr Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Leu Val Phe Gly Gly Gly Thr Lys Leu Thr Val Leu
            100                 105

<210> SEQ ID NO 13
<211> LENGTH: 121
<212> TYPE: PRT
<213> ORGANISM: artificial sequence
<220> FEATURE:
<223> OTHER INFORMATION: variable domain

<400> SEQUENCE: 13

Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ser Phe Thr Ser Tyr
              20                  25                  30

Trp Ile Gly Trp Val Arg Gln Met Pro Gly Lys Gly Leu Glu Trp Met
          35                  40                  45

Gly Ile Ile Tyr Pro Asp Asp Ser Asp Thr Arg Tyr Ser Pro Ser Phe
      50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
              85                  90                  95

Ala Arg Leu Gly Ser Ser Trp Thr Asn Asp Ala Phe Asp Ile Trp Gly
          100                 105                 110

Gln Gly Thr Leu Val Thr Val Ser Ser
          115                 120

<210> SEQ ID NO 14
<211> LENGTH: 108
<212> TYPE: PRT
<213> ORGANISM: artificial sequence
<220> FEATURE:
<223> OTHER INFORMATION: variable domain

<400> SEQUENCE: 14

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
              20                  25                  30

Tyr Trp Tyr Gln Gln Lys Pro Gly Gln Ala Pro Val Leu Val Ile Tyr
          35                  40                  45

Lys Asp Thr Glu Arg Pro Ser Gly Ile Pro Glu Arg Phe Ser Gly Ser
      50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser Gly Thr Tyr
              85                  90                  95

Val Val Phe Gly Gly Gly Thr Lys Leu Thr Val Leu
          100                 105

<210> SEQ ID NO 15
<211> LENGTH: 121
<212> TYPE: PRT
<213> ORGANISM: artificial sequence
<220> FEATURE:
<223> OTHER INFORMATION: variable domain

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
              20                  25                  30

Trp Ile Gly Trp Val Arg Gln Met Pro Gly Lys Gly Leu Glu Trp Met
          35                  40                  45

Gly Ile Ile Tyr Pro Gly Asp Ser Asp Thr Arg Tyr Ser Pro Ser Phe
      50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
              85                  90                  95

```
Ala Arg Leu Gly Ser Ser Trp Thr Asn Asp Ala Phe Asp Ile Trp Gly
            100                 105                 110

Gln Gly Thr Leu Val Thr Val Ser Ser
        115                 120
```

```
<210> SEQ ID NO 16
<211> LENGTH: 108
<212> TYPE: PRT
<213> ORGANISM: artificial sequence
<220> FEATURE:
<223> OTHER INFORMATION: variable domain

<400> SEQUENCE: 16
```

```
Ser Tyr Glu Leu Thr Gln Pro Pro Ser Val Ser Val Ser Pro Gly Gln
1               5                   10                  15

Thr Ala Arg Ile Thr Cys Ser Gly Asp Asn Ile Pro His Gln Tyr Ala
            20                  25                  30

Tyr Trp Tyr Gln Gln Lys Pro Gly Gln Ala Pro Val Leu Val Ile Tyr
            35                  40                  45

Lys Asp Thr Glu Arg Pro Ala Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Pro Thr Gly Ala Tyr
                85                  90                  95

Leu Val Phe Gly Gly Gly Thr Lys Leu Thr Val Leu
            100                 105
```

```
<210> SEQ ID NO 17
<211> LENGTH: 121
<212> TYPE: PRT
<213> ORGANISM: artificial sequence
<220> FEATURE:
<223> OTHER INFORMATION: variable domain

<400> SEQUENCE: 17
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120
```

```
<210> SEQ ID NO 18
<211> LENGTH: 108
<212> TYPE: PRT
<213> ORGANISM: artificial sequence
<220> FEATURE:
<223> OTHER INFORMATION: variable domain
```

```
<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Asp Tyr Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ala Ser Gly Thr Tyr
                85                  90                  95

Tyr Val Phe Gly Gly Gly Thr Lys Leu Thr Val Leu
            100                 105

<210> SEQ ID NO 19
<211> LENGTH: 121
<212> TYPE: PRT
<213> ORGANISM: artificial sequence
<220> FEATURE:
<223> OTHER INFORMATION: variable domain

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asn Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Glu Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 20
<211> LENGTH: 108
<212> TYPE: PRT
<213> ORGANISM: artificial sequence
<220> FEATURE:
<223> OTHER INFORMATION: variable domain

<400> SEQUENCE: 20

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
50                  55                  60
```

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Pro Ser Gly Thr Tyr
                85                  90                  95

Val Val Phe Gly Gly Gly Thr Lys Leu Thr Val Leu
            100                 105

<210> SEQ ID NO 21
<211> LENGTH: 121
<212> TYPE: PRT
<213> ORGANISM: artificial sequence
<220> FEATURE:
<223> OTHER INFORMATION: variable domain

<400> SEQUENCE: 21

Gln Ser Gly Ala Glu Val Lys Lys Pro Gly Glu Val Gln Leu Val Glu
1               5                   10                  15

Ser Leu Lys Ile Ser Cys Lys Gly Ser Gly Tyr Asp Phe Ser Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Ser Ser Trp Thr Asn Asp Ala Phe Asp Ile Trp Gly
            100                 105                 110

Gln Gly Thr Leu Val Thr Val Ser Ser
        115                 120

<210> SEQ ID NO 22
<211> LENGTH: 108
<212> TYPE: PRT
<213> ORGANISM: artificial sequence
<220> FEATURE:
<223> OTHER INFORMATION: variable domain

<400> SEQUENCE: 22

Ser Tyr Glu Leu Thr Gln Pro Pro Ser Val Ser Val Ser Pro Gly Gln
1               5                   10                  15

Thr Ala Arg Ile Thr Cys Ser Gly Ala Ala Leu Pro Glu Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Val Asp Ser Ser Gly Thr Phe
                85                  90                  95

Tyr Val Phe Gly Gly Gly Thr Lys Leu Thr Val Leu
            100                 105

<210> SEQ ID NO 23
<211> LENGTH: 125
<212> TYPE: PRT

```
<213> ORGANISM: artificial sequence
<220> FEATURE:
<223> OTHER INFORMATION: variable domain

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Tyr Phe
            100                 105                 110

Ala Tyr Trp Gly Gln Gly Thr Leu Val Thr Val Ser Ser
        115                 120                 125

<210> SEQ ID NO 24
<211> LENGTH: 110
<212> TYPE: PRT
<213> ORGANISM: artificial sequence
<220> FEATURE:
<223> OTHER INFORMATION: variable domain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ser Ser Thr Gly Ala Val Thr Thr
            20                  25                  30

Ser Asn Tyr Ala Asn Trp Val Gln Gln Lys Pro Gly Lys Ala Pro Lys
        35                  40                  45

Ala Leu Ile Gly Gly Thr Asn Lys Arg Ala Pro Gly Val Pro Ser Arg
    50                  55                  60

Phe Ser Gly Ser Leu Ile Gly Asp Lys Ala Thr Leu Thr Ile Ser Ser
65                  70                  75                  80

Leu Gln Pro Glu Asp Phe Ala Thr Tyr Tyr Cys Ala Leu Trp Tyr Ser
                85                  90                  95

Asn Leu Trp Val Phe Gly Gln Gly Thr Lys Val Glu Ile Lys
            100                 105                 110

<210> SEQ ID NO 25
<211> LENGTH: 121
<212> TYPE: PRT
<213> ORGANISM: artificial sequence
<220> FEATURE:
<223> OTHER INFORMATION: variable domain

<400> SEQUENCE: 25

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45
```

```
Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Ser Ser Trp Thr Asn Asp Ala Phe Asp Ile Trp Gly
            100                 105                 110

Gln Gly Thr Met Val Thr Val Ser Ser
            115                 120
```

<210> SEQ ID NO 26
<211> LENGTH: 109
<212> TYPE: PRT
<213> ORGANISM: artificial sequence
<220> FEATURE:
<223> OTHER INFORMATION: variable domain

<400> SEQUENCE: 26

```
Ser Tyr Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Ala
             20                  25                  30

Tyr Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly Thr Pro
                 85                  90                  95

Leu Ile Val Phe Gly Thr Gly Thr Lys Leu Thr Val Leu
            100                 105
```

<210> SEQ ID NO 27
<211> LENGTH: 9
<212> TYPE: PRT
<213> ORGANISM: artificial sequence
<220> FEATURE:
<223> OTHER INFORMATION: cdr

<400> SEQUENCE: 27

```
Tyr Ser Phe Thr Ser Tyr Trp Ile Gly
 1               5
```

<210> SEQ ID NO 28
<211> LENGTH: 13
<212> TYPE: PRT
<213> ORGANISM: artificial sequence
<220> FEATURE:
<223> OTHER INFORMATION: cdr

<400> SEQUENCE: 28

```
Gly Ile Ile Tyr Pro Gly Asp Ser Asp Thr Arg Tyr Ser
 1               5                  10
```

<210> SEQ ID NO 29
<211> LENGTH: 12
<212> TYPE: PRT
<213> ORGANISM: artificial sequence
<220> FEATURE:

```
<223> OTHER INFORMATION: cdr

<400> SEQUENCE: 29

Leu Gly Ser Ser Trp Thr Asn Asp Ala Phe Asp Ile
1               5                   10

<210> SEQ ID NO 30
<211> LENGTH: 11
<212> TYPE: PRT
<213> ORGANISM: artificial sequence
<220> FEATURE:
<223> OTHER INFORMATION: variable domain

<400> SEQUENCE: 30

Ser Gly Asp Ala Leu Pro Lys Gln Tyr Ala Tyr
1               5                   10

<210> SEQ ID NO 31
<211> LENGTH: 7
<212> TYPE: PRT
<213> ORGANISM: artificial sequence
<220> FEATURE:
<223> OTHER INFORMATION: cdr

<400> SEQUENCE: 31

Lys Asp Ser Glu Arg Pro Ser
1               5

<210> SEQ ID NO 32
<211> LENGTH: 12
<212> TYPE: PRT
<213> ORGANISM: artificial sequence
<220> FEATURE:
<223> OTHER INFORMATION: cdr

<400> SEQUENCE: 32

Gln Ser Ala Asp Ser Ser Gly Thr Pro Leu Ile Val
1               5                   10

<210> SEQ ID NO 33
<211> LENGTH: 9
<212> TYPE: PRT
<213> ORGANISM: artificial sequence
<220> FEATURE:
<223> OTHER INFORMATION: cdr

<400> SEQUENCE: 33

Tyr Ser Phe Asn Ser Tyr Trp Ile Gly
1               5

<210> SEQ ID NO 34
<211> LENGTH: 11
<212> TYPE: PRT
<213> ORGANISM: artificial sequence
<220> FEATURE:
<223> OTHER INFORMATION: cdr

<400> SEQUENCE: 34

Ser Gly Asp Thr Leu Pro Lys Gln Tyr Ala Tyr
1               5                   10

<210> SEQ ID NO 35
<211> LENGTH: 11
<212> TYPE: PRT
<213> ORGANISM: artificial sequence
<220> FEATURE:
<223> OTHER INFORMATION: cdr
```

```
<400> SEQUENCE: 35

Gln Ser Val Asp Val Ser Gly Thr Tyr Val Val
1               5                   10

<210> SEQ ID NO 36
<211> LENGTH: 11
<212> TYPE: PRT
<213> ORGANISM: artificial sequence
<220> FEATURE:
<223> OTHER INFORMATION: cdr

<400> SEQUENCE: 36

Ser Gly Asp Ala Leu Asp Lys Gln Tyr Ala Tyr
1               5                   10

<210> SEQ ID NO 37
<211> LENGTH: 11
<212> TYPE: PRT
<213> ORGANISM: artificial sequence
<220> FEATURE:
<223> OTHER INFORMATION: cdr

<400> SEQUENCE: 37

Gln Ser Val Asp Ser Ser Glu Thr Tyr Val Val
1               5                   10

<210> SEQ ID NO 38
<211> LENGTH: 13
<212> TYPE: PRT
<213> ORGANISM: artificial sequence
<220> FEATURE:
<223> OTHER INFORMATION: cdr

<400> SEQUENCE: 38

Gly Ile Ile Tyr Pro Gly Asp Ser Ala Asn Arg Tyr Ser
1               5                   10

<210> SEQ ID NO 39
<211> LENGTH: 11
<212> TYPE: PRT
<213> ORGANISM: artificial sequence
<220> FEATURE:
<223> OTHER INFORMATION: cdr

<400> SEQUENCE: 39

Ser Gly Asp Tyr Leu Pro Lys Gln Tyr Ala Tyr
1               5                   10

<210> SEQ ID NO 40
<211> LENGTH: 7
<212> TYPE: PRT
<213> ORGANISM: artificial sequence
<220> FEATURE:
<223> OTHER INFORMATION: cdr

<400> SEQUENCE: 40

Lys Asp Thr Glu Arg Pro Ser
1               5

<210> SEQ ID NO 41
<211> LENGTH: 11
<212> TYPE: PRT
<213> ORGANISM: artificial sequence
<220> FEATURE:
<223> OTHER INFORMATION: cdr
```

```
<400> SEQUENCE: 41

Gln Ser Val Asp Ser Ser His Pro Ser Val Val
1               5                   10

<210> SEQ ID NO 42
<211> LENGTH: 9
<212> TYPE: PRT
<213> ORGANISM: artificial sequence
<220> FEATURE:
<223> OTHER INFORMATION: cdr

<400> SEQUENCE: 42

Tyr Ser Phe Gly Tyr Tyr Trp Ile Gly
1               5

<210> SEQ ID NO 43
<211> LENGTH: 13
<212> TYPE: PRT
<213> ORGANISM: artificial sequence
<220> FEATURE:
<223> OTHER INFORMATION: cdr

<400> SEQUENCE: 43

Gly Ile Ile Tyr Pro Gly Asp Ser His Thr Arg Tyr Ser
1               5                   10

<210> SEQ ID NO 44
<211> LENGTH: 11
<212> TYPE: PRT
<213> ORGANISM: artificial sequence
<220> FEATURE:
<223> OTHER INFORMATION: cdr

<400> SEQUENCE: 44

Ser Gly Asp Ala Leu Pro Lys Gln Tyr Ala Tyr
1               5                   10

<210> SEQ ID NO 45
<211> LENGTH: 11
<212> TYPE: PRT
<213> ORGANISM: artificial sequence
<220> FEATURE:
<223> OTHER INFORMATION: cdr

<400> SEQUENCE: 45

Gln Ser Val Asp Ser Ser Gly Thr Gln Val Val
1               5                   10

<210> SEQ ID NO 46
<211> LENGTH: 9
<212> TYPE: PRT
<213> ORGANISM: artificial sequence
<220> FEATURE:
<223> OTHER INFORMATION: cdr

<400> SEQUENCE: 46

Tyr Ser Phe Ser Ser Tyr Trp Ile Gly
1               5

<210> SEQ ID NO 47
<211> LENGTH: 11
<212> TYPE: PRT
<213> ORGANISM: artificial sequence
<220> FEATURE:
<223> OTHER INFORMATION: cdr

<400> SEQUENCE: 47
```

Ser Gly His Ala Leu Pro Ser Gln Tyr Ala Tyr
1               5                   10

<210> SEQ ID NO 48
<211> LENGTH: 11
<212> TYPE: PRT
<213> ORGANISM: artificial sequence
<220> FEATURE:
<223> OTHER INFORMATION: cdr

<400> SEQUENCE: 48

Gln Ser Val Asp Ser Ser Gly Thr Ser Val Ile
1               5                   10

<210> SEQ ID NO 49
<211> LENGTH: 9
<212> TYPE: PRT
<213> ORGANISM: artificial sequence
<220> FEATURE:
<223> OTHER INFORMATION: cdr

<400> SEQUENCE: 49

Tyr Ser Phe Ser His Tyr Trp Ile Gly
1               5

<210> SEQ ID NO 50
<211> LENGTH: 13
<212> TYPE: PRT
<213> ORGANISM: artificial sequence
<220> FEATURE:
<223> OTHER INFORMATION: cdr

<400> SEQUENCE: 50

Gly Ile Thr Tyr Pro Gly Asp Val Asp Thr Arg Tyr Asp
1               5                   10

<210> SEQ ID NO 51
<211> LENGTH: 11
<212> TYPE: PRT
<213> ORGANISM: artificial sequence
<220> FEATURE:
<223> OTHER INFORMATION: cdr

<400> SEQUENCE: 51

Ser Gly Asp Ala Leu Pro Lys Thr Tyr Ala Tyr
1               5                   10

<210> SEQ ID NO 52
<211> LENGTH: 11
<212> TYPE: PRT
<213> ORGANISM: artificial sequence
<220> FEATURE:
<223> OTHER INFORMATION: cdr

<400> SEQUENCE: 52

Gln Ser Ala Asp Ser Ser Gly Thr Tyr Leu Val
1               5                   10

<210> SEQ ID NO 53
<211> LENGTH: 9
<212> TYPE: PRT
<213> ORGANISM: artificial sequence
<220> FEATURE:
<223> OTHER INFORMATION: cdr

<400> SEQUENCE: 53

```
Tyr Ser Phe Thr Ser Tyr Trp Ile Gly
1               5

<210> SEQ ID NO 54
<211> LENGTH: 13
<212> TYPE: PRT
<213> ORGANISM: artificial sequence
<220> FEATURE:
<223> OTHER INFORMATION: cdr

<400> SEQUENCE: 54

Gly Ile Ile Tyr Pro Asp Asp Ser Asp Thr Arg Tyr Ser
1               5                   10

<210> SEQ ID NO 55
<211> LENGTH: 11
<212> TYPE: PRT
<213> ORGANISM: artificial sequence
<220> FEATURE:
<223> OTHER INFORMATION: cdr

<400> SEQUENCE: 55

Gln Ser Val Asp Ser Ser Gly Thr Tyr Val Val
1               5                   10

<210> SEQ ID NO 56
<211> LENGTH: 11
<212> TYPE: PRT
<213> ORGANISM: artificial sequence
<220> FEATURE:
<223> OTHER INFORMATION: cdr

<400> SEQUENCE: 56

Ser Gly Asp Asn Ile Pro His Gln Tyr Ala Tyr
1               5                   10

<210> SEQ ID NO 57
<211> LENGTH: 7
<212> TYPE: PRT
<213> ORGANISM: artificial sequence
<220> FEATURE:
<223> OTHER INFORMATION: cdr

<400> SEQUENCE: 57

Lys Asp Thr Glu Arg Pro Ala
1               5

<210> SEQ ID NO 58
<211> LENGTH: 11
<212> TYPE: PRT
<213> ORGANISM: artificial sequence
<220> FEATURE:
<223> OTHER INFORMATION: cdr

<400> SEQUENCE: 58

Gln Ser Ala Asp Pro Thr Gly Ala Tyr Leu Val
1               5                   10

<210> SEQ ID NO 59
<211> LENGTH: 11
<212> TYPE: PRT
<213> ORGANISM: artificial sequence
<220> FEATURE:
<223> OTHER INFORMATION: cdr

<400> SEQUENCE: 59

Ser Gly Asp Tyr Leu Pro Lys Gln Tyr Ala Tyr
```

```
1               5                   10
```

<210> SEQ ID NO 60
<211> LENGTH: 11
<212> TYPE: PRT
<213> ORGANISM: artificial sequence
<220> FEATURE:
<223> OTHER INFORMATION: cdr

<400> SEQUENCE: 60

```
Gln Ser Ala Asp Ala Ser Gly Thr Tyr Tyr Val
1               5                   10
```

<210> SEQ ID NO 61
<211> LENGTH: 13
<212> TYPE: PRT
<213> ORGANISM: artificial sequence
<220> FEATURE:
<223> OTHER INFORMATION: cdr

<400> SEQUENCE: 61

```
Gly Ile Ile Tyr Pro Gly Asp Glu Asp Thr Arg Tyr Ser
1               5                   10
```

<210> SEQ ID NO 62
<211> LENGTH: 11
<212> TYPE: PRT
<213> ORGANISM: artificial sequence
<220> FEATURE:
<223> OTHER INFORMATION: cdr

<400> SEQUENCE: 62

```
Gln Ser Val Asp Pro Ser Gly Thr Tyr Val Val
1               5                   10
```

<210> SEQ ID NO 63
<211> LENGTH: 13
<212> TYPE: PRT
<213> ORGANISM: artificial sequence
<220> FEATURE:
<223> OTHER INFORMATION: cdr

<400> SEQUENCE: 63

```
Gly Ile Ile Tyr Pro Gly Asp Ser Asp Thr Ile Tyr Ser
1               5                   10
```

<210> SEQ ID NO 64
<211> LENGTH: 11
<212> TYPE: PRT
<213> ORGANISM: artificial sequence
<220> FEATURE:
<223> OTHER INFORMATION: cdr

<400> SEQUENCE: 64

```
Ser Gly Ala Ala Leu Pro Glu Gln Tyr Ala Tyr
1               5                   10
```

<210> SEQ ID NO 65
<211> LENGTH: 11
<212> TYPE: PRT
<213> ORGANISM: artificial sequence
<220> FEATURE:
<223> OTHER INFORMATION: cdr

<400> SEQUENCE: 65

```
Gln Ser Val Asp Ser Ser Gly Thr Phe Tyr Val
1               5                   10
```

```
<210> SEQ ID NO 66
<211> LENGTH: 6
<212> TYPE: PRT
<213> ORGANISM: artificial sequence
<220> FEATURE:
<223> OTHER INFORMATION: linker

<400> SEQUENCE: 66

Gly Gly Ser Gly Gly Ser
1               5

<210> SEQ ID NO 67
<211> LENGTH: 4
<212> TYPE: PRT
<213> ORGANISM: artificial sequence
<220> FEATURE:
<223> OTHER INFORMATION: linker

<400> SEQUENCE: 67

Gly Gly Ser Gly
1

<210> SEQ ID NO 68
<211> LENGTH: 5
<212> TYPE: PRT
<213> ORGANISM: artificial sequence
<220> FEATURE:
<223> OTHER INFORMATION: linker

<400> SEQUENCE: 68

Gly Gly Ser Gly Gly
1               5

<210> SEQ ID NO 69
<211> LENGTH: 9
<212> TYPE: PRT
<213> ORGANISM: artificial sequence
<220> FEATURE:
<223> OTHER INFORMATION: cdr

<400> SEQUENCE: 69

Tyr Asp Phe Ser Ser Tyr Trp Ile Gly
1               5

<210> SEQ ID NO 70
<211> LENGTH: 9
<212> TYPE: PRT
<213> ORGANISM: artificial sequence
<220> FEATURE:
<223> OTHER INFORMATION: cdr

<400> SEQUENCE: 70

Gln Ser Ala Asp Ser Ser Gly Thr Tyr
1               5
```